US012427193B2

(12) United States Patent
Adler et al.

(10) Patent No.: US 12,427,193 B2
(45) Date of Patent: *Sep. 30, 2025

(54) SUBCUTANEOUS ANTI-HER2 ANTIBODY FORMULATIONS AND USES THEREOF

(71) Applicant: Genentech, Inc., South San Francisco, CA (US)

(72) Inventors: Michael Adler, Lörrach (DE); Ulla Grauschopf, Riehen (CH); Hanns-Christian Mahler, Lörrach (DE); Oliver Boris Stauch, Dornstadt (DE)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/991,315

(22) Filed: Dec. 20, 2024

(65) Prior Publication Data

US 2025/0121059 A1 Apr. 17, 2025

Related U.S. Application Data

(60) Division of application No. 18/635,280, filed on Apr. 15, 2024, which is a continuation of application No. 18/459,857, filed on Sep. 1, 2023, now abandoned, which is a continuation of application No. 17/443,780, filed on Jul. 27, 2021, now abandoned, which is a continuation of application No. 15/949,616, filed on Apr. 10, 2018, now abandoned, which is a continuation of application No. 15/053,217, filed on Feb. 25, 2016, now Pat. No. 9,968,676, which is a continuation of application No. 13/833,316, filed on Mar. 15, 2013, now abandoned, which is a continuation of application No. 12/804,703, filed on Jul. 27, 2010, now Pat. No. 9,345,661.

(30) Foreign Application Priority Data

Jul. 31, 2009 (EP) .................... 09167025

(51) Int. Cl.
| | |
|---|---|
| A61K 9/19 | (2006.01) |
| A61K 9/00 | (2006.01) |
| A61K 9/08 | (2006.01) |
| A61K 38/47 | (2006.01) |
| A61K 39/395 | (2006.01) |
| A61K 45/06 | (2006.01) |
| A61K 47/18 | (2017.01) |
| A61K 47/20 | (2006.01) |
| A61K 47/26 | (2006.01) |
| A61K 47/42 | (2017.01) |
| C07K 16/32 | (2006.01) |

(52) U.S. Cl.
CPC ...... *A61K 39/39558* (2013.01); *A61K 9/0019* (2013.01); *A61K 9/08* (2013.01); *A61K 9/19* (2013.01); *A61K 38/47* (2013.01); *A61K 39/39591* (2013.01); *A61K 45/06* (2013.01); *A61K 47/18* (2013.01); *A61K 47/183* (2013.01); *A61K 47/20* (2013.01); *A61K 47/26* (2013.01); *A61K 47/42* (2013.01); *C07K 16/32* (2013.01); *C12Y 302/01035* (2013.01)

(58) Field of Classification Search
CPC .................................................. A61K 39/39558
USPC ...................................................... 424/133.1
See application file for complete search history.

(56) References Cited

U.S. PATENT DOCUMENTS

| | | | |
|---|---|---|---|
| 2,795,529 | A | 6/1957 | Alburn et al. |
| 4,943,533 | A | 7/1990 | Mendelsohn et al. |
| 5,573,186 | A | 11/1996 | Loschelder |
| 5,677,171 | A | 10/1997 | Hudziak et al. |
| 5,721,348 | A | 2/1998 | Primakoff et al. |
| 5,783,186 | A | 7/1998 | Arakawa et al. |
| 5,821,337 | A | 10/1998 | Carter et al. |
| 5,891,996 | A | 4/1999 | Mateo De Acosta Del Rio et al. |

(Continued)

FOREIGN PATENT DOCUMENTS

| | | |
|---|---|---|
| CL | 2756-2005 | 10/2005 |
| CL | 2007000797 A1 | 1/2008 |

(Continued)

OTHER PUBLICATIONS

Pegram et al (Oncogene, 1999, 18(13): 2241-2251).*
Arpino et al (J Natl Cancer Inst, 2007, 99: 694-705).*
Adler, Resume Dr. Michael Adler: p. 1 (Aug. 18, 2015).
Ahamed et al., "Trastuzumab: unusual responses and toxicities" Future Oncology 5(6):779-784 ( 2009).
Akers et al., "Formulation development of protein dosage forms" Pharmaceutical Biotechnol 14:47-127 (Jan. 1, 2002).
Annex A to Declaration of Dr. Michael Alder, in Opposition to EP 2459167 dated Aug. 17, 2015 Curriculum Vitae of Dr. Michael Alder (1 page).

(Continued)

*Primary Examiner* — Sean E Aeder
(74) *Attorney, Agent, or Firm* — Wendy M Lee

(57) ABSTRACT

The present invention relates to a highly concentrated, stable pharmaceutical formulation of a pharmaceutically active anti-HER2 antibody, such as e.g. Trastuzumab (HERCEPTIN™), Pertuzumab or T-DM1, or a mixture of such antibody molecules for subcutaneous injection. In particular, the present invention relates to formulations comprising, in addition to a suitable amount of the anti-HER2 antibody, an effective amount of at least one hyaluronidase enzyme as a combined formulation or for use in form of a co-formulation. The formulations comprise additionally at least one buffering agent, such as e.g. a histidine buffer, a stabilizer or a mixture of two or more stabilizers (e.g. a saccharide, such as e.g. α,α-trehalose dihydrate or sucrose, and optionally methionine as a second stabilizer), a nonionic surfactant and an effective amount of at least one hyaluronidase enzyme. Methods for preparing such formulations and their uses thereof are also provided.

4 Claims, 4 Drawing Sheets

(56) References Cited

U.S. PATENT DOCUMENTS

| | | |
|---|---|---|
| 5,945,098 A | 8/1999 | Sarno et al. |
| 6,171,586 B1 | 1/2001 | Lam et al. |
| 6,267,958 B1 | 7/2001 | Andya et al. |
| 6,627,196 B1 | 9/2003 | Baughman et al. |
| 6,632,979 B2 | 10/2003 | Erickson et al. |
| 6,685,940 B2 | 2/2004 | Andya et al. |
| 6,821,515 B1 | 11/2004 | Cleland et al. |
| 6,875,432 B2 | 4/2005 | Liu et al. |
| 6,949,245 B1 | 9/2005 | Sliwkowski |
| 6,991,790 B1 | 1/2006 | Lam et al. |
| 7,060,268 B2 | 6/2006 | Andya et al. |
| 7,371,379 B2 | 5/2008 | Baughman et al. |
| 7,449,184 B2 | 11/2008 | Allison et al. |
| 7,485,302 B2 | 2/2009 | Adams et al. |
| 7,498,030 B2 | 3/2009 | Adams et al. |
| 7,501,122 B2 | 3/2009 | Adams et al. |
| 7,537,931 B2 | 5/2009 | Adams et al. |
| 7,612,181 B2 | 11/2009 | Wu et al. |
| 7,618,631 B2 | 11/2009 | Sliwkowski |
| 7,666,413 B2 | 2/2010 | Liu et al. |
| 7,682,609 B2 | 3/2010 | Andya et al. |
| 7,767,429 B2 | 8/2010 | Bookbinder et al. |
| 7,829,081 B2 | 11/2010 | Bookbinder et al. |
| 7,846,431 B2 | 12/2010 | Bookbinder et al. |
| 7,846,441 B1 | 12/2010 | Hellmann |
| 7,862,817 B2 | 1/2011 | Adams et al. |
| 7,871,607 B2 | 1/2011 | Bookbinder et al. |
| 7,892,549 B2 | 2/2011 | Paton et al. |
| 7,993,834 B2 | 8/2011 | Mass |
| 8,075,892 B2 | 12/2011 | Hellmann et al. |
| 8,076,066 B2 | 12/2011 | Mass |
| 8,105,586 B2 | 1/2012 | Bookbinder et al. |
| 8,142,776 B2 | 3/2012 | Liu et al. |
| 8,163,287 B2 | 4/2012 | Sliwkowski et al. |
| 8,202,517 B2 | 6/2012 | Bookbinder et al. |
| 8,257,699 B2 | 9/2012 | Bookbinder et al. |
| 8,309,087 B2 | 11/2012 | Hellmann |
| 8,372,396 B2 | 2/2013 | Andya et al. |
| 8,404,234 B2 | 3/2013 | Allison et al. |
| 8,425,908 B2 | 4/2013 | Hellmann |
| 8,431,124 B2 | 4/2013 | Bookbinder et al. |
| 8,431,380 B2 | 4/2013 | Bookbinder et al. |
| 8,440,402 B2 | 5/2013 | Mass |
| 8,450,470 B2 | 5/2013 | Bookbinder et al. |
| 8,568,720 B2 | 10/2013 | Morichika et al. |
| 8,580,252 B2 | 11/2013 | Bookbinder et al. |
| 8,580,264 B2 | 11/2013 | Zhang et al. |
| 8,591,897 B2 | 11/2013 | Bryant |
| 8,592,152 B2 | 11/2013 | Mass |
| 8,597,654 B2 | 12/2013 | Bryant |
| 8,632,778 B2 | 1/2014 | Kakuta et al. |
| 8,642,036 B2 | 2/2014 | Hellmann |
| 8,652,474 B2 | 2/2014 | Harris et al. |
| 8,691,232 B2 | 4/2014 | Derynck et al. |
| 8,703,126 B2 | 4/2014 | Liu et al. |
| 8,758,747 B2 | 6/2014 | Kallmeyer et al. |
| 8,765,685 B2 | 7/2014 | Bookbinder et al. |
| 8,772,246 B2 | 7/2014 | Bookbinder et al. |
| 8,840,884 B2 | 9/2014 | Kakuta et al. |
| 8,921,527 B2 | 12/2014 | Mizushima et al. |
| 8,961,964 B2 | 2/2015 | Liu et al. |
| 9,017,671 B2 | 4/2015 | Andya et al. |
| 9,051,384 B2 | 6/2015 | Kakuta et al. |
| 9,084,777 B2 | 7/2015 | Morichika et al. |
| 9,180,189 B2 | 11/2015 | Andya et al. |
| 9,181,346 B2 | 11/2015 | Harris et al. |
| 9,211,315 B2 | 12/2015 | Bookbinder et al. |
| 9,283,273 B2 | 3/2016 | Andya et al. |
| 9,345,661 B2 | 5/2016 | Adler et al. |
| 9,539,263 B2 | 1/2017 | Zhang et al. |
| 9,562,223 B2 | 2/2017 | Bookbinder et al. |
| 9,677,061 B2 | 6/2017 | Bookbinder et al. |
| 9,677,062 B2 | 6/2017 | Bookbinder et al. |
| 9,750,752 B2 | 9/2017 | Zhang et al. |
| 9,815,904 B2 | 11/2017 | Gennaro et al. |
| 9,968,676 B2 | 5/2018 | Adler et al. |
| 9,969,811 B2 | 5/2018 | Gennaro et al. |
| 10,160,811 B2 | 12/2018 | Baughman et al. |
| 10,280,228 B2 | 5/2019 | Baughman et al. |
| 10,849,849 B2 | 12/2020 | Eng-Wong et al. |
| 11,077,189 B2 | 8/2021 | Benyunes et al. |
| 11,414,498 B2 | 8/2022 | Harris et al. |
| 11,597,776 B2 | 3/2023 | Harris et al. |
| 11,638,756 B2 | 5/2023 | Benyunes et al. |
| 11,654,105 B2 | 5/2023 | Eng-Wong et al. |
| 11,992,529 B2 | 5/2024 | Benyunes et al. |
| 12,110,341 B2 | 10/2024 | Harris et al. |
| 12,128,103 B2 | 10/2024 | Benyunes et al. |
| 12,145,998 B2 | 11/2024 | Gennaro et al. |
| 12,252,549 B2 | 3/2025 | Badovinac-Crnjevic et al. |
| 2001/0014326 A1 | 8/2001 | Andya et al. |
| 2002/0035736 A1 | 3/2002 | Erickson et al. |
| 2004/0197324 A1 | 10/2004 | Liu et al. |
| 2004/0268425 A1 | 12/2004 | Bookbinder et al. |
| 2005/0118163 A1 | 6/2005 | Mizushima et al. |
| 2005/0158303 A1 | 7/2005 | Liu et al. |
| 2005/0158316 A1 | 7/2005 | Lam et al. |
| 2005/0177100 A1 | 8/2005 | Harper et al. |
| 2006/0088523 A1 | 4/2006 | Andya et al. |
| 2006/0104968 A1 | 5/2006 | Bookbinder et al. |
| 2007/0020261 A1 | 1/2007 | Sliwkowski et al. |
| 2007/0053900 A1 | 3/2007 | Liu et al. |
| 2007/0071675 A1 | 3/2007 | Wu et al. |
| 2007/0086995 A1 | 4/2007 | Liu et al. |
| 2009/0123367 A1 | 5/2009 | Bookbinder et al. |
| 2009/0280129 A1 | 11/2009 | Liu et al. |
| 2010/0158898 A1 | 6/2010 | Liu et al. |
| 2010/0158899 A1 | 6/2010 | Andya et al. |
| 2011/0044977 A1 | 2/2011 | Adler et al. |
| 2011/0076273 A1 | 3/2011 | Adler et al. |
| 2011/0236383 A1 | 9/2011 | Andya et al. |
| 2013/0216532 A1 | 8/2013 | Adler et al. |
| 2013/0236448 A1 | 9/2013 | Kamerzell et al. |
| 2014/0005367 A1 | 1/2014 | Morichika et al. |
| 2014/0037613 A1 | 2/2014 | Bookbinder et al. |
| 2014/0056883 A1 | 2/2014 | Zhang et al. |
| 2015/0044198 A1 | 2/2015 | Liu et al. |
| 2015/0086537 A1 | 3/2015 | Adler et al. |
| 2015/0165059 A1 | 6/2015 | Bookbinder et al. |
| 2015/0196642 A1 | 7/2015 | Andya et al. |
| 2015/0225485 A1 | 8/2015 | Liu et al. |
| 2015/0284466 A1 | 10/2015 | Morichika et al. |
| 2016/0051640 A1 | 2/2016 | Bookbinder et al. |
| 2016/0090419 A1 | 3/2016 | Morichika et al. |
| 2016/0137742 A1 | 5/2016 | Adler et al. |
| 2016/0166689 A1 | 6/2016 | Adler et al. |
| 2016/0367675 A1 | 12/2016 | Liu et al. |
| 2017/0049888 A1 | 2/2017 | Liu et al. |
| 2023/0277663 A1 | 9/2023 | Ross et al. |
| 2023/0314420 A1 | 10/2023 | Avenal et al. |
| 2023/0416401 A1 | 12/2023 | Harris et al. |
| 2024/0207400 A1 | 6/2024 | Adler et al. |
| 2024/0269064 A1 | 8/2024 | Eng-Wong et al. |
| 2025/0018032 A1 | 1/2025 | Benyunes et al. |
| 2025/0084181 A1 | 3/2025 | Gennaro et al. |
| 2025/0090660 A1 | 3/2025 | Adler et al. |
| 2025/0177364 A1 | 6/2025 | Eiger et al. |

FOREIGN PATENT DOCUMENTS

| | | |
|---|---|---|
| CL | 2011-000561 A1 | 9/2011 |
| CN | 1191490 A | 8/1998 |
| CN | 101163717 A | 4/2008 |
| CN | 101370525 A | 2/2009 |
| EP | 0659439 B1 | 10/2001 |
| EP | 1331266 A1 | 7/2003 |
| EP | 1331266 A4 | 7/2003 |
| EP | 0590058 B1 | 11/2003 |
| EP | 1603541 B1 | 11/2009 |
| EP | 1516628 B1 | 8/2013 |
| EP | 2687202 A1 | 1/2014 |
| EP | 3785701 A1 | 3/2021 |
| EP | 2459167 B2 | 3/2022 |
| EP | 2687202 B1 | 5/2023 |

(56) References Cited

FOREIGN PATENT DOCUMENTS

| | | |
|---|---|---|
| EP | 4257150 A2 | 10/2023 |
| JP | 2007-533631 A | 11/2007 |
| JP | 2008-507520 A | 3/2008 |
| JP | 2008-520551 A | 6/2008 |
| JP | 2008-528638 A | 7/2008 |
| JP | 2009-504142 A | 2/2009 |
| KR | 10-2007-0068385 A1 | 6/2007 |
| WO | 93/21319 A1 | 10/1993 |
| WO | 94/00136 A1 | 1/1994 |
| WO | 96/40210 A1 | 12/1996 |
| WO | 97/004801 A1 | 2/1997 |
| WO | 98/22136 A2 | 5/1998 |
| WO | 98/43960 A1 | 10/1998 |
| WO | 98/50433 A1 | 11/1998 |
| WO | 99/009016 A1 | 2/1999 |
| WO | 99/057134 A1 | 11/1999 |
| WO | 01/00245 A2 | 1/2001 |
| WO | 01/00245 A3 | 1/2001 |
| WO | 2003/037992 A1 | 5/2003 |
| WO | 2004/078140 A2 | 9/2004 |
| WO | 2005/023328 A2 | 3/2005 |
| WO | 2005/037992 A2 | 4/2005 |
| WO | 2005/117986 A2 | 12/2005 |
| WO | 2006/044908 A2 | 4/2006 |
| WO | 2006/091871 A1 | 8/2006 |
| WO | 2007/024715 A2 | 3/2007 |
| WO | 2007/024715 A9 | 3/2007 |
| WO | 2007/109221 A2 | 9/2007 |
| WO | 2007/109221 A3 | 9/2007 |
| WO | 2008/150949 A1 | 12/2008 |
| WO | 2009/055343 A2 | 4/2009 |
| WO | 2009/080541 A1 | 7/2009 |
| WO | 2009/117085 A1 | 9/2009 |
| WO | 2010/029054 A1 | 3/2010 |
| WO | 2010/138918 A1 | 12/2010 |
| WO | 2011/012637 A1 | 2/2011 |

OTHER PUBLICATIONS

Annex A to Declaration of Prof Dr. Wolfgang Frieß, Curriculum Vitae of Prof. Dr. Wolfgang Frieß in Opposition to EP 2459167, dated Aug. 7, 2015 (1 page).
Annex B to Declaration of Prof Dr. Wolfgang Frieß, Opposition to EP 2459167, dated Aug. 7, 2015 (1 page).
Annex to the Grounds for the Decision upholding EP 2 459 167, Summary of the Oral Proceedings, dated Nov. 23, 2015 (7 pages).
Annex to the Summons to attend oral proceedings, Summary of Proceedings, in Opposition to EP 2 459 167 dated Apr. 24, 2015 (7 pages).
Arming, S. et al., "In vitro Mutagenesis of PH-20 Hyaluronidase from Human Sperm" Eur J Biochem 247(3):810-814 (Aug. 1, 1997).
Arteaga, C. L. et al., "p185c-erbB-2 Signaling Enhances Cisplatin-induced Cytotoxicity in Human Breast Carcinoma Cells: Association between an Oncogenic Receptor Tyrosine Kinase and Drug-induced DNA Repair" Cancer Res 54(14):3758-3765 (Jul. 15, 1994).
Aukland, K. et al., "Interstitial-Lymphatic Mechanisms in the Control of Extracellular Fluid Volume" Physiology Reviews 73(1):1-78 (Jan. 1, 1993).
Bacus, S. S. et al., "Differentiation of Cultured Human Breast Cancer Cells (AU-565 and MCF-7) Associated With Loss of Cell Surface HER-2/neu Antigen" Mol Carcinogen 3(6):350-362 ( 1990).
Bacus, S. S. et al., "Tumor-inhibitory Monoclonal Antibodies to the HER-2/Neu Receptor Induce Differentiation of Human Breast Cancer Cells" Cancer Res 52(9):2580-2589 (May 1, 1992).
Banga, Therapeutic peptides and proteins: formulation, processing, and delivery systems "Chapter 3, Stability of Therapeutic Peptides and Proteins" Boca Raton, FL:CRC press, Taylor & Francis Group,:67-89 ( 2006).

Baselga, J. et al., "Phase II Trial of Pertuzumab and Trastuzumab in Patients with Human Epidermal Growth Factor Receptor 2-Positive Metastatic Breast Cancer That Progressed During Prior Trastuzumab Therapy" J Clin Oncl 28(7):1138-1144 (Mar. 1, 2010).
Bertrand, P. et al., "Hyaluronan (Hyaluronic Acid) and Hyaluronectin in the Extracellular Matrix of Human Breast Carcinomas: Comparison Between Invasive and Non-Invasive Areas" Int J Cancer 52(1):1-6 (Aug. 19, 1992).
Bookbinder, L. et al., "A Recombinant Human Enzyme for Enhanced Interstitial Transport of Therapeutics" J Control Release 114(2):230-241 (Aug. 28, 2006).
Bywaters, E. G. L. et al., "Reconstitution of the Dermal Barrier to Dye Spread After Hyaluronidase Injection" Brit Med J 2(4741):1178-1183 (Nov. 17, 1951).
Calculations Lower Volume Herceptin Solutions, (European Patent Nos. EP 2 459 167 B2 (Adler et al., filed: Jul. 28, 2010, granted: Mar. 2, 2022)),:1-5.
Carpenter et al., "Overlooking Subvisible Particles In Therapeutic Protein Products: Gaps That May Compromise Product Quality" Journal of Pharmaceutical Sciences 98(4):1201-1205 (Apr. 2009).
Carpenter, J.F., et al., "Inhibition of stress-induced aggregation of protein therapeutics" Methods in Enzymology 309:236-255 ( 1999).
Cherr, G. N. et al., "The PH-20 Protein in Cynomolgus Macaque Spermatozoa: Identification of Two Different Forms Exhibiting Hyaluronidase Activity" Dev Biol 175(1):142-153 (Apr. 10, 1996).
Chi, E., et al., "Physical stability of proteins in aqueous solution: mechanism and driving forces in nonnative protein aggregation" Pharm Res 20(9):1325-1336 (Sep. 1, 2003).
Cleland et al., "Formulation and Delivery of Proteins and Peptides: Design and Development Strategies" ACS Symposium Series Chapter 1:1-19 ( 1994).
ClinicalTrials.gov, "A dose-finding study of subcutaneous Herceptin (trastuzumab) in healthy male volunteers and human epidermal growth factor receptor 2 (HER2)-positive females" ClinicalTrials.gov ID: NCT00800436, Version 7 (May 13, 2009), pp. 1-7, Retrieved Oct. 25, 2023.
CMC Biotech Working Group, "A-Mab: A Case Study in Bioprocess Development" Version 2.1: pp. 1-278 (Oct. 30, 2009).
Commission Decision, "Granting marketing authorisation for the medicinal product for human use 'Raptiva—Efalizumab' under Council Regulation (EEC) No. 2309/93" Commission of the European Communities:1-3 (Sep. 20, 2004).
Commission Decision, "Granting marketing authorisation under Council Regulation (EEC) No. 2309/93 for 'Xolair-Omalizumab', a medicinal product for human use" Commission of the European Communities:1-3 (Oct. 25, 2005).
Commission Decision, "Granting marketing authorisation under Regulation (EC) No. 726/2004 of the European Parliament and of the Council for 'Stelara-ustekinumab', a medicinal product for human use" Commission of the European Communities:1-3 (Jan. 16, 2009).
Commission Decision, "Granting the marketing authorization for the medicinal product for human use, 'Humira-Adalimumab'" Commission of the European Communities:1-4 (Sep. 8, 2003).
Commission Implementing Decision, "Amending the marketing authorisation granted by Decision C(2000)2539 for 'Herceptin-trastuzumab', a medicinal product for human use" Commission of the European Communities: 1-95 (Aug. 26, 2013).
"Committee for Medicinal Products for Human Use (CHMP) Assessment Report: Herceptin" Procedure No. EMEA/H/C/000278 European Medicines Agency:1-70 (Jun. 27, 2013).
Communication of the Board of Appeal, Appeal No. T0139/16-3.3.07 (European Patent No. EP 2 459 167 B1 (Adler et al., filed: Jul. 28, 2010, granted: May 15, 2013)),:1-17 (Dec. 11, 2018).
Crommelin et al. Pharmaceutical Biotechnology—An introduction for Pharmacists and Pharmaceutical Scientists "Appendix A" Second edition, Taylor & Francis,: p. 308 ( 2002).
Crommelin, Expert report of Prof. Dr. Daan J.A. Crommelin (European Patent Nos. EP 2 459 167 B2 (Adler et al., filed: Jul. 28, 2010, granted: Mar. 2, 2022) and EP 2 687 202 B1 (Adler et al., filed: Jul. 28, 2010, granted: May 10, 2023)),:1-11 (Sep. 16, 2024).
Crommelin, Resume Dr. Daan J.A. Crommelin:1-5 (Jul. 2024).

(56) References Cited

OTHER PUBLICATIONS

Danilkovitch-Miagkova, A. et al., "Hyaluronidase 2 Negatively Regulates RON Receptor Tyrosine Kinase and Mediates Transformation of Epithelial Cells by Jaagsiekte Sheep Retrovirus" PNAS USA 100(8):4580-4585 (Apr. 15, 2003).
Daugherty et al., "Formulation and delivery issues for monoclonal antibody therapeutics" Advanced drug delivery reviews 58:686-706 ( 2006).
De Lange, Netherlands Patent Office Preliminary Dismissal Summary of Product Characteristics Halozyme (Rituximab) (Original document in Dutch, English machine translation included, 4 pages), (Jan. 12, 2022).
De Lange, Netherlands Patent Office Preliminary Opinion Summary of Product Characteristics Hyaluronidase (Original document in Dutch, 2 pages), (Dec. 6, 2016).
Decision of Opposition Division Stating that EP 2 459 167 is upheld, dated Oct. 19, 2015 (1 page).
Declaration of Dr. Michael Adler—Annex A to Declaration of Dr. Michael Adler, in Opposition to EP 2 459 167 dated Aug. 17, 2015, Curriculum Vitae of Dr. Michael Adler (1 page).
Declaration of Dr. Michael Adler in Opposition to EP 2 459 167 dated Aug. 17, 2015 (9 pages).
Declaration of Prof. Dr. Wolfgang Fries—Annex B, Opposition to EP 2 459 167, dated Aug. 7, 2015 (1 page).
Declaration of Prof. Dr. Wolfgang Frieß—Annex A , Curriculum Vitae of Prof. Dr. Wolfgang Frieß in Opposition to EP 2 459 167, dated Aug. 7, 2015 (1 page).
Declaration of Prof. Dr. Wolfgang Frieß submitted in Opposition to EP 2 459 167 B1-B2, dated Aug. 7, 2015 (11 pages).
Declaration of Prof. Dr. Wolfgang Frieß submitted in Opposition to EP 2 459 167 B1-B2, dated Aug. 7, 2015, including Exhibits 1-5 and Annexes A-B, pp. 1-52.
Drug Bank ,Trastuzumab Aug. 28, 2000 Accession No. DB00072 (BTD00098, BI0D00098 Which indicates using Trastuzumab as an injection solution for using subcutaneously in breast cancer. https://www.drugbank.ca/drugs/DB00072.
Erikson et al., "The Impact of Enzymatic Degradation on the Uptake of Differently Sized Therapeutic Molecules" Anticancer Research 28:3557-3566 ( 2008).
Eriksson et al. Design of experiments: Principles and applications "Fractional Factorial Designs" (4 pages), Revised and enlarged edition, Third edition, Sweden: Umetrics Academy, ( 2008).
Eriksson et al. Design of experiments: Principles and applications "Preface" (7 pages), Revised and enlarged edition, Third edition, Sweden:Umetrics Academy, ( 2008).
Eriksson et al. Design of experiments: Principles and applications "Computation of effects using least squares fit" (6 pages), Revised and enlarged edition, Third edition, Sweden:Umetrics Academy, ( 2008).
Eriksson et al. Design of experiments: Principles and applications "Basic principles of DOE" (8 pages), Revised and enlarged edition, Third edition, Sweden:Umetrics Academy, ( 2008).
European Pharmacopoeia, 6th Edition: pp. 1097-1098, 1554-1556, 2050-2051 (Jul. 16, 2007).
Evers et al., "Long-term stability prediction for developability assessment of biopharmaceutics using advanced kinetic modeling" Pharmaceutics 14:375 (pp. 1-17) (Feb. 8, 2022).
"'ExPASy' on the basis of the light and heavy chain amino acid sequences of the hyaluronidase enzyme (rhuPH20)" Swiss Institute of Bioinformatics (1 page), http://web.expasy.org/compute_pi/.
"'ExPASy' on the basis of the light and heavy chain amino acid sequences of the anti-HER2 antibody Trastuzumab" Swiss Institute of Bioinformatics (1 page), http://web.expasy.org/compute_pi/.
F. Hoffmann-Laroche, AG, "European Patent Application No. 09167025. 7" (Priority Document filed Jul. 31, 2009),:1-59 (Jul. 31, 2009).
Facts and Arguments by Harrison Goddard Foote LLP in Opposition to EP 2 459 167 dated Jan. 14, 2014 (24 pages).
Fradkin et al., "Immunogenicity of Aggregates of Recombinant Human Growth Hormone in Mouse Models" Journal of Pharmaceutical Sciences 98(9):3247-3264 (Sep. 2009).
Franklin, M.C., et al., "Insights into ErbB signaling from the structure of the ErbB2-pertuzumab complex" Cancer Cell 5(4):317-328 (Apr. 1, 2004).
Frieß, Resume Dr. Wolfgang Frieß, Annex A and B (Annex A: Short Curriculum Vitae—Education and Experience; Annex B: Cited Exhibits and Documents cited in the Opposition Procedure, 2 pages), (Aug. 7, 2015).
Frijlink, Comments of Prof. Dr. Henderik W. Frijlink on the publication of Yocum et al.,, "Clinical Trial of Recombinant Human PH20 Hyaluronidase's Effect on Subcutaneous Absorption and Pharmacokinetics of a Large Protein Molecule Therapeutic, 34th Annual Meeting and Exposition of the Controlled Release Society 2007, (pp. 10-11)":1-11 (Nov. 25, 2024).
Frijlink, Dr. Henderik W. Frijlink Resume One Page Summary & Extended Curriculum:1-38 (Sep. 17, 2024).
Frijlink, "Expert Declaration of Prof. Dr. Henderik W. Frijlink" (European Patent No. EP 2 687 202 B1 (Adler et al., filed: Jul. 28, 2010, granted: May 10, 2023)),:1-20 (Oct. 25, 2024).
Frijlink, Expert declaration of Prof. Dr. Henderik W. Frijlink (European Patent Nos. EP 2 459 167 B2 (Adler et al., filed: Jul. 28, 2010, granted: Mar. 2, 2022) and EP 2 687 202 B1 (Adler et al., filed: Jul. 28, 2010, granted: May 10, 2023)),:1-16 (Sep. 17, 2024).
Frost, G. I. et al., "A microtiter-based assay for hyaluronidase activity not requiring specialized reagents" Anal Biochem 251(2):263-269 (Sep. 5, 1997).
Frost, G. I. et al., "Purification, Cloning, and Expression of Human Plasma Hyaluronidase" Biochem Bioph Res Co 236(1):10-15 (Jul. 9, 1997).
Frost, G. I.,, "Recombinant Human Hyaluronidase (rHuPH20): an Enabling Platform for Subcutaneous Drug and Fluid Administration" Expert Opin Drug Del 4(4):427-440 (Jul. 1, 2007).
Fuguet et al., "Critical micelle concentration of surfactants in aqueous buffered and unbuffered systems" Analytica Chimica Acta 548:95-100 ( 2005).
Galush, W., et al., "Viscosity Behavior of High-Concentration Protein Mixtures" J Pharm Sci 101(3):1012-1020 (Mar. 1, 2012).
Gatlin et al. Injectable drug development: techniques to reduce pain and irritation "Formulation and administration techniques to minimize injection pain and tissue damage associated with parenteral products" Denver, CO:Interpharm Press,:401-421 ( 1999).
Genatrika et al., "Personnel knowledge of intravenous admixtures: a survey in a government hospital" Pan African Medical Journal 40(198):1-9 (Dec. 3, 2021).
Genentech, Inc. et al., "Declaration of Prof. Dr. Wolfgang Frieß under 37 C.F.R. 1.132":1-89 (Jun. 11, 2015).
Genentech, Inc., et al., "Herceptin (Trastuzumab)—Package Insert":1-28 (Sep. 26, 2003).
Gligorov, J., et al., "Safety and tolerability of subcutaneous trastuzumab for the adjuvant treatment of human epidermal growth factor receptor 2-positive early breast cancer: SafeHer phase III study's primary analysis of 2573 patients" Eur J Cancer 82:237-246 (Sep. 1, 2017).
Grillo et al., "Characterizing the formulation design space" BioPharm International:30, 32, 34-36, 38-39 (Mar. 2010).
Grounds for the Decision upholding EP 2 459 167, dated Nov. 23, 2015 (18 pages).
Guidance for Industry, "Q8(R2) Pharmaceutical Development" U.S. Department of Health and Human Services Food and Drug Administration, Center for Drug Evaluation and Research (CDER) & Center for Biologics Evaluation and Research (CBER) ICH, Revision 2:1-29 (Nov. 2009).
Haller, "Converting intravenous dosing to subcutaneous dosing with recombinant human hyaluronidase" Pharmaceutical Technology 31(10):1-5 (Oct. 2, 2007).
"Halozyme and Roche enter agreement for the application of Enhanze, a novel technology to improve drug delivery" Halozyme Therapeutics Inc. Press Release:1-4 (Dec. 5, 2006).
"Halozyme Announces Roche Doses First Patient in Phase 3 Clinical Trial with Subcutaneous Herceptin(R)" Halozyme Therapeutics, Inc. Press Release (Retrieved May 7, 2023),:1-3 (Oct. 22, 2009).

(56) References Cited

OTHER PUBLICATIONS

"Halozyme Therapeutics Announces Roche Begins Phase 1 Clinical Trial and SelectsFourth Exclusive Biologic Target" Press Release:1-3 (Dec. 8, 2008).
"Halozyme Therapeutics" Company Overview, Slides, pp. 1-30 ( Feb. 2007).
"Halozyme Therapeutics, Matrix Therapies for Life" (Retrieved May 7, 2023) Jefferies Investor Presentation, New York, pp. 1-31 ( Jun. 17, 2009).
"Halozyme Therapeutics' Enhanze Technology Large Protein Molecule Therapeutic Clinical Trial Results Presented at the 34th Annual Meeting of the Controlled Release Society" News Article:1-2 (Jul. 9, 2007) https://ir.halozyme.com/news/news-details/2007/Halozyme-Therapeutics-Enhanze-Technology-Large-Protein-Molecule-Therapeutic-Clinical-Trial-Results-Presented-at-the-34th-Annual-Meeting-of-the-Controlled-Release-Society-2007-7-9/default.aspx.
Hamberger et al., "Influence of size and functionality of polymeric nanoparticles on the adsorption behavior of sodium dodecyl sulfate as detected by isothermal titration calorimetry" Colloid and Polymer Science 289:3-14 ( 2011).
Hancock, M. C. et al., "A Monoclonal Antibody Against the c-erbB-2 Protein Enhances the Cytotoxicity of cis-Diamminedichloroplatinum Against Human Breast and Ovarian Tumor Cell Lines" Cancer Res 51(17):4575-4580 (Sep. 1, 1991).
Handbook of Pharmaceutical Excipients "Methionine Extract (436-437)" Rowe, Raymond C., et al., 6th edition,Pharmaceutical Press,:1-6 ( 2009).
Handbook of Pharmaceutical Excipients Rowe, Raymond C., et al., 6th edition,Pharmaceutical Press,: pp. 549-553, 637-640, 703-707, 746-747 ( 2009).
Harlow, E., et al. Antibodies, A Laboratory Manual Cold Spring Harbor, N.Y.:Cold Spring Harbor [CSH], (1988).
Harris, E.N., et al., "Endocytic Function, Glycosaminoglycan Specificity, and Antibody Sensitivity of the Recombinant Human 190-kDa Hyaluronan Receptor for Endocytosis (HARE)" J Biol Chem 279(35):36201-36209 (Aug. 27, 2004).
Harris, R.J.,, "Identification of multiple sources of charge heterogeneity in a recombinant antibody" J Chromatogr B Biomed Sci Appl 752(2):233-245 (Mar. 10, 2001).
Harwerth, I. et al., "Monoclonal Antibodies Against the Extracellular Domain of the erbB-2 Receptor Function as Partial Ligand Agonists" J Biol Chem 267(21):15160-15167 (Jul. 25, 1992).
Herceptin FDA Prescribing Information, U.S. BL 103792/5175 Amendment: Trastuzumab-Genentech, Inc.:1-11 (Jan. 18, 2008).
Herceptin product information, Aug. 28, 2000 (in German) (31 pages) ( Aug. 28, 2000).
Herceptin, European Public Assessment Report, Scientific Discussion:1-42 (Nov. 30, 2004).
Herceptin, Summary of Product Characteristics (Original document in Dutch, English machine translation included, 194 pages), (Aug. 26, 2013).
Herceptin, Summary of Product Characteristics (Original document in Dutch, 14 pages), (Mar. 12, 2001).
Herceptin, Summary of Product Characteristics:1-38 ( 2008).
"Home administration of trastuzumab by subcutaneous injection" Imperial College Healthcare NHS Trust:1-8 (Jun. 2022).
Hoppe, "Letter from Accord to Roche Regarding the German part of EP 2 687 202 B1—Subcutaneous Anti-HER2 Antibody Formulation" Preu Bohlig & Partner (Original (German) and English translation provided, 4 pages), (Nov. 13, 2023).
Huelsmeyer et al., "A universal tool for stability predictions of biotherapeutics, vaccines and in vitro diagnostic products" Scientific Reports 13:10077 (pp. 1-13) ( 2023).
Hylenex et al., CAS Registry Database, 757971-58-7, 36-482 (Hyaluronoglucosaminidase PH20 (human)), pp. 1 2010.
Hylenex recombinant (hyaluronidase human injection) Prescribing Information, pp. 1-6 ( Oct. 2008).

ICH Harmonised Tripartite Guidelines—Q1A(R2), Q1C, Q5C Q6A, Q6B, International Conference on Harmonisation of Technical Requirements for Registration of Pharmaceuticals for Human Use:91 pages ( 1993-2003).
"International Search Report—PCT/EP2010/060930" (w/Written Opinion),: pp. 1-14 (Jul. 8, 2011).
Ismael, G., et al., "Subcutaneous versus intravenous administration of (neo)adjuvant trastuzumab in patients with HER2-positive, clinical stage I-III breast cancer (HannaH study): a phase 3, open-label, multicentre, randomised trial" Lancet Oncol 13(9):869-878 (Sep. 1, 2012).
"Isoelectric Focusing (IEF) of rHuPH20 recombinant hyaluronidase" (3 pages), (Aug. 7, 2015).
Ji et al., "Methionine, tryptophan, and histidine oxidation in a model protein, PTH: mechanisms and stabilization" Journal of Pharmaceutical Sciences 98(12):4485-4500 (Dec. 2009).
Jiang, P., et al., "Effects of recombinant human PH20 (rHuPH20) on interstitial matrices: creating a favorable environment for the delivery of cytostatic agents" Cancer Res (abstract 5075), 65( Suppl 9):1-2 (May 1, 2005).
Jiskoot et al., "Ongoing challenges to develop high concentration monoclonal antibody-based formulations for subcutaneous administration: Quo Vadis?" Journal of Pharmaceutical Sciences 00:1-7 (Dec. 2001).
Jones, A.,, "Analysis of Polypeptides and Proteins" Adv Drug Delivery Rev 10(1):29-90 (Jan. 1, 1993).
Kasprzyk, P. G. et al., "Therapy of an Animal Model of Human Gastric Cancer Using a Combination of Anti-erbB-2 Monoclonal Antibodies" Cancer Res 52(10):2771-2776 (May 15, 1992).
Khan, T., et al., "Key interactions of surfactants in therapeutic protein formulations: A review" Eur J Pharma Biopharm 97( Suppl Pt.A):60-67 (Oct. 3, 2015).
Kiese, S. et al., "Shaken, Not Stirred: Mechanical Stress Testing of an IgG1 Antibody" J Pharm Sci 97(10):4347-4366 (Oct. 1, 2008).
Kimata, K. et al., "Increased Synthesis of Hyaluronic Acid by Mouse Mammary Carcinoma Cell Variants with High Metastatic Potential" Cancer Res 43(3):1347-1354 (Mar. 1, 1983).
Kipriyanov Methods in Molecular Biology, Recombinant Antibodies for Cancer Therapy: Methods and Protocols "Generation of antibody molecules through antibody engineering" vol. 207:3-25 ( 2003).
Klapper, L., et al., "A Subclass of Tumor-Inhibitory Monoclonal Antibodies to ErbB-2/HER2 Blocks Crosstalk With Growth Factor Receptors" Oncogene 14(17):2099-2109 (May 1, 1997).
Knudson, C. B. et al., "Hyaluronan-binding proteins in development, tissue homeostasis, and disease" FASEB J 7(13):1233-1241 (Oct. 1, 1993).
Kretsinger et al., "Expectations for Phase-Appropriate Drug Substance and Drug Product Specifications for Early-Stage Protein Therapeutics" Journal of Pharmaceutical Sciences, vol. xxx, vol. 108:1-11 ( 2019).
Krishnan, S., et al. Formulation and Process Development Strategies for Manufacturing Biopharmaceuticals "Chapter 16: Development of Formulations for Therapeutic Monoclonal Antibodies and Fc Fusion Proteins" Jameel, F. and Hershenson, S., eds, Hoboken, New Jersey-US:John Wiley & Sons, Inc.,:383-427 ( 2010).
Kuzman et al., "Long-term stability predictions of therapeutic monoclonal antibodies in solution using Arrhenius-based kinetics" Scientific Reports 11:20534 (pp. 1-15) ( 2021).
Lalancette, C., et al., "Characterization of an 80-Kilodalton Bull Sperm Protein Identified as PH-20" Biol Reprod 65(2):628-636 (Aug. 1, 2001).
Lam, X., et al., "Antioxidants for Prevention of Methionine Oxidation in Recombinant Monoclonal Antibody HER2" J Pharm Sci 86(11):1250-1255 (Nov. 1, 1997).
Laurent, T. C. et al., "Hyaluronan" FASEB J 6(7):2397-2404 (Apr. 1, 1992).
Laurent, T.C., et al. Degradation of Bioactive Substances: Physiology and Pathophysiology "Chapter 16: Catabolism of Hyaluronan" J.H. Henriksen, Boca Raton, FL:CRC Press,:249-265 ( 1991).
Laurent, U. B., et al., "Catabolismof Hyaluronan in Rabbit Skin Takes Place Locally, In Lymph Nodes and Liver" Exp Physiol 76(5):695-703 (Sep. 1, 1991).

(56) References Cited

OTHER PUBLICATIONS

Laursen et al., "Pain Perception after Subcutaneous Injections of Media Containing Different Buffers" Basic & clinical pharmacology & toxicology 98:218-221 ( 2006).

Leyland-Jones et al., "Pharmacologic insights into the future of trastuzumab (with French translation)" Annals of Oncology 12((Suppl. 1)):S43-S47 ( 2001).

Lim, Jonathan M.D., President and CEO, "Halozyme Therapeutics, Matrix Therapies for Life" (Retrieved May 7, 2023) 28th J.P. Morgan Healthcare Annual Conference, San Francisco, pp. 1-42 ( Jan. 13, 2010).

Mahler et al., "Induction and analysis of aggregates in a liquid IgG1-antibody formulation" European Journal of Pharmaceutics and Biopharmaceutics 59:407-417 ( 2005).

Mahler et al., "Surface activity of a monoclonal antibody" Journal of pharmaceutical sciences 98(12):4525-4533 (Dec. 2009).

Maier, L. A. et al., "Requirements for the Internalization of a Murine Monoclonal Antibody Directed against the HER-2/neu Gene Product c-erbB-2" Cancer Res 51(19):5361-5369 (Oct. 1, 1991).

Mandenius et al., "Bioprocess optimization using design-of-experiments methodology" Biotechnology progress 24:1191-1203 (Nov. 24, 2008).

Manning et al., "Stability of Protein Pharmaceuticals" Pharm. Res. 6(11):903-918 ( 1989).

McKenzie, S. J. et al., "Generation and Characterization of Monoclonal Antibodies Specific for the Human neu Oncogene Product, p185" Oncogene 4(5):543-548 (May 1, 1989).

McNally et al. Protein Formulation and Delivery "Preformulation Development of Protein Drugs" 2nd edition, New York, NY:Informa Healthcare USA, Inc., vol. 175:109-111 ( 2008).

Melamed, I.R., et al., "Recombinant Human Hyaluronidase Facilitates Dispersion of Subcutaneously Administered Gammagard Liquid and Enables Administration of a Full Monthly Dose in a Single Site to Patients with Immunodeficiency Diseases" J Allergy Clin Immunol 121(2 Suppl 1):S83 (Feb. 1, 2008).

Mieczkowski et al., "The Evolution of Commercial Antibody Formulations" Journal of Pharmaceutical Sciences 112:1801-1810 ( 2023).

Misbah et al., "Subcutaneous immunoglobulin: opportunities and outlook (with French translation)" Clinical & Experimental Immunology 158 (Suppl. 1):51-59 ( 2009).

Molar Weight of Different Excipients for Conversion of Units for Comparison of Quantity of Individual Excipients in Publications, (Original document in Dutch, English machine translation included (8 pages)).

Morar-Mitrica et al., "An intercompany perspective on biopharmaceutical drug product robustness studies" Journal of Pharmaceutical Sciences 107:529-542 (Feb. 1, 2018).

Morrow, L., et al., "Addition of Human Hyaluronidase to Rapid Analog Insulin Reduces the Absolute Variability of Early Insulin Absorption across Infusion Set Life" (Poster 27-LB and Abstract 27-LB) American Diabetes Association (ADA) 71st Scientific Sessions, Jun. 24-28, 2011, pp. LB8 (2011).

Nahta, R et al., "The HER-2-targeting antibodies trastuzumab and pertuzumab synergistically inhibit the survival of breast cancer cells" Cancer Res 64(7):2343-2346 (Apr. 1, 2004).

National Cancer Institute et al., "Trastuzumab information and collection of links to use of this drug, research results, and ongoing clinical trials" (Trastuzumab is approved to be used alone or with other drugs to treat: 1) Adenocarcinoma of the stomach or gastroesophageal junction. It is used for HER2 positive (HER2+) disease that has metastasized (spread to other parts of the body) in patients who have not already been treated for metastatic cancer. 2) Breast cancer that is HER2+), (May 10.

Nayar, Declaration of Dr. Rajiv Nayar (European Patent No. EP 2 687 202 B1 (Adler et al., filed: Jul. 28, 2010, granted: May 10, 2023)),:1-671 (Feb. 6, 2024).

Nayar, Declaration of Dr. Rajiv Nayar (European Patent Nos. EP 2 459 167 B2 (Adler et al., filed: Jul. 28, 2010, granted: Mar. 2, 2022) and EP 2 687 202 B1 (Adler et al., filed: Jul. 28, 2010, granted: May 10, 2023)),:1-29 (Dec. 5, 2023).

Nayar, Dr. Rajiv Nayar List of Annexes and Resume:1-18 (Dec. 5, 2023).

Notice of Opposition by Harrison Goddard Foote LLP to EP 2 459 167 dated Jan. 14, 2014 (5 pages).

Opponent's Further Response to the Summons to attend oral proceedings in Opposition to EP 2 459 167 dated Oct. 2, 2015 (1 page).

Opponent's Observations made in response to Proprietor's Reply in Opposition to EP 2 459 167 dated Feb. 19, 2015 (24 pages).

Opponent's Response to the Summons to attend oral proceedings in Opposition to EP 2 459 167 dated Aug. 18, 2015 (6 pages).

Original US product labelling for the IV formulation of Herceptin,:1-2 (Sep. 25, 1998).

Ozzello, L. et al., "Growth-promoting Activity of Acid Mucopolysaccharides on a Strain of Human Mammary Carcinoma Cells" Cancer Res 20:600-604 (Jun. 1, 1960).

Package leaflet, 'Herceptin® 600 ng/5 ml Injektionslosung', Feb. 2014 (in German) (6 pages) ( Feb. 2014).

Pearlman, R. et al. Peptide and Protein Drug Delivery "Chapter 6—Analysis of Protein Drugs" Lee, V. , ed., New York, N.Y.—US:Marcel Dekker, Inc.,:247-301 ( 1991).

Peng et al., "Effect of route of administration of human recombinant factor VIII on its immunogenicity in Hemophilia A mice" Journal of Pharmaceutical Sciences 98(12):4480-4484 (Dec. 2009).

Pertuzumab, Summary of Product Characteristics:1-43 (Dec. 8, 2017).

Phelps, B. M. et al., "Restricted Lateral Diffusion of PH-20, a PI-Anchored Sperm Membrane Protein" Science 240(4860):1780-1782 (Jun. 24, 1988).

Pirrello, R., et al., "Initial experiences with subcutaneous recombinant human hyaluronidase" J Palliat Med 10(4):861-864 (Aug. 1, 2007).

Pivot, X., et al., "Preference for subcutaneous or intravenous administration of trastuzumab in patients with HER2-positive early breast cancer (PrefHer): an open-label randomised study" Lancet Oncol 14:962-970 (Sep. 1, 2013).

Porter, "Human Immune Response to Recombinant Human Proteins" Journal of Pharmaceutical Sciences 90(1):1-11 (Jan. 2001).

Pre-Grant Opposition filed by Indian Pharmaceutical Alliance against Indian Patent Application No. 961/CHENP/2012, with Exhibits, dated Jan. 24, 2014 (82 pages).

Proprietor's Further Response to the Summons to attend oral proceedings in Opposition to EP 2 459 167 dated Oct. 1, 2015 (9 pages).

Proprietor's Reply to Opposition to EP 2 459 167 dated Sep. 30, 2014 (33 pages).

Proprietor's Response to the Summons to attend oral proceedings in Opposition to EP 2 459 167 dated Aug. 19, 2015 (34 pages).

Ratner, M., "Roche plans for more convenient-to-use Herceptin and Rituxan" Nat Biotechnol 28(4):298-298 (Apr. 1, 2010).

Ravuri, Declaration of Dr. Kishore Ravuri (European Patent No. EP 2 687 202 B1 (Adler et al., filed: Jul. 28, 2010, granted: May 10, 2023)),:1-6 (Jun. 21, 2024).

Ravuri, Declaration of Dr. Kishore Ravuri (European Patent Nos. EP 2 459 167 B2 (Adler et al., filed: Jul. 28, 2010, granted: Mar. 2, 2022) and EP 2 687 202 B1 (Adler et al., filed: Jul. 28, 2010, granted: May 10, 2023)),:1-4 (Jun. 21, 2024).

Ravuri, K. Challenges in Protein Product Development—Part II—Challenges with Excipients "Chapter 2: Polysorbate Degradation and Quality" Warne, N. & Mahler, H., eds., Cham, Switzerland: Springer—AAPS Advances in Pharmaceutical Sciences, vol. 38:25-62 (Jun. 20, 2018).

Ravuri, Resume Dr. Kishore Ravuri:1-2 (Jun. 21, 2024).

Reply to Communication pursuant to Rule 79(1) EPC, (European Patent No. EP 2 459 167 B1 (Adler et al., filed: Jul. 28, 2010, granted: May 15, 2013)),:1-33 (Sep. 30, 2014).

(56) References Cited

OTHER PUBLICATIONS

Riedl et al., "Subcutaneous administration of human C1 inhibitor with recombinant human hyaluronidase in patients with hereditary angioedema" Allergy and Asthma Proceedings 37(6):489-500 ( Nov.-Dec. 2016).

Roskos, L. K. et al., "The clinical pharmacology of therapeutic monoclonal antibodies" Drug Develop Res 61(3):108-120 (Jul. 19, 2004).

Safety Data Sheet for Herceptin s.c. 120 mg/ml, Aug. 29, 2013 (6 pages).

Saluja et al., "Nature and consequences of protein-protein interactions in high protein concentration solutions" International Journal of Pharmaceutics 358:1-15 ( 2008).

Schellekens, H.,, "Factors influencing the immunogenicity of therapeutic proteins" Nephrol Dial Transplant 20( Suppl 6):vi3-vi9 (Jun. 1, 2005).

Schmidt, "What is the significance of Design of Experiments (DOE) in the FDA/GMP-regulated environment?" GMP Navigator (Original document German, English machine translation included; 2 pages), (Feb. 23, 2009) https://www.gmp-navigator.com/gmpnews/welche-bedeutung-hat-design-of-experiments-doe-im-fda-gmpregulierten-umfeld.

Schwartzman et al., "Does route of administration affect the outcome of TNF antagonist therapy?" Arthritis Research & Therapy 6( Suppl 2):S19-S23 (Jun. 21, 2004).

Scientific Discussion European Public Assessment Report for Humira® (adalimumab):1-25 ( 2004).

Shawver, L. K. et al., "Ligand-Like Effects Induced by Anti-c-erbB-2 Antibodies Do Not Correlate with and Are Not Required for Growth Inhibition of Human Carcinoma Cells" Cancer Res 54(5):1367-1373 (Mar. 1, 1994).

Shekhar, C.,, "The Matrix Reloaded: Halozyme's Recombinant Enzyme Helps Injected Drugs Spread Faster" Chem Biol 14(6):603-604 (Jun. 1, 2007).

Shen et al., "The application of tert-butylhydroperoxide oxidation to study sites of potential methionine oxidation in a recombinant antibody" Techniques in protein chemistry VII, Academic Press:275-284 ( 1996).

Shire, "2005 AAPS Biotechnology Conference Open Forum on Aggregation of Protein Therapeutics—Panel Discussion Jun. 5-8, 2005 San Francisco, CA" The AAPS Journal 8(4, Article 73):E644-E654 (Oct. 13, 2006).

Shire, "Formulation and manufacturability of biologics" Current opinion in biotechnology 20:708-714 ( 2009).

Shire, S., et al., "Challenges in the Development of High Protein Concentration Formulations" J Pharm Sci 93(6):1390-1402 (Jun. 1, 2004).

Shpilberg, O., et al., "Subcutaneous administration of rituximab (MabThera) and trastuzumab (Herceptin) using hyaluronidase" Br J Cancer 109(6):1556-1561 (Sep. 17, 2013).

Singh, "Sucrose and trehalose in therapeutic protein formulations" Challenges in protein product development, AAPS Advances in the Pharmaceutical Sciences Series 38:63-95 ( 2018).

Stancovski, I. et al., "Mechanistic aspects of the opposing effects of monoclonal antibodies to the ERBB2 receptor on tumor growth" PNAS USA 88(19):8691-8695 (Oct. 1, 1991).

Statement of Defense of Roche in Dutch Proceedings (Conclusion of Answer), (European Patent No. EP 2 459 167 B2 (Adler et al., filed: Jul. 28, 2010, granted: Mar. 2, 2022), Original document in Dutch, English machine translation included (128 pages)), (Sep. 18, 2024).

Strickley et al., "A review of formulations of commercially available antibodies" Journal of Pharmaceutical Sciences 110:2590-2608 ( 2021).

Summons to attend oral proceedings in Opposition to EP 2 459 167 dated Apr. 24, 2015 (1 page).

Supersaxo, A., et al., "Effect of Molecular Weight on the Lymphatic Absorption of Water-Soluble Compounds Following Subcutaneous Administration" Pharm Res 7(2):167-169 (Feb. 1, 1990).

Swartz, M.,, "The Physiology of the Lymphatic System" Adv Drug Deliver Rev 50(1-2):3-20 (Aug. 23, 2001).

Tagliabue, E. et al., "Selection of monoclonal antibodies which induce internalization and phosphorylation of p185HER2 and growth inhibition of cells with HER2/NEU gene amplification" Int J Cancer 47(6):933-937 (Apr. 1, 1991).

Takeuchi, J. et al., "Variation in Glycosaminoglycan Components of Breast Tumors" Cancer Res 36(7 Suppl Part 1):2133-2139 (Jul. 1, 1976).

Tammi, R., et al., "Degradation of Newly Synthesized High Molecular Mass Hyaluronan in the Epidermal and Dermal Compartments of Human Skin in Organ Culture" J Invest Dermatol 97(1):126-130 (Jul. 1, 1991).

Technical Background Document, European Patent No. EP 2 459 167 B2 (Adler et al., filed: Jul. 28, 2010, granted: Mar. 2, 2022) (Original document in Dutch, English machine translation included (28 pages)).

Technical Background Document, European Patent No. EP 2 459 167 B2 (Adler et al., filed: Jul. 28, 2010, granted: Mar. 2, 2022) (Original document in Dutch, English machine translation included (30 pages)).

Technical Background Document, European Patent No. EP 2 687 202 B1 (Adler et al., filed: Jul. 28, 2010, granted: May 10, 2023) (Original document in Dutch, English machine translation included (31 pages)).

Toole, B., Cell Biology of Extracellular Matrix "Chapter 9: Proteoglycans and Hyaluronan in Morphogenesis and Differentiation" Elizabeth D. Hay, 2nd edition, New York:Plenum Press,:305-341 (Jan. 1, 1991).

U.S. Department of Health and Human Services, Public Health Assessment Guidance Manual (Update) Section 7.3.1.4 (excerpt):1-5 (Jan. 2005).

U.S. Food and Drug Administration Approval to Manufacture Cimzia, Department of Health & Human Services:1-10 (Apr. 22, 2008).

U.S. Food and Drug Administration Approval to Manufacture Ilaris, Department of Health & Human Services:1-8 (Jun. 17, 2009).

U.S. Food and Drug Administration Approval to Manufacture Simponi, Department of Health & Human Services:1-8 (Apr. 24, 2009).

Valabrega et al., "Trastuzumab: mechanism of action, resistance and future perspectives in HER2-overexpressing breast cancer" Annals of Oncology 18:977-984 ( 2007).

"ViroPharma Provides Update on Phase 2 Clinical Evaluation of Subcutaneous Cinryze® (C1 esterase inhibitor [human]) with Recombinant Human Hyaluronidase (rHuPH20)" Fierce Pharma Biopharma News & Insights:1-2 (Aug. 1, 2012).

Vromans, Expert Declaration of Prof. Dr. Herman Vromans (European Patent Nos. EP 2 459 167 B2 (Adler et al., filed: Jul. 28, 2010, granted: Mar. 2, 2022) and EP 2 687 202 B1 (Adler et al., filed: Jul. 28, 2010, granted: May 10, 2023)),:1-17 (Jul. 5, 2024).

Vromans, Resume Dr. Herman Vromans with List of Annexes:1-12 (Jul. 5, 2024).

Walshe, J., et al., "A Phase II Trial with Trastuzumab and Pertuzumab in Patients with HER2-Overexpressed Locally Advanced and Metastatic Breast Cancer" Clin Breast Cancer 6(6):535-539 (Feb. 1, 2006).

Wang et al., "Antibody structure, instability, and formulation" Journal of Pharmaceutical Sciences 96(1):1-26 (Jan. 2007).

Wang et al., "Stabilizing two IgG1 monoclonal antibodies by surfactants: balance between aggregation prevention and structure perturbation" European Journal of Pharmaceutics and Biopharmaceutics 114:263-277 ( 2017).

Warne, "Development of high concentration protein biopharmaceuticals: the use of platform approaches in formulation development" European journal of pharmaceutics and biopharmaceutics 78:208-212 ( 2011).

Weissmann, B., "The Transglycosylative Action of Testicular Hyaluronidase" J Biol Chem 216(2):783-794 (Oct. 1, 1955).

Wurth and Adler, Declaration of Dr. Wurth and Dr. Adler (European Patent No. EP 2 459 167 B1 (Adler et al., filed: Jul. 28, 2010, granted: May 15, 2013)),:1-7 (Jan. 7, 2019).

(56) References Cited

OTHER PUBLICATIONS

Wurth et al., "Quality by design approaches to formulation robustness-an antibody case study" Journal of pharmaceutical sciences 105(5):1667-1675 (May 2016).

Wurth, Resume Dr. Christine Wurth:1-3 (Jan. 7, 2019).

Wynne, C. et al., "Comparison of Subcutaneous and Intravenous Administration of Trastuzumab: A Phase I/Ib Trial in Healthy Male Volunteers and Patients with HER2-Positive Breast Cancer" J Clin Pharmacol 53(2):192-201 (Jan. 24, 2013).

Xu, F. et al., "Antibody-Induced Growth Inhibition is Mediated Through Immunochemically and Functionally Distinct Epitopes on the Extracellular Domain of the c-erbB-2 (HER-2/neu) Gene Product p185" Int J Cancer 53(3):401-408 (Feb. 1, 1993).

Yocum et al., "Clinical trial of recombinant human PH20 hyaluronidase's effect on subcutaneous absorption and pharmacokinetics of a large protein molecule therapeutic" (Proceedings of the 34th Annual Meeting and Exposition of the Controlled Release Society held Jul. 7-11, 2007, Long Beach, California),:1-2 ( 2007).

Yocum, Richard, "Clinical Trial of Recombinant Human PH20 Hyaluronidase's Effect on Subcutaneous Absorption and Pharmacokinetics of a Large Protein Molecule Therapeutic" (Published as an Abstract, Table of Contents vol. 1 of 3, Jul. 7-11) 34th Annual Meeting and Exposition of the Controlled Release Society 2007, Long Beach, California, USA, pp. 1-6 (2007).

\* cited by examiner

SUBCUTANEOUS ANTI-HER2 ANTIBODY FORMULATIONS AND USES THEREOF

RELATED APPLICATIONS

This application is a divisional of U.S. patent application Ser. No. 18/635,280, filed Apr. 15, 2024, which is a continuation of U.S. patent application Ser. No. 18/459,857, filed Sep. 1, 2023, abandoned, which is a continuation of U.S. patent application Ser. No. 17/443,780, filed Jul. 27, 2021, abandoned, which is a continuation of U.S. patent application Ser. No. 15/949,616, filed Apr. 10, 2018, abandoned, which is a continuation of U.S. patent application Ser. No. 15/053,217, filed Feb. 25, 2016, now U.S. Pat. No. 9,968,676, issued May 15, 2018, which is a continuation of U.S. patent application Ser. No. 13/833,316, filed Mar. 15, 2013, abandoned, which is a continuation of U.S. patent application Ser. No. 12/804,703, filed Jul. 27, 2010, now U.S. Pat. No. 9,345,661, issued May 24, 2016, which claims benefit of priority to European Patent Application No. 09167025.7, filed Jul. 31, 2009, each of which is incorporated herein by reference in its entirety.

BACKGROUND OF THE INVENTION

The present invention relates to highly concentrated, stable pharmaceutical formulations of a pharmaceutically active anti-HER2 antibody or a mixture of such antibody molecules for subcutaneous injection. Such formulations comprise, in addition to the high amounts of anti-HER2 antibody or mixture thereof, a buffering agent, a stabilizer or a mixture of two ore more stabilizing agents, a nonionic surfactant and an effective amount of at least one hyaluronidase enzyme. The invention also relates to a process for the preparation of the said formulation and to the uses of such formulation.

The pharmaceutical use of antibodies has increased over the past years. In many instances such antibodies are injected via the intravenous (IV) route. Unfortunately the amount of antibody that can be injected via the intravenous route is limited by the physico-chemical properties of the antibody, in particularly by its solubility and stability in a suitable liquid formulation and by the volume of the infusion fluid. Alternative administration pathways are subcutaneous or intramuscular injection. These injection pathways require high protein concentration in the final solution to be injected [Shire, S. J., Shahrokh, Z. et al., "Challenges in the development of high protein concentration formulations", J. Pharm. Sci. 2004; 93(6): 1390-1402; Roskos, L. K., Davis C. G. et al., "The clinical pharmacology of therapeutic antibodies", Drug Development Research 2004; 61(3): 108-120]. In order to increase the volume, and thereby the therapeutic dose, which can be safely and comfortably administered subcutaneously it has been proposed to use glycosaminoglycanase enzyme(s) in order to increase the interstitial space into which the antibody formulation can be injected [WO2006/091871].

Examples of stable formulations of pharmaceutically active antibodies for therapeutic use currently on the market are as follows: HERCEPTIN™ (Trastuzumab) is a monoclonal antibody directed against the HER2 receptor (anti HER2 antibody) which is currently marketed in Europe in form of a 150 mg lyophilized powder (containing the antibody, α,α-trehalose dihydrate, L-histidine and L-histidine hydrochloride and polysorbate 20) which is reconstituted for infusions with water for injection to yield an injection dose of approximately 21 mg/ml. In the USA and many other countries a multiple dosage vial containing 440 mg Trastuzumab is marketed.

AVASTIN™ (Bevacizumab) is a monoclonal antibody directed against the vascular endothelial growth factor (VEGF) which is currently marketed in Europe as a liquid formulation in two types of vials: a) 100 mg Bevacizumab in 4 ml and b) 400 mg Bevacizumab in 16 ml, respectively, providing a final concentration of 25 mg/ml in water for injection containing the following excipients: trehalose dihydrate, sodium phosphate and polysorbate 20.

While the above antibody formulations have been found suitable for intravenous administration there is a desire to provide highly concentrated, stable pharmaceutical formulations of therapeutically active antibodies for subcutaneous injection. The advantage of subcutaneous injections is that it allows the medical practitioner to perform it in a rather short intervention with the patient. Moreover the patient can be trained to perform the subcutaneous injection by himself Such self-administration is particularly useful during maintenance dosing because no hospital care is needed (reduced medical resource utilization). Usually injections via the subcutaneous route are limited to approximately 2 ml. For patients requiring multiple doses, several unit dose formulations can be injected at multiple sites of the body surface.

The following two antibody products for subcutaneous administration are already on the market.

HUMIRA™ (Adalimumab) is a monoclonal antibody directed against tumor necrosis factor alpha (TNF alpha) which is currently marketed in Europe in form of a 40 mg dose in 0.8 ml injection volume for subcutaneous application (concentration: 50 mg antibody/ml injection volume).

XOLAIR™ (Omalizumab) a monoclonal antibody directed against immunoglobulin E (anti IgE antibody) which is currently marketed in form of a 150 mg lyophilized powder (containing the antibody, sucrose, histidine and histidine hydrochloride monohydrate and polysorbate 20) which is be reconstituted with water for subcutaneous injection to yield a 125 mg/ml injection dose.

No highly concentrated, stable pharmaceutical anti-HER2 antibody formulation suitable for subcutaneous administration is currently available on the market. There is therefore a desire to provide such highly concentrated, stable pharmaceutical formulations of therapeutically active antibodies for subcutaneous injection.

The injection of parenteral drugs into the hypodermis is generally limited to volumes of less than 2 ml due to the viscoelastic resistance to hydraulic conductance in the subcutaneous (SC) tissue, due to the generated backpressure upon injection [Aukland K. and Reed R., "Interstitial-Lymphatic Mechanisms in the control of Extracellular Fluid Volume", Physiology Reviews", 1993; 73:1-78], as well as due to the perceptions of pain.

The preparation of high concentration protein formulations is rather challenging and there is a need to adapt each formulation to the particular proteins used because each protein has a different aggregation behavior. Aggregates are suspected to cause immunogenicity of therapeutic proteins in at least some of the cases. Immunogenic reaction against protein or antibody aggregates may lead to neutralizing antibodies which may render the therapeutic protein or antibody ineffective. It appears that the immunogenicity of protein aggregates is most problematic in connection with subcutaneous injections, whereby repeated administration increases the risk of an immune response.

While antibodies have a very similar overall structure, such antibodies differ in the amino acid composition (in particular in the CDR regions responsible for the binding to the antigen) and the glycosylation pattern. Moreover there may additionally be post-translational modifications such as charge and glycosylation variants. In the particular case of anti-HER2 antibodies such post-translational modifications have been described e.g. for the humanized monoclonal antibody humMAb4D5-8 (=Trastuzumab). Particular purification methods for the removal of e.g. acidic variants have been developed and compositions comprising a reduced amount of acidic variants (predominantly deamidated variants wherein one or more asparagine residue(s) of the original polypeptide have been converted to aspartate, i.e. the neutral amide side chain has been converted to a residue with an overall acidic character) have first been provided by Basey, C. D and Blank, G. S. in WO99/57134.

Stable lyophilized antibody formulations comprising a lyoprotectant, a buffer and a surfactant have been described by Andya et al. (WO 97/04801 and U.S. Pat. Nos. 6,267,958, 6,685,940, 6,821,151 and 7,060,268).

WO 2006/044908 provides antibody formulations, including monoclonal antibodies formulated in histidine-acetate buffer, pH 5.5 to 6.5, preferably 5.8 to 6.2.

The problem to be solved by the present invention is therefore to provide novel highly concentrated, stable pharmaceutical formulations of a pharmaceutically active anti-HER2 antibody or a mixture of anti-HER2 antibody molecules for subcutaneous injection. Such formulations comprise, in addition to the high amounts of anti-HER2 antibody or anti-HER2 antibody mixture, a buffering agent, a stabilizer or a mixture of two or more stabilizers, a nonionic surfactant and an effective amount of at least one hyaluronidase enzyme. The preparation of highly-concentrated antibody formulations is challenging because of a potential increase in viscosity at higher protein concentration and a potential increase in protein aggregation, a phenomenon that is per se concentration-dependent. High viscosities negatively impact the process ability (e.g. pumping and filtration steps) of the antibody formulations and the administration (e.g. the syringe ability). By the addition of excipients high viscosities could be decreased in some cases. Control and analysis of protein aggregation is an increasing challenge. Aggregation is potentially encountered during various steps of the manufacturing process, which include fermentation, purification, formulation and during storage. Different factors, such as temperature, protein concentration, agitation stress, freezing and thawing, solvent and surfactant effects, and chemical modifications, might influence the aggregation behavior of a therapeutic protein. During development of a highly concentrated antibody formulation the aggregation tendency of the protein has to be monitored and controlled by the addition of 5 various excipients and surfactants [Kiese S. et al., J. Pharm. Sci., 2008; 97(10); 4347-4366]. The challenge to prepare suitable highly concentrated, stable pharmaceutical formulation of the pharmaceutically active anti-HER2 antibody in accordance with the present invention is increased by the fact that two different proteins have to be formulated in one liquid formulation in such a way that the formulation remains stable over several weeks and the pharmaceutically active ingredients remain active during proper storage.

SUMMARY OF THE INVENTION

In a first aspect the present invention provides highly concentrated, stable pharmaceutical formulations of a pharmaceutically active anti-HER2 antibody or a mixture of such antibody molecules for subcutaneous injection, which are ready for use.

More particularly the highly concentrated, stable pharmaceutical formulation of a pharmaceutically active anti-HER2 antibody formulation of the present invention comprises:
  about 50 to 350 mg/ml anti-HER2 antibody;
  about 1 to 100 mM of a buffering agent providing a pH of 5.5±2.0;
  about 1 to 500 mM of a stabilizer or a mixture of two or more stabilizers, whereby optionally methionine is present as a secondary stabilizer e.g. in a concentration of 5 to 25 mM;
  0.01 to 0.1% of a nonionic surfactant; and
  an effective amount of at least one hyaluronidase enzyme.

In a further aspect the present invention provides for use of a formulation for the preparation of a medicament useful for treating a disease or disorder amenable to treatment with an anti-HER2 antibody such as e.g. cancer or a non-malignant disease in a subject comprising administering the formulation described herein to a subject in an amount effective to treat the said disease or disorder. The anti-HER2 antibody can be co-administered concomitantly or sequentially with a chemotherapeutic agent.

In another aspect the present invention there are provided methods of treating a disease or disorder which is amenable to treatment with an anti-HER2 antibody (e.g. cancer or a non-malignant disease) in a subject comprising administering the formulation described herein to a subject in an amount effective to treat the said disease or disorder. The cancer or a non-malignant disease will generally involve HER2-expressing cells, such that the HER2 antibody in the therapeutic pharmaceutical SC formulation in accordance with the present invention is able to bind to the affected cells.

The present invention also provides pharmaceutical compositions consisting of a highly concentrated, stable pharmaceutical formulation of a pharmaceutically active anti-HER2 antibody or a mixture of such antibody and a suitable amount of at least one hyaluronidase enzyme in the form of a kit comprising both injection components and suitable instructions for their subcutaneous administration.

A further aspect of the present invention relates to injection devices comprising a highly concentrated, stable pharmaceutical formulation in accordance with the present invention. Such formulation may consist of a pharmaceutically active anti-HER2 antibody or a mixture of such antibody molecules and suitable excipients as outlined below and may additionally comprise a soluble hyaluronidase glycoprotein either as a combined formulation or as a separate formulation for co-administration.

DETAILED DESCRIPTION OF THE INVENTION

Figure 1:
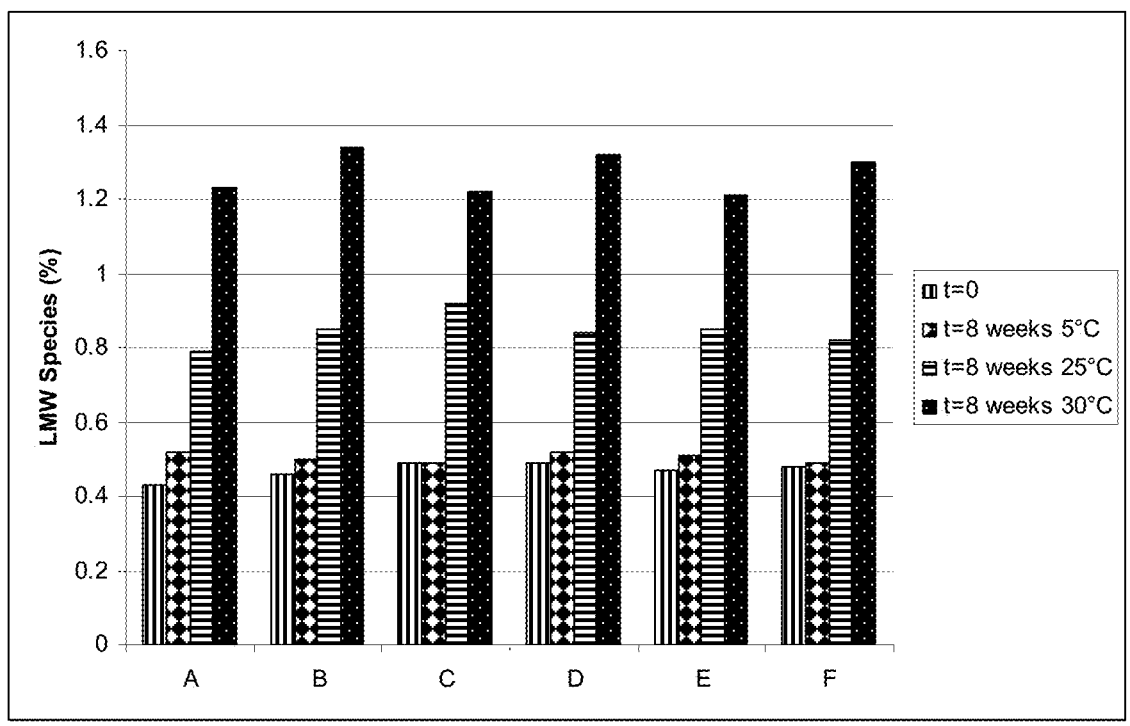
FIG. 1 shows stability of the formulations A to F (see Table 1 below) after 8 weeks with respect to Low Molecular Weight (LMW) Species detected by Size Exclusion-HPLC. As shown in this figure the PS20 formulations A, C and E showed a slightly better stability than the PS80 formulations B, D and F upon storage at 30° C.

The highly concentrated, stable pharmaceutical formulation of a pharmaceutically active anti-HER2 antibody formulation of the present invention may be provided in liquid form or may be provided in lyophilized form. In accordance with the teachings in WO 97/04801 the antibody concentration in the reconstituted formulation can be increased by reconstitution of a lyophilized formulation to provide a protein concentration in the reconstituted formulation which is about 2-40 times greater than the protein concentration in the mixture before the lyophilization step.

The anti-HER2 antibody concentration is 100 to 150 mg/ml, e.g. 120±18 mg/ml, about 110 mg/ml, about 120 mg/ml or about 130 mg/ml.

The concentration of the buffering agent providing a pH of 5.5±2.0 is 1 to 50 mM, e.g. 10 to 30 mM or about 20 mM. Various buffering agents are known to the person skilled in the art as outlined further below. The buffering agent can be a histidine buffer, e.g. L-histidine/HCl. In a particular embodiment the pH of the L-histidine/HCl buffer is about 5.5 or about 6.0.

The stabilizer (used synonymously with the term "stabilizing agent" in the present patent description) is e.g. a carbohydrate or saccharide or a sugar admitted by the authorities as a suitable additive or excipient in pharmaceutical formulations, e.g. α,α-trehalose dihydrate or sucrose. The concentration of the stabilizer is 15 to 250 mM, or 150 to 250 mM, or about 210 mM. The formulation may contain a secondary stabilizer, whereby this secondary stabilizer can be methionine, e.g in a concentration of 5 to 25 mM or in a concentration of 5 to 15 mM (e.g. methionine in a concentration of about 5 mM, about 10 mM or about 15 mM).

Suitable examples of pharmaceutically acceptable surfactants include polyoxyethylensorbitan fatty acid esters (Tween), polyethylene-polypropylene glycols, polyoxyethylene-stearates, polyoxyethylene alkyl ethers, e.g. polyoxyethylene monolauryl ether, alkylphenylpolyoxyethylene ethers (Triton-X), polyoxyethylene-polyoxypropylene copolymer (Poloxamer, Pluronic), and sodium dodecyl sulphate (SDS). Most suitable polyoxyethylenesorbitan-fatty acid esters are polysorbate 20, (sold under the trademark Tween 20™) and polysorbate 80 (sold under the trademark Tween 80™). Most suitable polyethylene-polypropylene copolymers are those sold under the names Pluronic® F68 or Poloxamer 188™. Most suitable polyoxyethylene alkyl ethers are those sold under the trademark Brij™. Most suitable alkylphenolpolyoxyethylene ethers are sold under the trade name Triton-X. The nonionic surfactant can be a polysorbate, e.g. selected from the group of polysorbate 20, polysorbate 80 and polyethylene-polypropylene copolymer. The concentration of the nonionic surfactant is 0.01 to 0.1% (w/v), or 0.01 to 0.08% (w/v), or 0.025 to 0.075% (w/v), or more particularly about 0.02, 0.04 or 0.06% (w/v).

The concentration of the hyaluronidase enzyme depends on the actual hyaluronidase enzyme used in the preparation of the formulation in accordance with the invention. An effective amount of the hyaluronidase enzyme can easily be determined by the person skilled in the art based on the disclosure further below. It should be provided in sufficient amount so that an increase in the dispersion and absorption of the co-administered anti-HER2 antibody is possible. The minimal amount of the hyaluronidase enzyme is >150 U/ml. More particularly the effective amount of the hyaluronidase enzyme is about 1,000 to 16,000 U/ml, whereby the said amount corresponds to about 0.01 mg to 0.16 mg protein based on an assumed specific activity of 100,000 U/mg. Alternatively the concentration of the hyaluronidase enzyme is about 1,500 to 12,000 U/ml, or more particularly about 2,000 U/ml or about 12,000 U/ml. The amounts specified hereinbefore correspond to the amount of hyaluronidase enzyme initially added to the formulation. As evidenced in the example formulations the hyaluronidase enzyme concentrations measured in the final formulation may vary within a certain range. Thus, e.g. the actually measured hyaluronidase enzyme (HE) concentration measured just after adding 12,000 U/ml of enzyme showed variations between 12355 U/ml to 15178 U/ml (see Table 1 Formulations A to F and Table 3 Formulation H). The hyaluronidase enzyme is present either as a combined final formulation or for use for co-administration, e.g. as a co-formulation as further outlined below. The important issue for the formulation in accordance with the present invention is that at the time it is ready for use and/or is injected it has the composition as set out in the appended claims. The ratio (w/w) of the hyaluronidase enzyme to the anti-HER2 antibody is in the range of 1:1,00 to 1:8,000, or in the range of 1:4,000 to 1:5,000 or about 1:6,000.

The hyaluronidase enzyme may be derived from animals, human samples or manufactured based on the recombinant DNA technology as described further below.

In some embodiments the highly concentrated, stable pharmaceutical anti-HER2 antibody formulations in accordance with the present invention have one of the following compositions:

a) 100 to 150 mg/ml anti-HER2 antibody, e.g. selected from the group of Trastuzumab, Pertuzumab and T-DM1; 1 to 50 mM of a histidine buffer, e.g. L-histidine/HCl at a pH of about 5.5; 15 to 250 mM of a stabilizer which is e.g. α,α-trehalose dihydrate, and optionally methionine as a second stabilizer at a concentration of 5 to 25 mM; about 0.01 to 0.08% of a nonionic surfactant; and >150 to 16,000 U/ml, more particularly 1,000 to 16,000 U/ml of a hyaluronidase enzyme such as e.g. rHuPH20, e.g. at a concentration of about 2,000 U/ml or about 12,000 U/ml.

b) 120±18 mg/ml anti-HER2 antibody, e.g. selected from the group of Trastuzumab, Pertuzumab and T-DM1; 10 to 30 mM, or about 20 mM of a histidine buffer such as e.g. L-histidine/HCl at a pH of about 5.5; 150 to 250 mM or about 210 mM of a stabilizer, which is e.g. α,α-trehalose dihydrate, and optionally methionine as a second stabilizer at a concentration of 5 to 25 mM, or 5 to 15 mM, or about 10 mM; about 0.01 to 0.08% of a nonionic surfactant; and 1,000 to 16,000 U/ml, or 1,500 to 12,000 U/ml, about 2,000 U/ml or about 12,000 U/ml of a hyaluronidase enzyme such as e.g. rHuPH20.

c) About 120 mg/ml anti-HER2 antibody, e.g. selected from the group of Trastuzumab, Pertuzumab and T-DM1; 10 to 30 mM, or about 20 mM of a histidine buffer, such as e.g. L-histidine/HCl at a pH of about 5.5; 150 to 250 mM, e.g. about 210 mM of a stabilizer, which is e.g. α,α-trehalose dihydrate, and optionally methionine as a second stabilizer at a concentration of 5 to 25 mM, or 5 to 15 mM, or about 10 mM; about 0.01 to 0.08% of a nonionic surfactant; and 1,000 to 16,000 U/ml, or 1,500 to 12,000 U/ml, or more particularly about 2,000 U/ml or about 12,000 U/ml of a hyaluronidase enzyme such as e.g. rHuPH20.

d) About 120 mg/ml anti-HER2 antibody, e.g. selected from the group of Trastuzumab, Pertuzumab and T-DM1; about 20 mM of a histidine buffer such as e.g. L-histidine/HCl at a pH of about 5.5; about 210 mM α,α-trehalose dihydrate, and optionally about 10 mM methionine as a second stabilizer; 0.04 or 0.06% of polysorbate 20; and about 12,000 U/ml of a hyaluronidase enzyme such as rHuPH20; and particularly the Formulation A specified below.

e) About 120 mg/ml anti-HER2 antibody, e.g. selected from the group of Trastuzumab, Pertuzumab and T-DM1; about 20 mM of a histidine buffer such as e.g. L-histidine/HCl at a pH of about 5.5; about 210 mM α,α-trehalose dihydrate, and optionally 10 mM methionine as a second stabilizer; 0.04 or 0.06% of polysorbate 20; and about 2,000 U/ml of a hyaluronidase enzyme such as rHuPH20; and particularly the Formulation X specified below.

f) A lyophilized formulation comprising 120 mg/ml anti-HER2 antibody, e.g. selected from the group of Trastuzumab, Pertuzumab and T-DM1; 20 mM of a histidine buffer such as e.g. L-histidine/HCl at a pH of about 5.5; 210 mM of α,α-trehalose dihydrate and optionally 10 mM methionine as a second stabilizer; about 0.04 to 0.06% of a nonionic surfactant; and particularly Formulation Y specified below. These formulations can be reconstituted with 1,000 to 16,000 U/ml, or 1,500 to 12,000 U/ml, or more particularly about 2,000 U/ml or about 12,000 U/ml of a hyaluronidase enzyme such as e.g. rHuPH20.

In another embodiment the highly concentrated, stable pharmaceutical anti-HER2 antibody formulations in accordance with the present invention have one of the compositions specified in Table 1, 3 and 4, whereby the formulations C, D, E and F are less preferred because of less desired properties as outlined in the Examples and in Table 1.

It has been proposed to facilitate the subcutaneous injection of therapeutic proteins and antibodies by using small amounts of soluble hyaluronidase glycoproteins (sHASEGPs); see WO2006/091871. It has been shown that the addition of such soluble hyaluronidase glycoproteins (either as a combined formulation or by co-administration) facilitates the administration of therapeutic drug into the hypodermis. By rapidly depolymerizing hyaluronan HA in the extracellular space sHASEGP reduces the viscosity of the interstitium, thereby increasing hydraulic conductance and allowing for larger volumes to be administered safely and comfortably into the subcutaneous tissue. The increased hydraulic conductance induced by sHASEGP through reduced interstitial viscosity allows for greater dispersion, potentially increasing the systemic bioavailability of SC administered therapeutic drug.

The highly concentrated, stable pharmaceutical formulations of the present invention comprising a soluble hyaluronidase glycoprotein are therefore particularly suited for subcutaneous injection. It is clearly understood by the person skilled in the art that such a formulation comprising an anti-HER2 antibody and a soluble hyaluronidase glycoprotein can be provided for administration in form of one single combined formulation or alternatively in form of two separate formulations which can be mixed just prior to the subcutaneous injection. Alternatively the anti-HER2 antibody and the soluble hyaluronidase glycoprotein can be administered as separate injections at different sites of the body, preferably at sites which are immediately adjacent to each other. It is also possible to inject the therapeutic agents present in the formulation in accordance with the present invention as consecutive injections, e.g. first the soluble hyaluronidase glycoprotein followed by the injection of the anti-HER2 antibody formulation. These injections can also be performed in the reversed order, viz. by first injecting the anti-HER2 antibody formulation followed by injecting the soluble hyaluronidase glycoprotein. In case the anti-HER2 antibody and the soluble hyaluronidase glycoprotein are administered as separate injections, one or both of the proteins have to be provided with the buffering agent, the stabilizer(s) and the nonionic surfactant in the concentrations as specified in the appended claims but excluding the hyaluronidase enzyme. The hyaluronidase enzyme can then be provided e.g. in a L-histidine/HCl buffer at pH of about 6.5, 100 to 150 mM NaCl and 0.01 to 0.1% (w/v) polysorbate 20 or polysorbate 80. In particular the hyaluronidase enzyme is provided in 20 mM L-histidine/HCl buffer at pH 6.5, 130 mM NaCl, 0.05% (w/v) polysorbate 80 as specifically exemplified in Formulation G of Table 1 below.

As noted above the soluble hyaluronidase glycoprotein may be considered to be a further excipient in the anti-HER2 formulation. The soluble hyaluronidase glycoprotein may be added to the anti-HER2 formulation at the time of manufacturing the anti-HER2 formulation or may be added shortly before the injection. Alternatively the soluble hyaluronidase glycoprotein may be provided as a separate injection. In the latter case the soluble hyaluronidase glycoprotein may be provided in a separate vial either in lyophilized form which must be reconstituted with suitable diluents before the subcutaneous injection takes place, or may be provided as a liquid formulation by the manufacturer. The anti-HER2 formulation and the soluble hyaluronidase glycoprotein may be procured as separate entities or may also be provided as kits comprising both injection components and suitable instructions for their subcutaneous administration. Suitable instructions for the reconstitution and/or administration of one or both of the formulations may also be provided.

A variety of anti-HER2 antibodies are known in the prior art. Such antibodies are preferably monoclonal antibodies. They may either be so-called chimaeric antibodies, humanized antibodies or fully human antibodies. They may either be full length anti-HER2 antibodies; anti-HER2 antibody fragments having the same biological activity; including amino acid sequence variants and/or glycosylation variants of such antibodies or antibody fragments. Examples of humanized anti-HER2 antibodies are known under the INN names Trastuzumab and Pertuzumab. Another suitable anti-HER2 antibody is T-DM1, which is an antibody-toxin conjugate consisting of huMAb4D5-8 (HERCEPTIN™) and a maytansinoide (viz. DM1=$N^{2'}$-deacetyl-$N^{2'}$-(3-mercapto-1-oxopropyl)-maytansine; a highly potent antimicrotubule agent) which conjugate (with a MCC linker) is currently under development for metastatic breast cancer. Other HER2 antibodies with various properties have been described in Tagliabue et al., Int. J. Cancer, 47:933-937 (1991); McKenzie et al., Oncogene, 4:543-548 (1989); Cancer Res., 51:5361-5369 (1991); Bacus et al., Molecular Carcinogenesis, 3:350-362 (1990); Stancovski et al., PNAS (USA), 88:8691-8695 (1991); Bacus et al., Cancer Research, 52:2580-2589 (1992); Xu et al., Int. J. Cancer, 53:401-408 (1993); WO94/00136; Kasprzyk et al., Cancer Research, 52:2771-2776 (1992); Hancock et al., Cancer Res., 51:4575-

4580 (1991); Shawver et al., Cancer Res., 54:1367-1373 (1994); Arteaga et al., Cancer Res., 54:3758-3765 (1994); Harwerth et al., J. Biol. Chem., 267:15160-15167 (1992); U.S. Pat. No. 5,783,186; and Klapper et al., Oncogene, 14:2099-2109 (1997). The most successful therapeutic anti-HER2 antibody is Trastuzumab sold by Genentech Inc. and F. Hoffmann-La Roche Ltd under the trade name HERCEPTIN™. Further details on the HER2 antigen and antibodies directed thereto are described in many patent and non-patent publications (for a suitable overview see U.S. Pat. No. 5,821,337 and WO 2006/044908).

The anti-HER2 antibody is e.g. selected from the group of Trastuzumab, Pertuzumab and T-DM1 and may also consist of a mixture of anti-HER2 antibodies such as e.g. Trastuzumab and Pertuzumab or T-DM1 and Pertuzumab. It has been found that the combination of Pertuzumab and Trastuzumab is active and well tolerated in patients with metastatic HER2-positive breast cancer who had experienced progression during prior trastuzumab therapy [se e.g. Baselga, J. et al., Journal of Clin. Oncol. Vol 28 (7) 2010: pp. 1138-1144]. The formulation in accordance with the present invention is exemplified herein with the anti-HER2 antibody Trastuzumab. The terms "Trastuzumab", "Pertuzumab" and "T-DM1" encompass all corresponding anti-HER2 antibodies that full-fill the requirements necessary for obtaining a marketing authorization as an identical or biosimilar product in a country or territory selected from the group of countries consisting of the USA, Europe and Japan. Trastuzumab has the CDR regions defined in EP-B-590058. Pertuzumab has the CDR regions defined in WO 01/00245. The activity of Trastuzumab in the BT-474 antiproliferation assay [Nahta, R. et al., "The HER-2-targeting antibodies Trastuzumab and Pertuzumab synergistically inhibit the survival of breast cancer cells", Cancer Res. 2004; 64:2343.2346] has been found to be between $0.7-1.3 \times 10^4$ U/mg. T-DM1 is described in WO 2005/117986.

HERCEPTIN™ (Trastuzumab) has been approved in the EU for the treatment of patients with metastatic breast cancer (MBC) who have tumors that overexpress HER2 as follows:
  As monotherapy for the treatment of patients who have received at least two chemotherapy regimens for their metastatic disease. Prior chemotherapy must have included at least an anthracycline and a taxane unless patients are unsuitable for these treatments. Hormone receptor-positive patients must also have failed hormonal therapy, unless patients are unsuitable for these treatments.
  In combination with paclitaxel for the treatment of those patients who have not received chemotherapy for their metastatic disease and for whom an anthracycline is not suitable.
  In combination with docetaxel for the treatment of those patients who have not received chemotherapy for their metastatic disease.
  In combination with an aromatase inhibitor for the treatment of postmenopausal patients with hormone receptor-positive MBC not previously treated with Trastuzumab.

Trastuzumab has also been approved in the EU for the treatment of patients with MBC who have tumors that overexpress HER2 for the treatment of patients with HER2-positive early-stage breast cancer (EBC) following surgery, chemotherapy (neoadjuvant or adjuvant) and radiotherapy (if applicable).

Moreover Trastuzumab is currently being developed for the treatment of gastric cancer.

Two dosing regimens are currently approved for Trastuzumab (Table 1); once weekly (q1w) and every 3 weeks (q3w) for both metastatic breast cancer (MBC) and early breast cancer (EBC). In the q1w dosing regime the loading dose is 4 mg/kg followed by subsequent dose at 2 mg/kg. In the q3w dosing regime the loading dose is 8 mg/kg followed by subsequent dose at 6 mg/kg.

As noted above HERCEPTIN™ (Trastuzumab) for intravenous administration is currently sold in lyophilized form in vials. In the formulation sold in Europe each vial contains the dry residue obtained after lyophilization of a filling volume of 6.25 ml of a sterile aqueous solution containing the following components: 150 mg Trastuzumab (effective 156.3 mg to ensure that the nominal quantity of 150 mg can be withdrawn from the final product after reconstitution), 3.50 mg L-histidine hydrochloride, 2.25 mg L-histidine, 141.9 mg α,α-trehalose dihydrate, 0.63 mg Polysorbate 20. The dissolved lyophilisate contains about 24 mg/ml Trastuzumab, 5 mM L-histidine/HCl pH 6.0, 60 mM α,α-trehalose dihydrate, 0.01% polysorbate 20. The solution is then added to the infusion solution and then the infusion is administered to the patient over 90 minutes (subsequent infusions can be given over 30 minutes in MBC, if well tolerated).

A number of a soluble hyaluronidase glycoprotein are known in the prior art. In order to further define the function, the mechanism of action and the properties of such soluble hyaluronidase glycoproteins the following background information is provided.

The SC (hypodermal) interstitial matrix is comprised of a network of fibrous proteins embedded within a viscoelastic gel of glycosaminoglycans. Hyaluronan (HA), a non-sulfated repeating linear disaccharide, is the prominent glycosaminoglycan of the SC tissue. HA is secreted into the interstitium by fibroblasts as a high molecular weight, megadalton viscous polymer that is subsequently degraded locally, in the lymph, and in the liver, through the action of lysosomal hyaluronidases and exoglycosidases. Approximately 50% of the hyaluronan in the body is produced by the SC tissue, where it is found at approximately 0.8 mg/gm wet weight tissue [Aukland K. and Reed R., supra]. It is estimated that the average 70 kg adult contains 15 grams of HA, of which 30 percent is turned over (synthesized and degraded) daily [Laurent L. B., et al., "Catabolism of hyaluronan in rabbit skin takes place locally, in lymph nodes and liver", Exp. Physiol. 1991; 76: 695-703]. As a major constituent of the gel-like component of the hypodermal matrix, HA contributes significantly to its viscosity.

Glycosaminoglycans (GAGs) are complex linear polysaccharides of the extracellular matrix (ECM). GAGs are characterized by repeating disaccharide structures of an N-substituted hexosamine and an uronic acid (in the case of hyaluronan (HA), chondroitin sulfate (CS), chondroitin (C), dermatan sulfate (DS), heparan sulfate (HS), and heparin (H)), or a galactose (in the case of keratan sulfate (KS)). Except for HA, all exist covalently bound to core proteins. The GAGs with their core proteins are structurally referred to as proteoglycans (PGs).

Hyaluronan (HA) is found in mammals predominantly in connective tissues, skin, cartilage, and in synovial fluid. Hyaluronan is also the main constituent of the vitreous of the eye. In connective tissue, the water of hydration associated with hyaluronan creates hydrated matrices between tissues. Hyaluronan plays a key role in biological phenomena associated with cell motility including rapid development, regeneration, repair, embryogenesis, embryological development, wound healing, angiogenesis, and tumorigenesis (Toole, Cell Biol. Extracell. Matrix, Hay (ed), Plenum Press, New York, 1991; pp. 1384-1386; Bertrand et al., Int. J. Cancer 1992; 52:1-6; Knudson et al., FASEB J. 1993; 7:1233-1241]. In addition, hyaluronan levels correlate with tumor aggressiveness [Ozello et al., Cancer Res. 1960; 20:600-604; Takeuchi et al., Cancer Res. 1976; 36:2133-2139; Kimata et al., Cancer Res. 1983; 43:1347-1354].

HA is found in the extracellular matrix of many cells, especially in soft connective tissues. HA has been assigned various physiological functions, such as in water and plasma protein homeostasis [Laurent T. C. et al., FASEB J., 1992; 6: 2397-2404]. HA production increases in proliferating cells and may play a role in mitosis. It has also been implicated in locomotion and cell migration. HA seems to play important roles in cell regulation, development, and differentiation [Laurent et al., supra].

HA has widely been used in clinical medicine. Its tissue protective and rheological properties have proved useful in ophthalmic surgery (e.g. to protect the corneal endothelium during cataract surgery). Serum HA is diagnostic of liver disease and various inflammatory conditions, such as rheumatoid arthritis. Interstitial edema caused by accumulation of HA may cause dysfunction in various organs [Laurent et al., supra].

Hyaluronan protein interactions also are involved in the structure of the extracellular matrix or "ground substance".

Hyaluronidases are a group of generally neutral- or acid-active enzymes found throughout the animal kingdom. Hyaluronidases vary with respect to substrate specificity, and mechanism of action (WO 2004/078140). There are three general classes of hyaluronidases:
1. Mammalian-type hyaluronidases, (EC 3.2.1.35) which are endo-beta-N-acetylhexosaminidases with tetrasaccharides and hexasaccharides as the major end products. They have both hydrolytic and transglycosidase activities, and can degrade hyaluronan and chondroitin sulfates (CS), generally C4-S and C6-S.
2. Bacterial hyaluronidases (EC 4.2.99.1) degrade hyaluronan and, and to various extents, CS and DS. They are endo-beta-N-acetylhexosaminidases that operate by a beta elimination reaction that yields primarily disaccharide end products.
3. Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Mammalian hyaluronidases can be further divided into two groups: neutral-active and acid-active enzymes. There are six hyaluronidase-like genes in the human genome, HYAL1, HYAL2, HYAL3, HYAL4, HYALP1 and PH20/SPAM1. HYALP1 is a pseudogene, and HYAL3 has not been shown to possess enzyme activity toward any known substrates. HYAL4 is a chondroitinase and exhibits little activity towards hyaluronan. HYAL1 is the prototypical acid-active enzyme and PH20 is the prototypical neutral-active enzyme. Acid-active hyaluronidases, such as HYAL1 and HYAL2 generally lack catalytic activity at neutral pH (i.e. pH 7). For example, HYAL1 has little catalytic activity in vitro over pH 4.5 [Frost I. G. and Stern, R., "A microtiter-based assay for hyaluronidase activity not requiring specialized reagents", Anal. Biochemistry, 1997; 251:263-269]. HYAL2 is an acid-active enzyme with a very low specific activity in vitro.

The hyaluronidase-like enzymes can also be characterized by those which are generally locked to the plasma membrane via a glycosylphosphatidyl inositol anchor such as human HYAL2 and human PH20 [Danilkovitch-Miagkova et al., Proc. Natl. Acad. Sci. USA, 2003; 100(8):4580-4585; Phelps et al., Science 1988; 240(4860): 1780-1782], and those which are generally soluble such as human HYAL1 [Frost, I. G. et al., "Purification, cloning, and expression of human plasma hyaluronidase", Biochem. Biophys. Res. Commun. 1997; 236(1):10-15]. However, there are variations from species to species: bovine PH20 for example is very loosely attached to the plasma membrane and is not anchored via a phospholipase sensitive anchor [Lalancette et al., Biol. Reprod., 2001; 65(2):628-36]. This unique feature of bovine hyaluronidase has permitted the use of the soluble bovine testes hyaluronidase enzyme as an extract for clinical use (Wydase™, Hyalase™). Other PH20 species are lipid anchored enzymes that are generally not soluble without the use of detergents or lipases. For example, human PH20 is anchored to the plasma membrane via a GPI anchor. Attempts to make human PH20 DNA constructs that would not introduce a lipid anchor into the polypeptide resulted in either a catalytically inactive enzyme, or an insoluble enzyme [Arming et al., Eur. J. Biochem., 1997; 247(3):810-4]. Naturally occurring macaque sperm hyaluronidase is found in both a soluble and membrane bound form. While the 64 kDa membrane bound form possesses enzyme activity at pH 7.0, the 54 kDa form is only active at pH 4.0 [Cherr et al., Dev. Biol., 1996; 10; 175(1): 142-53]. Thus, soluble forms of PH20 are often lacking enzyme activity under neutral conditions.

As noted above and in accordance with the teachings in WO2006/091871 small amounts of soluble hyaluronidase glycoproteins (sHASEGPs) can be introduced into a formulation in order to facilitate the administration of therapeutic drug into the hypodermis. By rapidly depolymerizing HA in the extracellular space sHASEGP reduces the viscosity of the interstitium, thereby increasing hydraulic conductance and allowing for larger volumes to be administered safely and comfortably into the SC tissue. The increased hydraulic conductance induced by sHASEGP through reduced interstitial viscosity allows for greater dispersion, potentially increasing the systemic bioavailability of SC administered therapeutic drug.

When injected in the hypodermis, the depolymerization of HA by sHASEGP is localized to the injection site in the SC tissue. Experimental evidence shows that the sHASEGP is inactivated locally in the interstitial space with a half life of 13 to 20 minutes in mice, without detectable systemic absorption in blood following single intravenous dose in CD-1 mice. Within the vascular compartment sHASEGP demonstrates a half life of 2.3 and 5 minutes in mice and Cynomolgus monkeys, respectively, with doses up to 0.5 mg/kg. The rapid clearance of sHASEGP, combined with the continual synthesis of the HA substrate in the SC tissue, results in a transient and locally-active permeation enhancement for other co-injected molecules, the effects of which are fully reversible within 24 to 48 hours post administration [Bywaters G. L., et al., "Reconstitution of the dermal barrier to dye spread after Hyaluronidase injection", Br. Med. J., 1951; 2 (4741): 1178-1183].

In addition to its effects on local fluid dispersion, sHASEGP also acts as absorption enhancer. Macromolecules greater than 16 kilodaltons (kDa) are largely excluded from absorption through the capillaries via diffusion and are mostly absorbed via the draining lymph nodes. A subcutaneously administered macromolecule such as e.g. a therapeutic antibody (molecular weight approximately 150 kDa) must therefore traverse the interstitial matrix before reaching the draining lymphatics for subsequent absorption into the vascular compartment. By increasing local dispersion, sHASEGP increases the rate (Ka) of absorption of many macromolecules. This leads to increased peak blood levels ($C_{max}$) and potentially to increased bioavailability relative to SC administration in the absence of sHASEGP [Bookbinder L. H., et al., "A recombinant human enzyme for enhanced interstitial transport of therapeutics", J. Control. Release 2006; 114: 230-241].

Hyaluronidase products of animal origin have been used clinically for over 60 years, primarily to increase the dispersion and absorption of other co-administered drugs and for hypodermoclysis (SC injection/infusion of fluid in large volume) [Frost G. I., "Recombinant human hyaluronidase (rHuPH20): an enabling platform for subcutaneous drug and fluid administration", Expert Opinion on Drug Delivery, 2007; 4: 427-440]. The details on the mechanism of action of hyaluronidases have been described in detail in the following publications: Duran-Reynolds F., "A spreading factor in certain snake venoms and its relation to their mode of action", CR Soc Biol Paris, 1938; 69-81; Chain E., "A mucolytic enzyme in testes extracts", Nature 1939; 977-978; Weissmann B., "The transglycosylative action of testicular hyaluronidase", J. Biol. Chem., 1955; 216: 783-94; Tammi, R., Saamanen, A. M., Maibach, H. I., Tammi M., "Degradation of newly synthesized high molecular mass hyaluronan in the epidermal and dermal compartments of human skin in organ culture", J. Invest. Dermatol. 1991; 97:126-130; Laurent, U. B. G., Dahl, L. B., Reed, R. K., "Catabolism of hyaluronan in rabbit skin takes place locally, in lymph nodes and liver", Exp. Physiol. 1991; 76: 695-703; Laurent, T. C. and Fraser, J. R. E. "Degradation of Bioactive Substances: Physiology and Pathophysiology", Henriksen, J. H. (Ed) CRC Press, Boca Raton, FL; 1991. pp. 249-265; Harris, E. N., et al., "Endocytic function, glycosaminoglycan specificity, and antibody sensitivity of the recombinant human 190-kDa hyaluronan receptor for endocytosis (HARE)", J. Biol. Chem. 2004; 279:36201-36209; Frost, G. I., "Recombinant human hyaluronidase (rHuPH20): an enabling platform for subcutaneous drug and fluid administration", Expert Opinion on Drug Delivery, 2007; 4: 427-440. Hyaluronidase products approved in EU countries include Hylase® "Dessau" and Hyalase®. Hyaluronidase products of animal origin approved in the US include Vitrase™, Hydase™, and Amphadase™.

The safety and efficacy of hyaluronidase products have been widely established. The most significant safety risk identified is hypersensitivity and/or allergenicity, which is thought to be related to the lack of purity of the animal-derived preparations [Frost, G. I., "Recombinant human hyaluronidase (rHuPH20): an enabling platform for subcutaneous drug and fluid administration", Expert Opinion on Drug Delivery, 2007; 4: 427-440]. It should be noted that there are differences with respect to the approved dosages of animal-derived hyaluronidases between the UK, Germany and the US. In the UK, the usual dose as an adjuvant to subcutaneous or intramuscular injection is 1500 units, added directly to the injection. In the US, the usual dose used for this purpose is 150 units. In hypodermoclysis, hyaluronidase is used to aid the subcutaneous administration of relatively large volumes of fluids. In the UK, 1500 units of hyaluronidase are generally given with each 500 to 1000 ml of fluid for subcutaneous use. In the US, 150 units are considered adequate for each liter of hypodermoclysis solution. In Germany, 150 to 300 units are considered adequate for this purpose. In the UK, the diffusion of local anesthetics is accelerated by the addition of 1500 units. In Germany and the US 150 units are considered adequate for this purpose. The dosage differences notwithstanding (the dosage in the UK is ten times higher than in the US), no apparent differences in the safety profiles of animal-derived hyaluronidase products marketed in the US and UK, respectively, have been reported.

On Dec. 2, 2005, Halozyme Therapeutics Inc. received approval from the FDA for an injectable formulation of the recombinant human hyaluronidase, rHuPH20 (HYLENEX™). The FDA approved HYLENEX™ at a dose of 150 units for SC administration of the following indications:
 as an adjuvant to increase the absorption and dispersion of other injected drugs
 for hypodermoclysis
 as an adjunct in SC urography for improving resorption of radiopaque agents.

As part of that regulatory review it was established that rHuPH20 possesses the same properties of enhancing the dispersion and absorption of other injected drugs as the previously approved animal-derived hyaluronidase preparations, but with an improved safety profile. In particular, the use of recombinant human hyaluronidase (rHuPH20) compared with animal-derived hyaluronidases minimizes the potential risk of contamination with animal pathogens and transmissible spongiform encephalopathies.

Soluble Hyaloronidase glycoproteins (sHASEGP), a process for preparing the same and their use in pharmaceutical compositions have been described in WO 2004/078140.

The use of soluble Hyaloronidase glycoproteins in combination with a variety of exemplary antibodies, such as e.g. Trastuzumab, has been mentioned in WO 2006/091871.

The detailed experimental work as outlined further below has shown that the formulations of the present invention surprisingly have favorable storage stability and fulfill all necessary requirements for approval by the health authorities.

The hyaluronidase enzyme in the formulations of the present invention enhances the delivery of the anti-HER2 antibody to the systemic circulation, e.g. by increasing the absorption of the active substance (it acts as a permeation enhancer). The hyaluronidase enzyme also increases the delivery of the therapeutic anti-HER2 antibody into the systemic circulation via the subcutaneous application route by the reversible hydrolyzation of hyaluronan, an extracellular component of the SC interstitial tissue. The hydrolysis of hyaluronan in the hypodermis temporarily opens channels in the interstitial space of the SC tissue and thereby improves the delivery of the therapeutic anti-HER2 antibody into the systemic circulation. In addition, the administration shows reduced pain in humans and less volume-derived swelling of the SC tissue.

Hyaluronidase, when administered locally has its entire effect locally. In other word hyaluronidase is inactivated and metabolized locally in minutes and has not been noted to have systemic or long term effects. The rapid inactivation of hyaluronidase within minutes when it enters the blood stream precludes a realistic ability to perform comparable biodistribution studies between different hyaluronidase products. This property also minimizes any potential systemic safety concerns because the hyaluronidase product cannot act at distant sites.

The unifying feature of all hyaluronidase enzymes is their ability to depolymerize hyaluronan, regardless of differences in chemical structure, in species source, in tissue sources, or in the batches of drug product sourced from the same species and tissue. They are unusual in that their activity is the same (except for potency) in spite of having different structures.

The hyaluronidase enzyme excipient in accordance with the formulation of the present invention is characterized by having no adverse effect on the molecular integrity of the anti-HER2 antibody in the stable pharmaceutical formulation described herein. Furthermore, the hyaluronidase enzyme merely modifies the delivery of the anti-HER2 antibody to the systemic circulation but does not possess any properties that could provide or contribute to the therapeutic effects of systemically absorbed anti-HER2 antibody. The hyaluronidase enzyme is not systemically bioavailable and does not adversely affect the molecular integrity of the anti-HER2 antibody at the recommended storage conditions of the stable pharmaceutical formulation in accordance with the invention. It is therefore to be considered as an excipient in the anti-HER2 antibody formulation in accordance with this invention. As it exerts no therapeutic effect it represents a constituent of the pharmaceutical form apart from the therapeutically active anti-HER2 antibody.

A number of suitable hyaluronidase enzymes in accordance with the present invention are known from the prior art. The preferred enzyme is a human hyaluronidase enzyme, most preferably the enzyme known as rHuPH20. rHuPH20 is a member of the family of neutral and acid-active β-1,4 glycosyl hydrolases that depolymerize hyaluronan by the hydrolysis of the β-1,4 linkage between the $C_1$ position of N-acetyl glucosamine and the $C_4$ position of glucuronic acid. Hyaluronan is a polysaccharide found in the intracellular ground substance of connective tissue, such as the subcutaneous interstitial tissue, and of certain specialized tissues, such as the umbilical cord and vitreous humor. The hydrolysis of hyaluronan temporarily decreases the viscosity of the interstitial tissue and promotes the dispersion of injected fluids or of localized transudates or exudates, thus facilitating their absorption. The effects of hyaluronidase are local and reversible with complete reconstitution of the tissue hyaluronan occurring within 24 to 48 hours [Frost, G. I., "Recombinant human hyaluronidase (rHuPH20): an enabling platform for subcutaneous drug and fluid administration", Expert Opinion on Drug Delivery, 2007; 4:427-440]. The increase in the permeability of connective tissue through the hydrolysis of hyaluronan correlates with the efficacy of hyaluronidase for their capability to increase the dispersion and absorption of co-administered molecules.

The human genome contains several hyaluronidase genes. Only the PH20 gene product possesses effective hyaluronidase activity under physiologic extracellular conditions and acts as a spreading agent, whereas acid-active hyaluronidases do not have this property.

rHuPH20 is the first and only recombinant human hyaluronidase enzyme currently available for therapeutic use. Naturally occurring human PH20 protein has a lipid anchor attached to the carboxy terminal amino acid that anchors it to the plasma membrane. The rHuPH20 enzyme developed by Halozyme is a truncated deletion variant that lacks such amino acids in the carboxy terminus responsible for the lipid attachment. This gives rise to a soluble, neutral pH-active enzyme similar to the protein found in bovine testes preparations. The rHuPH20 protein is synthesized with a 35 amino acid signal peptide that is removed from the N-terminus during the process of secretion. The mature rHuPH20 protein contains an authentic N-terminal amino acid sequence orthologous to that found in some bovine hyaluronidase preparations.

The PH20 hyaluronidases, including the animal derived PH20 and recombinant human rHuPH20, depolymerize hyaluronan by the hydrolysis of the 0-1,4 linkage between the $C_1$ position of N-acetyl glucosamine and the C4 position of glucuronic acid. The tetrasaccharide is the smallest digestion product [Weissmann, B., "The transglycosylative action of testicular hyaluronidase", J. Biol. Chem., 1955; 216: 783-94]. This N-acetyl glucosamine/glucuronic acid structure is not found in N-linked glycans of recombinant biological products and therefore rHuPH20 will not affect the glycosylation of antibodies it is formulated with, such as e.g. Trastuzumab. The rHuPH20 enzyme itself possesses six N-linked glycans per molecule with core structures similar to that found in monoclonal antibodies. As anticipated, these N-linked structures do not change over time, confirming the lack of enzymatic activity of rHuPH20 on these N-linked glycan structures. The short half life of rHuPH20 and the constant synthesis of hyaluronan lead to a short and local action of the enzyme on tissues.

The hyaluronidase enzyme which is an excipient in the subcutaneous formulation in accordance with the present invention can be prepared by using recombinant DNA technology. In this way it is ensured that the same protein (identical amino acid sequence) is obtained all the time and that an allergic reaction, e.g. caused by contaminating proteins co-purified during extraction from a tissue, is avoided. The hyaluronidase enzyme used in the formulation as exemplified herein is a human enzyme, viz. rHuPH20.

The amino acid sequence of rHuPH20 (HYLENEX™) is well known and available under CAS Registry No. 75971-58-7. The approximate molecular weight is 61 kDa.

Multiple structural and functional comparisons have been performed between naturally sourced mammalian hyaluronidase and PH-20 cDNA clones from humans and other mammals. The PH-20 gene is the gene used for the recombinant product rHuPH20; however the recombinant drug product is a 447 amino acid truncated version of the full protein encoded by the PH-20 gene. Structural similarities with respect to amino acid sequences rarely exceed 60% in any comparison. Functional comparisons show that the activity of rHuPH20 is very similar to that of previously approved hyaluronidase products. This information is consistent with the clinical findings during the past 50 years that regardless of the source of the hyaluronidase, the clinical safety and efficacy of units of hyaluronidase are equivalent.

The use of rHuPH20 in the anti-HER2 antibody SC formulation in accordance with the present invention allows the administration of higher volumes of drug product and to potentially enhance the absorption of subcutaneously administered Trastuzumab into the systemic circulation.

The osmolality of the stable pharmaceutical formulation in accordance with the invention is 330±50 mOsm/kg.

The stable pharmaceutical formulation in accordance with the invention is essentially free from visible (human eye inspection) particles. The sub-visible particles (as measured by light obscuration) should fulfill the following criteria:
  maximum number of particles≥10 μm per vial→6000
  maximum number of particles≥25 μm per vial→600

In a further aspect the present invention provides the use of a formulation for the preparation of a medicament useful for treating a disease or disorder amenable to treatment with an anti-HER2 antibody such as e.g. cancer or a non-malignant disease in a subject comprising administering the formulation described herein to a subject in an amount effective to treat the said disease or disorder. The anti-HER2 antibody can be co-administered concomitantly or sequentially with a chemotherapeutic agent.

In a further aspect the present invention provides a method of treating a disease or disorder which is amenable to treatment with an anti-HER2 antibody (e.g. cancer or a non-malignant disease) in a subject comprising administering the formulation described herein to a subject in an amount effective to treat the said disease or disorder. The cancer or a non-malignant disease will generally involve HER2-expressing cells, such that the HER2 antibody in the therapeutic pharmaceutical SC formulation in accordance with the present invention is able to bind to the affected cells. Various cancer or a non-malignant diseases that can be treated with a formulation in accordance with the present invention are listed below.

The stable pharmaceutical formulation of the pharmaceutically active anti-HER2 antibody in accordance with the invention can be administered as subcutaneous injection, whereby the administration is repeated several times with time intervals of 3 weeks (q3w). The full volume of the injection fluid is in most cases administered within a time period of 1 to 10 minutes, preferably 2 to 6 minutes, most preferably 3±1 minutes. In adjuvant EBC patients and amongst patients with MBC receiving Trastuzumab monotherapy, where no other intravenous (IV) chemotherapeutic agents are given, such subcutaneous administration leads to increased patient convenience with the potential for self-administration at home. This leads to improved compliance and reduces/eliminates costs associated with IV administration (viz., nursing costs for IV administration, rental of day-beds, patient travel etc). Subcutaneous administration in accordance with the present invention will most likely be associated with a reduced frequency and/or intensity of infusion-related reactions.

The addition of the hyaluronidase to the formulation allows increasing the injection volume which can be safely and comfortably administered subcutaneously. Under normal circumstances the injection volume is 1 to 15 ml. It has been observed that the administration of the formulation in accordance with the present invention increases the dispersion, absorption and the bioavailability of the therapeutic antibody. Large molecules (i.e. >16 kDa) that are administered via the SC route are preferentially absorbed into the vascular compartment through the draining lymphatic fluids [Supersaxo, A., et al., "Effect of Molecular Weight on the Lymphatic Absorption of Water-Soluble Compounds Following Subcutaneous Administration", 1990; 2:167-169; Swartz, M. A., "Advanced Drug Delivery Review, The physiology of the lymphatic system", 2001; 50: 3-20]. The rate of introduction of these large molecules into the systemic circulation is thus slowed relative to intravenous infusion, therefore potentially resulting in reduced frequency/intensity of infusion related reactions.

The production of the subcutaneous Trastuzumab formulation in accordance with the invention requires high antibody concentrations (approx. 120 mg/ml) in the final step of purification of the manufacturing process. Therefore an additional process step (ultrafiltration/diafiltration) is added to the conventional manufacturing process of Trastuzumab. In accordance with the teachings in WO 97/04801 the highly concentrated, stable pharmaceutical anti-HER2 antibody formulation in accordance with the present invention can also be provided as stabilized protein formulation which can reconstituted with a suitable diluent to generate a high anti-HER2 antibody concentration reconstituted formulation.

The HER2 antibody SC formulation in accordance with this invention is mainly used to treat cancer. Whereby the terms "cancer" and "cancerous" refer to or describe the physiological condition in mammals that is typically characterized by unregulated cell growth. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

The term "about" as used in the present patent specification is meant to specify that the specific value provided may vary to a certain extent, such as e.g. means that variations in the range of ±10%, preferably ±5%, most preferably ±2% are included in the given value.

A cancer which "overexpresses" a HER receptor is one which has significantly higher levels of a HER receptor, such as HER2, at the cell surface thereof, compared to a noncancerous cell of the same tissue type. Such overexpression may be caused by gene amplification or by increased transcription or translation. HER receptor overexpression may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479), Southern blotting, or polymerase chain reaction (PCR) techniques, such as real time quantitative PCR (RT-PCR). One may also study HER receptor overexpression by measuring shed antigen (e.g., HER extracellular domain) in a biological fluid such as serum [see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., J. Immunol. Methods 1990; 132: 73-80]. Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which "does not overexpress HER2 receptor" is one which does not express higher than normal levels of HER2 receptor compared to a noncancerous cell of the same tissue type.

A cancer which "overexpresses" a HER ligand is one which produces significantly higher levels of that ligand compared to a noncancerous cell of the same tissue type. Such overexpression may be caused by gene amplification or by increased transcription or translation. Overexpression of the HER ligand may be determined diagnostically by evaluating levels of the ligand (or nucleic acid encoding it) in the patient, e.g. in a tumor biopsy or by various diagnostic assays such as the IHC, FISH, southern blotting, PCR or in vivo assays well known in the art.

It is contemplated that the HER2 antibody SC formulation in accordance with this invention may also be used to treat various non-malignant diseases or disorders, such a include autoimmune disease (e.g. psoriasis); endometriosis; scleroderma; restenosis; polyps such as colon polyps, nasal polyps or gastrointestinal polyps; fibroadenoma; respiratory disease; cholecystitis; neurofibromatosis; polycystic kidney disease; inflammatory diseases; skin disorders including psoriasis and dermatitis; vascular disease; conditions involving abnormal proliferation of vascular epithelial cells; gastrointestinal ulcers; Menetrier's disease, secreting adenomas or protein loss syndrome; renal disorders; angiogenic disorders; ocular disease such as age related macular degeneration, presumed ocular histoplasmosis syndrome, retinal neovascularization from proliferative diabetic retinopathy, retinal vascularization, diabetic retinopathy, or age related macular degeneration; bone associated pathologies such as osteoarthritis, rickets and osteoporosis; damage following a cerebral ischemic event; fibrotic or edemia diseases such as hepatic cirrhosis, lung fibrosis, carcoidosis, throiditis, hyperviscosity syndrome systemic, Osier Weber-Rendu disease, chronic occlusive pulmonary disease, or edema following burns, trauma, radiation, stroke, hypoxia or ischemia; hypersensitivity reaction of the skin; diabetic retinopathy and diabetic nephropathy; Guillain-Barre syndrome; graft versus host disease or transplant rejection; Paget's disease; bone or joint inflammation; photoaging (e.g. caused by UV radiation of human skin); benign prostatic hypertrophy; certain microbial infections including microbial pathogens selected from adenovirus, hantaviruses, *Borrelia burgdorferi*, *Yersinia* spp. and *Bordetella pertussis*; thrombus caused by platelet aggregation; reproductive conditions such as endometriosis, ovarian hyperstimulation syndrome, preeclampsia, dysfunctional uterine bleeding, or menometrorrhagia; synovitis; atheroma; acute and chronic nephropathies (including proliferative glomerulonephritis and diabetes-induced renal disease); eczema; hypertrophic scar formation; endotoxic shock and fungal infection; familial adenomatosis polyposis; neurodedenerative diseases (e.g. Alzheimer's disease, AIDS-related dementia, Parkinson's disease, amyotrophic lateral sclerosis, retinitis pigmentosa, spinal muscular atrophy and cerebellar degeneration); myelodysplastic syndromes; aplastic anemia; ischemic injury; fibrosis of the lung, kidney or liver; T-cell mediated hypersensitivity disease; infantile hypertrophic pyloric stenosis; urinary obstructive syndrome; psoriatic arthritis; and Hasimoto's thyroiditis. Exemplary non-malignant indications for therapy herein include psoriasis, endometriosis, scleroderma, vascular disease (e.g. restenosis, artherosclerosis, coronary artery disease, or hypertension), colon polyps, fibroadenoma or respiratory disease (e.g. asthma, chronic bronchitis, bronchieactasis or cystic fibrosis).

Where the indication is cancer, the patient may be treated with a combination of the antibody formulation, and a chemotherapeutic agent. The combined administration includes co-administration or concurrent administration, using separate formulations or a single pharmaceutical formulation, and consecutive administration in either order, wherein preferably there is a time period while both (or all) active agents simultaneously exert their biological activities. Thus, the chemotherapeutic agent may be administered prior to, or following, administration of the antibody formulation in accordance with the present invention. In this embodiment, the timing between at least one administration of the chemotherapeutic agent and at least one administration of the antibody formulation in accordance with the present invention is preferably approximately 1 month or less, and most preferably approximately 2 weeks or less. Alternatively, the chemotherapeutic agent and the antibody formulation in accordance with the present invention are administered concurrently to the patient, in a single formulation or separate formulations.

Treatment with the said antibody formulation will result in an improvement in the signs or symptoms of cancer or disease. For instance, where the disease being treated is cancer, such therapy may result in an improvement in survival (overall survival and/or progression free survival) and/or may result in an objective clinical response (partial or complete). Moreover, treatment with the combination of the chemotherapeutic agent and the antibody formulation may result in a synergistic or greater than additive, therapeutic benefit to the patient.

Normally the antibody in the formulation administered is a naked antibody. However, the antibody administered may be conjugated with a cytotoxic agent. The immunoconjugate and/or antigen to which it is bound is/are then internalized by the cell, resulting in increased therapeutic efficacy of the immunoconjugate in killing the cancer cell to which it binds. In one embodiment, the cytotoxic agent targets or interferes with nucleic acid in the cancer cell. Examples of such cytotoxic agents include maytansinoids, calioheamicins, ribonucleases and DNA endonucleases. The clinically most advanced immunoconjugates are Trastuzumab-maytansinoid immunoconjugates (T-DM1) as they are described in WO 2003/037992, in particular the immunoconjugate T-MCC-DM1, the chemical name of which is $N^{2'}$-deacetyl-$N^{2'}$-(3-mercapto-1-oxopropyl)-maytansine-4-maleimidomethyl-cyclohexyl-1-carboxyl-Trastuzumab.

For subcutaneous delivery, the formulation may be administered via a suitable device, such as (but not limited to) a syringe; an injection device (e.g. the INJECT-EASE™ and GENJECT™ device); an infusion pump (such as e.g. Accu-Chek™); an injector pen (such as the GENPEN™; an needleless device (e.g. MEDDECTOR™ and BIOJECTOR™); or via a subcutaneous patch delivery system. A suitable delivery system for the formulations in accordance with the present invention is described in WO 2010/029054. Such device comprises about 5 to about 15 ml or more particularly 5 ml of the liquid formulation in accordance with the present invention.

For the prevention or treatment of disease, the appropriate dosage of the antibody will depend on the type of disease to be treated, as defined above, the severity and course of the disease, whether the antibody is administered for preventive or therapeutic purposes, on the previous therapy, the patient's clinical history and his response to the antibody, and the discretion of the attending physician. The antibody is suitably administered to the patient at one time or over a series of treatments. Depending on the type and severity of the disease, about 1 μg/kg to 50 mg/kg of bodyweight or more specifically between about 0.1 mg/kg to 20 mg/kg of bodyweight) of the anti-HER2 antibody is a candidate initial dosage for administration to the patient, whether, for example, by one or more separate administrations, or by continuous infusion. More specifically the dosage of the antibody will be in the range from about 0.05 mg anti-HER2 antibody/kg of bodyweight to about 10 mg anti-HER2 antibody/kg of bodyweight. If a chemotherapeutic agent is administered, it is usually administered at dosages known therefore, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, MD (1992).

Other therapeutic regimens may be combined with the antibody including, but not limited to a second (third, fourth, etc) chemotherapeutic agent(s) (in another word a "cocktail" of different chemotherapeutic agents); another monoclonal antibody; a growth inhibitory agent; a cytotoxic agent; a chemotherapeutic agent; a EGFR-targeted drug; a tyrosine kinase inhibitor; an anti-angiogenic agent; and/or cytokine, etc.; or any suitable combination thereof.

In addition to the above therapeutic regimes, the patient may be subjected to surgical removal of cancer cells and/or radiation therapy.

In another embodiment of the invention, an article of manufacture is provided which contains the pharmaceutical formulation of the present invention and provides instructions for its use. This article of manufacture comprises a container. Suitable containers include, for example, bottles, vials (e.g. multiple or dual chamber vials), syringes (such as multiple or dual chamber syringes) and test tubes. The container may be formed from a variety of materials such as glass or plastic. The container holds the formulation and the label on, or associated with, the container may indicate directions for use. The container holding the formulation may be a multi-use vial, which allows for repeat administrations (e.g. from 2 to 6 administrations) of the reconstituted formulation. The article of manufacture may further include other materials desirable from a commercial and user standpoint, including other buffers, diluents, filters, needles, syringes, and package inserts with instructions for use.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

A "sterile" formulation is aseptic or free from all living microorganisms and their spores.

A "stable" formulation is one in which all the protein therein essentially retain their physical stability and/or chemical stability and/or biological activity upon storage at the intended storage temperature, e.g. 2-8° C. It is desired that the formulation essentially retains its physical and chemical stability, as well as its biological activity upon storage. The storage period is generally selected based on the intended shelf-life of the formulation. Furthermore, the formulation should be stable following freezing (to, e.g., −70° C.) and thawing of the formulation, for example following 1, 2 or 3 cycles of freezing and thawing. Various analytical techniques for measuring protein stability are available in the art and are reviewed in Peptide and Protein Drug Delivery, 247-301, Vincent Lee Ed., Marcel Dekker, Inc., New York, New York, Pubs. (1991) and Jones, A. Adv. Drug Delivery Rev. 10: 29-90 (1993), for example. Stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation changes, etc. A "deamidated" monoclonal antibody herein is one in which one or more asparagine residue thereof has been modified, e.g. to an aspartic acid or an iso-aspartic acid by a post-translational modification.

As used herein the term "buffering agent providing a pH of 5.5±2.0" refers to an agent which provides that the solution comprising it resists changes in pH by the action of its acid/base conjugate components. The buffer used in the formulations in accordance with the present invention has a pH in the range from about 5.0 to about 7.0, or from about 5.0 to about 6.5, or from about 5.3 to about 5.8. A pH of about 5.5 has to be found to be most suitable. Examples of buffering agents that will control the pH in this range include acetate, succinate, gluconate, histidine, citrate, glycylglycine and other organic acid buffers. The most suitable buffer in accordance with the present invention is a histidine buffer, such as e.g. L-histidine/HCl.

A "histidine buffer" is a buffer comprising the amino acid histidine. Examples of histidine buffers include histidine chloride, histidine acetate, histidine phosphate, histidine sulfate. The histidine buffer identified in the examples as being most suitable is a histidine chloride buffer. Such histidine chloride buffer is prepared by titrating L-histidine (free base, solid) with diluted hydrochloric acid. In particular the histidine buffer or histidine chloride buffer is at pH of 5.5±0.6, more particularly at a pH from about 5.3 to about 5.8, and most particularly has a pH of 5.5.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or freezing-point depression type osmometer.

A "saccharide" herein comprises the general composition $(CH_2O)_n$ and derivatives thereof, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, etc. Particularly the formulations described herein comprise a non-reducing disaccharide as a stabilizing agent, such as a saccharide selected from the group of trehalose (e.g. in the form of α,α-trehalose dihydrate) and sucrose.

Herein, a "surfactant" refers to a surface-active agent, e.g. a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQU AT™ series (Mona Industries, Inc., Paterson, New Jersey); polyethyl glycol, polypropyl glycol, and copolymers of ethylene and propylene glycol (e.g. Pluronics, PF68 etc); etc. Polysorbate 20 (PS20) and Polysorbate 80 (PS80), respectively have been found to be particularly suitable in the formulations described herein.

The term "antibody" herein is used in the broadest sense and specifically covers full length monoclonal antibodies, polyclonal antibodies, multispecific antibodies (e.g. bispecific antibodies) formed from at least two full length antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al, Nature, 256:495 (1975), or may be made by recombinant DNA methods (see, e.g., U.S. Pat. No. 4,816,567). The "monoclonal antibodies" may also be isolated from phage antibody libraries using the techniques described in Clarkson et al., Nature, 352:624-628 (1991) and Marks et al., J. Mol. Biol., 222:581-597 (1991).

An "antibody fragment" comprises a portion of a full length antibody, in particular comprises the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

A "full length antibody" is one which comprises an antigen-binding variable region as well as a light chain constant domain (CL) and heavy chain constant domains, CH1, CH2 and CH3. The constant domains may be native sequence constant domains (e.g. human native sequence constant domains) or amino acid sequence variants thereof. In particular the full length antibody has one or more effector functions.

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include acidic variant (e.g. deamidated antibody variant), basic variant, the antibody with an amino-terminal leader extension (e.g. VHS-) on one or two light chains thereof, antibody with a C-terminal lysine residue on one or two heavy chains thereof, etc, and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moieties attached thereto which differ from one or more carbohydrate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations. Moreover the term "glycosylation variant" includes also glycoengineered antibodies such as those described in EP 1,331,266 and U.S. Pat. No. 7,517,670.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc.

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α [alpha], δ [delta], ε [epsilon], γ [gamma], and μ [mu], respectively. The subunit structures and three-dimensional configurations of different classes of immunoglobulins are well known.

Herein, "biological activity" of a monoclonal antibody refers to the ability of the antibody to bind to antigen and result in a measurable biological response which can be measured in vitro or in vivo. Such activity may be antagonistic (for example where the antibody is a HER2 antibody) or agonistic. In the case of Pertuzumab, in one embodiment, the biological activity refers to the ability of the formulated antibody to inhibit proliferation of the human breast cancer cell line MDA-MB-175-VII.

The term "monoclonal antibodies" herein specifically include the so-called chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or Trastuzumab (HERCEPTIN™) as described in Table 3 of U.S. Pat. No. 5,821,337; humanized 520C9 (WO93/21319) and humanized 2C4 antibodies, such as Pertuzumab as described further herein below.

For the purposes herein, "Trastuzumab", "HERCEPTIN™" and "huMAb4D5-8" refer to an anti-HER2 antibody directed against the 4D5 epitope. Such antibody preferably comprises the light and heavy chain amino acid sequences disclosed e.g. in FIG. 14 of WO 2006/044908.

The "epitope 4D5" is the region in the extracellular domain of HER2 to which the antibody 4D5 (ATCC CRL 10463) and Trastuzumab bind. This epitope is close to the transmembrane domain of HER2, and within Domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive, of HER2). The "epitope 7C2/7F3" is the region at the amino terminus, within Domain I, of the extracellular domain of HER2 to which the 7C2 and/or 7F3 antibodies bind. To screen for antibodies which bind to the 7C2/7F3 epitope, a routine cross-blocking assay such as that described in "Antibodies, A Laboratory Manual" (Cold Spring Harbor Laboratory, Ed Harlow and David Lane (1988)) can be performed. Alternatively, epitope mapping can be performed to establish whether the antibody binds to the 7C2/7F3 epitope on HER2 (e.g. any one or more of residues in the region from about residue 22 to about residue 53 of HER2).

Figure 2:
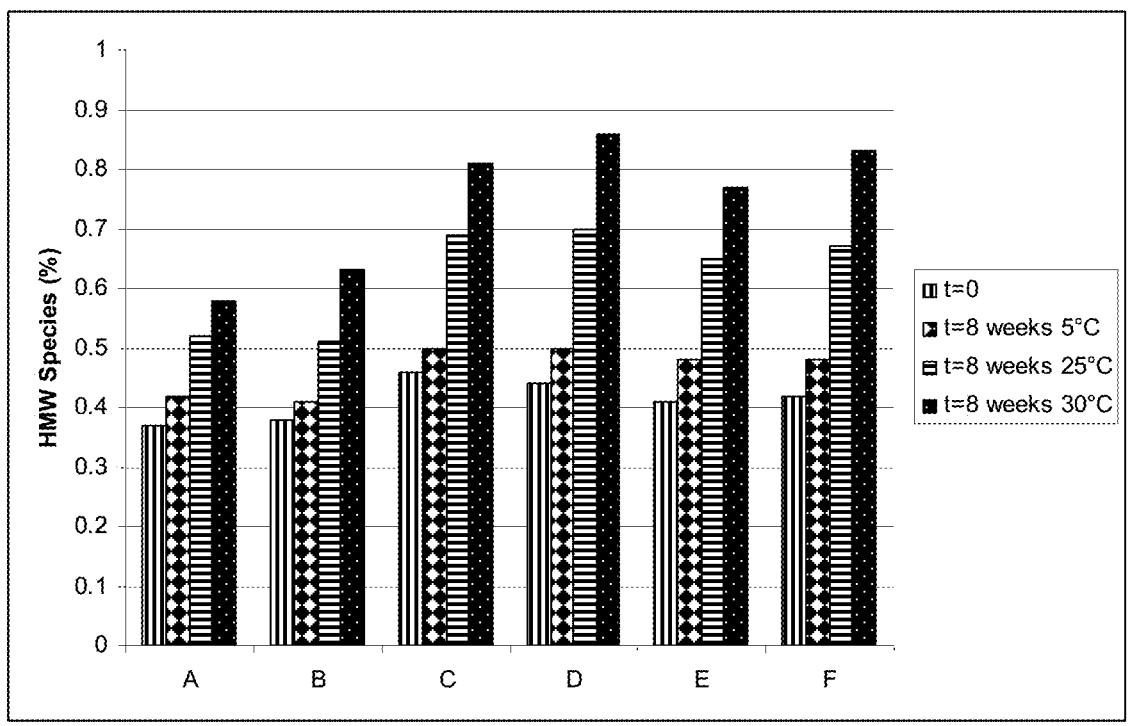
FIG. 2 shows stability of the formulations A to F (see Table 1 below) after 8 weeks with respect to High Molecular Weight (HMW) Species detected by Size Exclusion-HPLC. As shown in this figure the formulations A and B that contain trehalose without the addition of sodium chloride show a smaller increase of HMWs after 8 weeks storage time.
Figure 3:
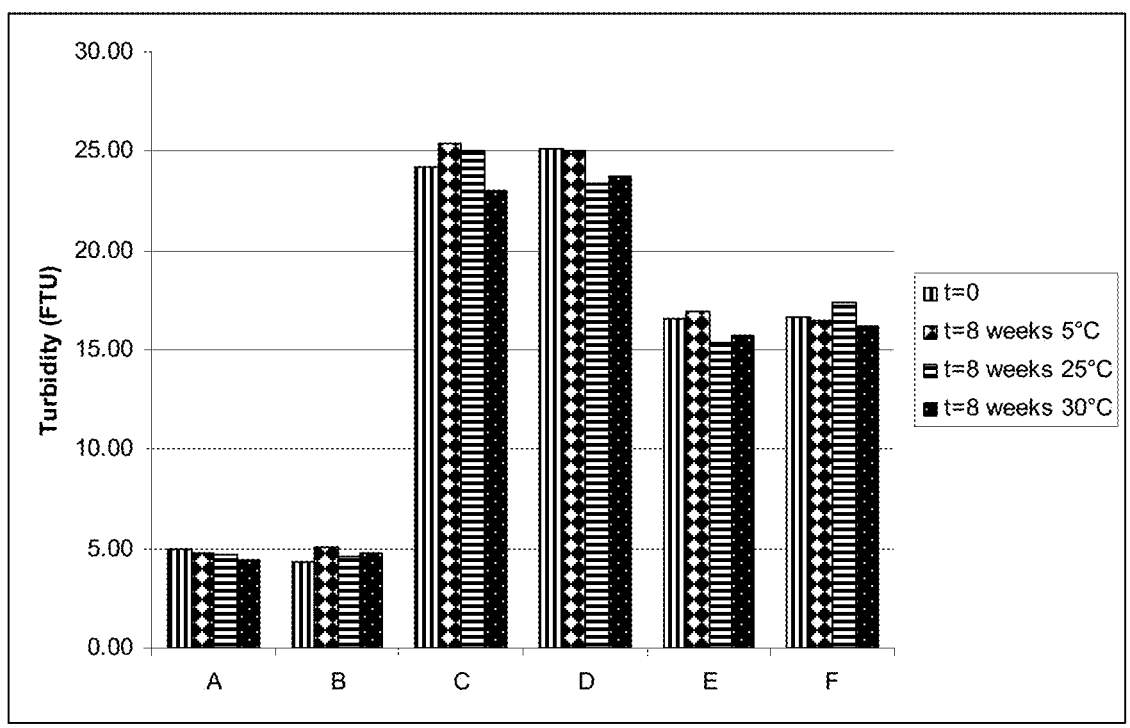
FIG. 3 shows stability after 8 weeks with respect to turbidity. As shown in this figure trehalose containing formulations A and B show a low turbidity; whereas NaCl containing formulations C to F show a much higher turbidity. Formulations E and F containing trehalose as well as NaCl showed an intermediate turbidity. No significant increase was observed upon storage for 8 weeks.
Figure 4:
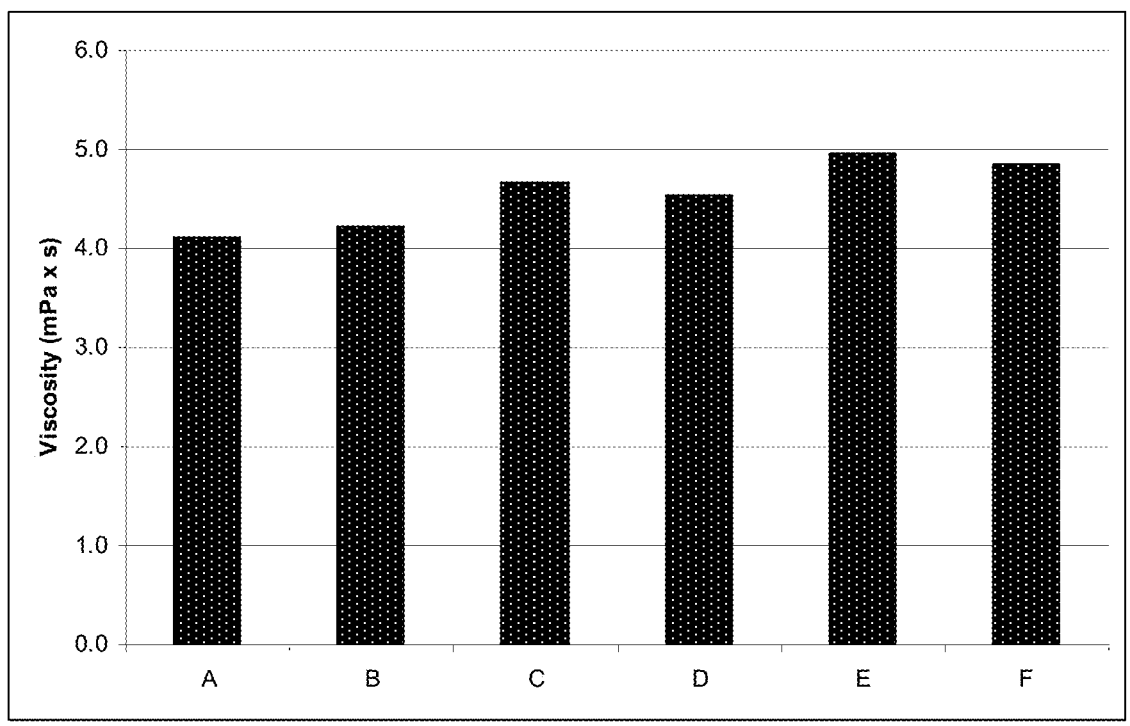
FIG. 4 shows viscosity of liquid formulations A to F (see Table 1 below) as measured by using plate-cone viscosimetry at ambient temperature. All formulations are in a low viscosity range that allow for subcutaneous injection.

Herein, "Pertuzumab" and "rhuMAb 2C4" refer to an antibody that binds to the 2C4 epitope and preferably comprising the variable light and variable heavy amino acid sequences disclosed in WO 2006/044908, more particularly the humanized 2C4 version 574 disclosed in FIG. 2 of WO 2006/044908.

The "epitope 2C4" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. 2C4 and Pertuzumab bind to the extracellular domain of HER2 at the junction of domains I, II and III (Franklin et al. Cancer Cell 5:317-328 (2004)).

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in "The Molecular Basis of Cancer", Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g. from about 50% to about 100%) at an antibody concentration of about 0.5 to 30 g/ml, where the growth inhibition is determined six days after exposure of the SK-BR-3 cells to the antibody (see U.S. Pat. No. 5,677,171 issued Oct. 14, 1997). The preferred growth inhibitory antibody is a humanized variant of murine monoclonal antibody 4D5, e.g., Trastuzumab.

"Treatment" refers to both therapeutic treatment and prophylactic or preventative measures. Those in need of treatment include those already with the disease as well as those in which the disease is to be prevented. Hence, the patient to be treated herein may have been diagnosed as having the disease or may be predisposed or susceptible to the disease.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelarnine; acetogenins (especially bullatacin and bullatacinone); delta-9-tetrahydrocannabinol (dronabinol, MARENOL™); beta-lapachone; lapachol; colchicines; betulinic acid; a camptothecin (including the synthetic analogue topotecan (HYCAMTIN™), CPT-11 (irinotecan, C AMPTOSAR™), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptoplhycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfa[pi]nide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma 11 and calicheamicin omega 11 (see, e.g., Angew, Chemie Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN™, morpholino-doxorubicin, cyanomorpholino-doxorubicin, 2-pyrrolino-doxorubicin, doxorubicin HCl liposome injection (DOXIL™), liposomal doxorubicin TLC D-99 (MYOCET™), peglylated liposomal doxorubicin (CAELYX™) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR™), tegafur (UFTORAL™), capecitabine (XELODA™), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSKL™ polysaccharide complex (JHS Natural Products, Eugene, OR); razoxane; rhizoxin; sizofiran; spirogermaraium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL™), albumin-engineered nanoparticle formulation of paclitaxel (ABRAXANE™), and docetaxel (TAXOTERE™); chloranbucil; 6-thioguanine; mercaptopurine; metliotrexate; platinum agents such as cisplatin, oxaliplatin, and carboplatin; vincas, which prevent tubulin polymerization from forming microtubules, including vinblastine (VELBAN™), vincristine (ONCOVIN™), vindesine (ELDISINE™), FILDESIN™), and vinorelbine (NAVELBINE™)); etoposide (VP-16); ifosfamide; mitoxantrone; leucovovin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN™); bisphosphonates such as clodronate (for example, BONEFOS™ or OSTAC™), etidronate (DIDROCAL™) NE-58095, zoledronic acid/zoledronate (ZOMETA™), alendronate (FOSAMAJX™) pamidronate (AREDIA™), tiludronate (SKELID™), or risedronate (ACTONEL™; troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE™ vaccine and gene therapy vaccines, for example, ALLOVECTIN™ vaccine, LEUVECTIN™ vaccine, and VAXID™ vaccine; topoisomerase 1 inhibitor (e.g., LURTOTECAN™; rmRH (e.g., ABARELIX™); BAY439006 (sorafenib; Bayer); SU-11248 (Pfizer); perifosine, COX-2 inhibitor (e.g. celecoxib or etoricoxib), proteosome inhibitor (e.g. PS341); bortezomib (VELCADE™); CCI-779; tipifarnib (RI 1577); orafenib, ABT510; Bcl-2 inhibitor such as oblimersen sodium (GENASENSE™); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate or inhibit hormone action on tumors such as anti-estrogens with mixed agonist/antagonist profile, including, tamoxifen (NOLVADEX™), 4-hydroxytamoxifen, toremifene (FARESTON™), idoxifene, droloxifene, raloxifene (EVTSTA™), trioxifene, keoxifene, and selective estrogen receptor modulators (SERMs) such as SERM3; pure anti-estrogens without agonist properties, such as fulvestrant (FASLODEX™), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN™), and nonsteroidal aromatase inhibitors such as anastrazole (ARIMIDEX™), letrozole (FEMARA™) and aminoglutethimide, and other aromatase inhibitors including vorozole (RIVISOR™) megestrol acetate (MEGASE™), fadrozole, imidazole; lutenizing hormone-releasing hormone agonists, including leuprolide (LUPRON™ and ELIGARD™), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; testolactone; and pharmaceutically acceptable salts, acids or derivatives of any of the above; as well as combinations of two or more of the above.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX™) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix). The anti-EGFR antibody may be conjugated with a cytotoxic agent, thus generating an immunoconjugate (see, e.g., EP-A-659439, Merck Patent GmbH). Examples of small molecules that bind to EGFR include ZD 1839 or Gefitinib (IRESSA™; Astra Zeneca), CP-358774 or Erlotinib HCl (TARCEVA™ Genentech/Roche/OSI) and AG1478, AG1571 (SU 5271; Sugen)

A "tyrosine kinase inhibitor" is a molecule which inhibits to some extent tyrosine kinase activity of a tyrosine kinase such as a HER receptor. Examples of such inhibitors include the EGFR-targeted drugs noted in the preceding paragraph as well as small molecule HER2 tyrosine kinase inhibitor such as TAK1 65 available from Takeda, dual-HER inhibitors such as EKB-569 (available from Wyeth) which preferentially binds EGFR but inhibits both HER2 and EGFR-overexpressing cells, GW572016 (available from Glaxo) an oral HER2 and EGFR tyrosine kinase inhibitor, and PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (Gleevec™) available from Novartis; MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-IC11 (Imclone); or as described in any of the following patent publications: U.S. Pat. No. 5,804,396; WO99/09016 (American Cyanamid); WO98/43960 (American Cyanamid); WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to Vascular Endothelial Growth Factor (VEGF), such as Bevacizumab (AVASTIN™).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone, parathyroid hormone, thyroxine, insulin, proinsulin, relaxin; prorelaxin, glycoprotein hormones such as follicle stimulating hormone (FSH), thyroid stimulating hormone (TSH), and luteinizing hormone (LH), hepatic growth factor; fibroblast growth factor, prolactin, placental lactogen, tumor necrosis factor α and β, mullerian-inhibiting substance, mouse gonadotropin-associated peptide, inhibin; activin, vascular endothelial growth factor, integrin, thrombopoietin (TPO), nerve growth factors such as NGF-β, platelet-growth factor; transforming growth factors (TGFs) such as TGF-α and TGF-β, insulin-like growth factor-I and -II, erythropoietin (EPO), osteoinductive factors; interferons such as interferon-α, β, and -γ, colony stimulating factors (CSFs) such as macrophage-CSF (M-CSF), granulocyte-macrophage-CSF (GM-CSF), and granulocyte-CSF (G-CSF), interleukins (ILs) such as IL-1, IL-la, IL-2, IL-3, IL-4, IL-5, IL-6, IL-7, IL-8, IL-9, IL-10, IL-11, IL-12, a tumor necrosis factor such as TNF-α or TNF-β, and other polypeptide factors including LIF and kit ligand (KL). As used herein, the term cytokine includes proteins from natural sources or from recombinant cell culture and biologically active equivalents of the native sequence cytokines.

The term "effective amount" refers to an amount which provides the desired effect.

In the case of a formulation ingredient such as the hyaluronidase enzyme in accordance with the present invention an effective amount is the amount necessary to increase the dispersion and absorption of the co-administered anti-HER2 antibody in such a way that the anti-HER2 antibody can act in a therapeutically effective way as outlined above. In the case of a pharmaceutical drug substance it is the amount of active ingredient effective to treat a disease in the patient. Where the disease is cancer, the effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival, result in an objective response (including a partial response, PR, or complete response, CR), increase overall survival time, and/or improve one or more symptoms of cancer.

The antibody which is formulated in accordance with the present invention is preferably essentially pure and desirably essentially homogeneous (i.e. free from contaminating proteins etc, whereby the hyaluronidase enzyme in the formulation in accordance of this invention is not to be considered to be a contaminating protein of the anti-HER2 monoclonal antibody in accordance of the present invention). An "essentially pure" antibody means a composition comprising at least about 90% by weight of the antibody, based on total weight of the composition, preferably at least about 95% by weight. An "essentially homogeneous" antibody means a composition comprising at least about 99% by weight of antibody, based on total weight of the composition.

The invention will be more fully understood by reference to the following Examples. They should not, however, be construed as limiting the scope of the invention. All literature and patent citations are incorporated herein by reference.

The Examples are further illustrated by the appended FIGS. 1-4.

EXAMPLES

The anti-HER2 formulations for subcutaneous administration according to the invention were developed based on the experimental results as provided below using the general preparatory and analytical methods and assays as outlined below.

A) Preparation of the Components for the Formulation

Trastuzumab is manufactured by techniques generally known for the production of recombinant proteins. A genetically engineered Chinese hamster ovary (CHO) cell line prepared as described in EP-B-590058 is expanded in cell culture from a master cell bank. The Trastuzumab monoclonal antibody is harvested from the cell culture fluid and purified using immobilized Protein A affinity chromatography, cation exchange chromatography (e.g. SP-Sepharose FF), a filtration step to remove viral contaminations (e.g. a PVDF membrane (sold by Milipore under the name Viresolve filters), followed by anion exchange chromatography (e.g. Q-Sepharose FF) and an ultrafiltration/diafiltration step. For preparing the formulations in accordance with these examples the Trastuzumab was provided at a concentration of approx. 100 mg/ml in a 20 mM histidine buffer at a pH of approximately 6.0.

rHuPH20 is manufactured by techniques generally known from the production of recombinant proteins. The process begins with thawing of cells from the working cell bank (WCB) or master cell bank (MCB) and expansion through cell culture in a series of spinner flasks followed by expansion in a bioreactor. After completion of the production phase, the cell culture liquid is clarified by filtration, and is then treated with solvent/detergent to inactivate viruses. The protein is then purified by a series of column chromatography processes to remove process and product related impurities. A viral filtration step is performed, and the filtered bulk is then concentrated, formulated into the final buffer: 10 mg/mL rHuPH20 in 20 mM L-histidine/HCl buffer, pH 6.5, 130 mM NaCl, 0.05% (w/v) polysorbate 80. The rHuPH20 bulk is stored below $-70°$ C.

The other excipients of the formulation in accordance with the present invention are widely used in the practice and known to the person skilled in the art. There is therefore no need to be explained them here in detail.

Liquid drug product formulations for subcutaneous administration according to the invention were developed as follows.

Example 1: Preparation of the Liquid Formulations

For the preparation of the liquid formulations Trastuzumab was buffer-exchanged against a diafiltration buffer containing the anticipated buffer composition and, when required, concentrated by diafiltration to an antibody concentration of approx. 150 mg/ml. After completion of the diafiltration operation, the excipients (e.g. trehalose, rHuPH20) were added as stock solutions to the antibody solution. The surfactant was then added as a 50 to 200-fold stock solution. Finally the protein concentration was adjusted with a buffer to the final Trastuzumab concentration of about 110 mg/ml, 120 mg/ml or 130 mg/ml as specified in the particular formulations further below.

All formulations were sterile-filtered through 0.22 µm low protein binding filters and aseptically filled into sterile 6 ml glass vials closed with ETFE (Copolymer of ethylene and tetrafluoroethylene)-coated rubber stoppers and alucrimp caps. The fill volume was approx. 3.0 ml. These formulations were stored at different climate conditions (5° C., 25° C. and 30° C.) for different intervals of time and stressed by shaking (1 week at a shaking frequency of 200 $min^{-1}$ at 5° C. and 25° C.) and freeze-thaw stress methods. The samples were analyzed before and after applying the stress tests by the following analytical methods:

1) UV spectrophotometry;
2) Size Exclusion Chromatography (SEC);
3) by Ion exchange chromatography (IEC);
4) by turbidity of the solution;
5) for visible particles; and
6) for rHuPH20 activity.

UV spectroscopy, used for determination of protein content, was performed on a Perkin Elmer λ35 UV spectrophotometer in a wavelength range from 240 nm to 400 nm. Neat protein samples were diluted to approx. 0.5 mg/ml with the corresponding formulation buffer. The protein concentration was calculated according to Equation 1.

$$\text{Protein content} = \frac{A(280) - A(320) \times dil.\text{ factor}}{\varepsilon \langle cm^2/mg \rangle \times d \langle cm \rangle} \qquad \text{Equation 1}$$

The UV light absorption at 280 nm was corrected for light scattering at 320 nm and multiplied with the dilution factor, which was determined from the weighed masses and densities of the neat sample and the dilution buffer. The numerator was divided by the product of the cuvette's path length d and the extinction coefficient ε.

Size Exclusion Chromatography (SEC) was used to detect soluble high molecular weight species (aggregates) and low molecular weight hydrolysis products (LMW) in the formulations. The method was performed on a Waters Alliance 2695 HPLC instrument with a Waters W2487 Dual Absorbance Detector and equipped with 2 TosoHaas TSK Gel SuperSW3000, 4,6×300 mm columns in row. Intact monomer, aggregates and hydrolysis products were separated by an isocratic elution profile, using 50 mM sodium phosphate, 420 mM sodium perchlorate, pH 7.0 as mobile phase, and were detected at a wavelength of 280 nm.

Ion Exchange Chromatography (IEC) was performed to detect chemical degradation products altering the net charge of Trastuzumab in the formulations. For this purpose Trastuzumab was digested with Carboxpeptidase B. The method used a suitable HPLC instrument equipped with a UV detector (detection wavelength 214 nm) and a Dionex ProPac™ WCX-10 Analytical cation-exchange column (4×250 mm). 10 mM sodium phosphate buffer pH 7.5 in $H_2O$ and 10 mM sodium phosphate buffer pH 7.5 and 100 mM NaCl were used as mobile phases A and B, respectively, with a flow rate of 0.8 ml/min.

For the determination of the turbidity, opalescence was measured in FTU (turbidity units) using a HACH 2100AN turbidimeter at room temperature.

Samples were analyzed for visible particles by using a Seidenader V90-T visual inspection instrument.

An in vitro enzyme assay of rHuPH20 as hyaluronidase was used as activity assay. The assay is based on the formation of an insoluble precipitate when hyaluronan (sodium hyaluronate) binds to a cationic precipitant. Enzyme activity was measured by incubating rHuPH20 with hyaluronan substrate and then precipitating the undigested hyaluronan with acidified serum albumin (horse serum). The turbidity was measured at a wavelength of 640 nm and the decrease in turbidity resulting from enzyme activity on the hyaluronan substrate is a measure of the enzyme activity. The procedure is run using a standard curve generated with dilutions of rHuPH20 assay reference standard, and sample activity is read from the curve.

Further experiments were performed including following variations:
- variations in pH from about approx. 5.0 to approx. 6.0
- variations in protein content from about approx. 110 mg/ml to approx. 130 mg/ml
- variations in surfactant from approx. 0.02% to approx. 0.06%
- variations in stabilizer (methionine) from about 5 mM to about 15 mM The compositions and the results of the stability testing for the liquid anti-HER-2 drug product formulations (Formulations A to X) are provided in Table 1 below wherein the following abbreviations are used:
  ffp: =free from particles; effp: =essentially free from particles; wafp: =with a few particles
  F/T: =freezing/thawing; skg: =shaking; nd: =not determined The formulations specified below show that it is possible to provide liquid formulations with high concentrations of two different proteins. Such formulations can be prepared with greater ease and lower costs than lyophilized formulations. Moreover such formulations are easier to handle as no dissolving of the lyophilized final product (reconstitution) is required (ready to use). It has been found that the formulations specified in Tables 1, 3 and 4 are also suitable for the formulation of highly concentrated, stable pharmaceutical formulation of pharmaceutically active anti-HER2 antibodies lacking the hyaluronidase enzyme. Therefore, in one aspect the present invention relates also to formulations having the specified ingredients but lacking the hyaluronidase enzyme.

TABLE 1

Composition and stability data of liquid anti-HER2 drug product formulations according to this invention

| Storage condition | Storage Time | Protein concentration (mg/ml) | Size Exclusion-HPLC | | | Ion Exchange-HPLC | | | Turbidity (FTU) | Visible particles | HE activity (U/ml) |
| --- | --- | --- | --- | --- | --- | --- | --- | --- | --- | --- | --- |
| | | | HMW (%) | Monomer (%) | LMW (%) | Main Peak (%) | Peak 1 (%) | Peak 4 (%) | | | |

Formulation A is a liquid formulation with the composition 120 mg/ml Trastuzumab, 20 mM L-histidine/HCl pH 5.5, 210 mM α,α-trehalose dihydrate, 10 mM methionine, 0.04% polysorbate 20, 12'000 U/ml rHuPH20.

| | | | | | | | | | | | |
| --- | --- | --- | --- | --- | --- | --- | --- | --- | --- | --- | --- |
| — | Initial | 111 | 0.4 | 98.9 | 0.7 | 60 | 15 | 10 | 5.0 | ffp | 13613 |
| Skg 5° C. | 1 week | nd | 0.4 | 98.7 | 0.9 | Nd | nd | nd | 5.2 | ffp | 13775 |
| Skg 25° C. | 1 week | nd | 0.4 | 98.7 | 0.9 | 60 | 11 | 12 | 5.7 | ffp | 12053 |
| F/T | (5 cycles) | nd | 0.4 | 98.7 | 0.9 | Nd | nd | nd | 6.0 | effp | 12558 |
| 5° C. | 8 weeks | 105 | 0.4 | 98.5 | 1.1 | 60 | 15 | 11 | 4.8 | ffp | 13204 |
| | 21 weeks | nd | 0.4 | 98.7 | 0.8 | 62 | 12 | 11 | 5.3 | ffp | 14940 |
| | 36 weeks | nd | 0.4 | 98.7 | 0.8 | 59 | 11 | 12 | 3.8 | ffp | 12613 |
| 25° C. | 8 weeks | 106 | 0.5 | 98.3 | 1.2 | 53 | 8 | 19 | 4.7 | ffp | 12176 |
| | 21 weeks | nd | 0.6 | 97.7 | 1.7 | 42 | 7 | 26 | 5.2 | ffp | 13976 |
| | 36 weeks | nd | 0.7 | 97.2 | 2.1 | 33 | 7 | 34 | 3.8 | ffp | 12348 |
| 30° C. | 8 weeks | 105 | 0.6 | 97.8 | 1.6 | 45 | 6 | 26 | 4.4 | ffp | 13294 |
| | 21 weeks | 107 | 0.8 | 96.3 | 2.9 | 33 | 6 | 25 | 5.5 | ffp | nd |

Formulation B is a liquid formulation with the composition 120 mg/ml Trastuzumab, 20 mM L-histidine/HCl pH 5.5, 210 mM α,α-trehalose dihydrate, 10 mM methionine, 0.06% polysorbate 80, 12'000 U/ml rHuPH20.

| | | | | | | | | | | | |
| --- | --- | --- | --- | --- | --- | --- | --- | --- | --- | --- | --- |
| — | Initial | 111 | 0.4 | 98.9 | 0.7 | 59 | 15 | 10 | 4.4 | ffp | 13293 |
| Skg 5° C. | 1 week | nd | 0.4 | 98.7 | 0.9 | Nd | nd | nd | 5.2 | ffp | 13530 |
| Skg 25° C. | 1 week | nd | 0.4 | 98.7 | 0.8 | 61 | 12 | 12 | 5.2 | ffp | 9390 |
| F/T | (5 cycles) | nd | 0.4 | 98.7 | 0.9 | Nd | nd | nd | 5.5 | ffp | 12532 |
| 5° C. | 8 weeks | 109 | 0.4 | 98.7 | 0.9 | 60 | 15 | 11 | 5.1 | ffp | 13508 |
| | 21 weeks | nd | 0.5 | 98.8 | 0.8 | Nd | nd | nd | 5.3 | ffp | nd |
| | 36 weeks | nd | 0.4 | 98.8 | 0.8 | Nd | nd | nd | 4.5 | ffp | nd |
| 25° C. | 8 weeks | 109 | 0.5 | 98.2 | 1.3 | 53 | 8 | 19 | 4.6 | ffp | nd |
| | 21 weeks | nd | 0.7 | 97.6 | 1.8 | Nd | nd | nd | 5.2 | effp | nd |
| | 36 weeks | nd | 0.8 | 97.1 | 2.1 | Nd | nd | nd | 5.3 | ffp | nd |
| 30° C. | 8 weeks | 109 | 0.6 | 97.7 | 1.7 | 45 | 6 | 26 | 4.8 | ffp | 13394 |
| | 21 weeks | 107 | 0.9 | 96.2 | 2.9 | Nd | nd | nd | 5.3 | ffp | nd |

Formulation C is a liquid formulation with the composition 120 mg/ml Trastuzumab, 20 mM L-histidine/HCL pH 5.5, 130 mM sodium chloride, 10 mM methionine, 0.04% polysorbate 20, 12'000 U/ml rHuPH20.

| | | | | | | | | | | | |
| --- | --- | --- | --- | --- | --- | --- | --- | --- | --- | --- | --- |
| — | Initial | 129 | 0.5 | 98.8 | 0.7 | 59 | 15 | 10 | 24.2 | ffp | 12355 |
| Skg 5° C. | 1 week | nd | 0.5 | 98.6 | 0.9 | Nd | nd | nd | 26.0 | ffp | 13123 |
| Skg 25° C. | 1 week | nd | 0.5 | 98.5 | 0.9 | 60 | 12 | 11 | 25.3 | ffp | 12209 |
| F/T | (5 cycles) | nd | 0.5 | 98.6 | 0.9 | Nd | nd | nd | 24.8 | ffp | 12576 |
| 5° C. | 8 weeks | 126 | 0.5 | 98.7 | 0.8 | 60 | 15 | 11 | 25.4 | ffp | 12463 |
| | 21 weeks | nd | 0.6 | 98.4 | 1.0 | 62 | 13 | 9 | 23.6 | ffp | 15409 |
| | 36 weeks | nd | 0.6 | 98.6 | 0.8 | 59 | 12 | 12 | 26.3 | ffp | 13218 |
| 25° C. | 8 weeks | 125 | 0.7 | 98.0 | 1.3 | 54 | 9 | 18 | 25.0 | ffp | 13038 |
| | 21 weeks | nd | 0.9 | 97.5 | 1.6 | 42 | 9 | 22 | 24.3 | ffp | 14972 |
| | 36 weeks | nd | 1.0 | 97.0 | 2.1 | 32 | 9 | 31 | 25.7 | ffp | 12028 |

TABLE 1-continued

Composition and stability data of liquid anti-HER2 drug product formulations according to this invention

| | | | | | | | | | | | |
|---|---|---|---|---|---|---|---|---|---|---|---|
| 30° C. | 8 weeks | 125 | 0.8 | 97.6 | 1.6 | 46 | 8 | 25 | 23.0 | ffp | 12751 |
| | 21 weeks | 125 | 1.2 | 96.3 | 2.6 | 32 | 8 | 29 | 25.7 | ffp | nd |

Formulation D is a liquid formulation with the composition 120 mg/ml Trastuzumab, 20 mM L-histidine/HCl pH 5.5, 130 mM sodium chloride, 10 mM methionine, 0.06% polysorbate 80, 12'000 U/ml rHuPH20.

| | | | | | | | | | | | |
|---|---|---|---|---|---|---|---|---|---|---|---|
| — | Initial | 128 | 0.4 | 98.9 | 0.7 | 59 | 15 | 10 | 25.1 | ffp | 15178 |
| Skg 5° C. | 1 week | Nd | 0.5 | 98.6 | 0.9 | Nd | nd | nd | 24.1 | effp | 12201 |
| Skg 25° C. | 1 week | Nd | 0.6 | 98.5 | 0.9 | 60 | 12 | 11 | 25.4 | effp | 8311 |
| F/T | (5 cycles) | Nd | 0.5 | 98.6 | 0.9 | Nd | nd | nd | 24.8 | effp | 11906 |
| 5° C. | 8 weeks | 125 | 0.5 | 98.7 | 0.8 | 60 | 15 | 11 | 25.0 | ffp | 13238 |
| | 21 weeks | Nd | 0.6 | 98.5 | 1.0 | Nd | nd | nd | 24.3 | ffp | nd |
| | 36 weeks | Nd | 0.6 | 98.6 | 0.8 | Nd | nd | nd | 26.1 | ffp | nd |
| 25° C. | 8 weeks | 125 | 0.7 | 98.1 | 1.2 | 54 | 9 | 18 | 23.4 | ffp | 12661 |
| | 21 weeks | Nd | 0.9 | 97.3 | 1.8 | Nd | nd | nd | 24.5 | ffp | nd |
| | 36 weeks | Nd | 1.1 | 96.8 | 2.1 | Nd | nd | nd | 26.6 | ffp | nd |
| 30° C. | 8 weeks | 124 | 0.9 | 97.5 | 1.7 | 45 | 8 | 25 | 23.7 | ffp | 12182 |
| | 21 weeks | 125 | 1.3 | 96.1 | 2.6 | Nd | nd | nd | 24.2 | effp | nd |

Formulation E is a liquid formulation with the composition 120 mg/ml Trastuzumab, 20 mM L-histidine/HCl pH 5.5, 105 mM α,α-trehalose dihydrate, 65 mM sodium chloride, 10 mM methionine, 0.04% polysorbate 20, 12'000 U/ml rHuPH20.

| | | | | | | | | | | | |
|---|---|---|---|---|---|---|---|---|---|---|---|
| — | Initial | 128 | 0.4 | 98.9 | 0.7 | 59 | 15 | 10 | 16.6 | ffp | 13475 |
| Skg 5° C. | 1 week | nd | 0.5 | 98.6 | 0.9 | Nd | nd | nd | 17.2 | ffp | 12363 |
| Skg 25° C. | 1 week | nd | 0.5 | 98.5 | 1.0 | 60 | 12 | 11 | 17.2 | effp | 12793 |
| F/T | (5 cycles) | nd | 0.5 | 98.6 | 0.9 | Nd | nd | nd | 16.5 | effp | 12374 |
| 5° C. | 8 weeks | 125 | 0.5 | 98.7 | 0.8 | 60 | 15 | 11 | 16.9 | ffp | 13086 |
| | 21 weeks | nd | 0.5 | 98.6 | 0.9 | 61 | 13 | 11 | 16.4 | ffp | 14896 |
| | 36 weeks | nd | 0.5 | 98.7 | 0.8 | 59 | 12 | 12 | 16.5 | ffp | 13321 |
| 25° C. | 8 weeks | 125 | 0.7 | 98.1 | 1.2 | 53 | 9 | 18 | 15.4 | ffp | nd |
| | 21 weeks | nd | 0.8 | 97.5 | 1.7 | 41 | 8 | 29 | 19.2 | ffp | 14730 |
| | 36 weeks | nd | 0.9 | 97.0 | 2.1 | 32 | 9 | 32 | 17.4 | ffp | 12028 |
| 30° C. | 8 weeks | 124 | 0.8 | 97.7 | 1.5 | 45 | 8 | 25 | 15.7 | ffp | 11745 |
| | 21 weeks | 123 | 1.1 | 96.3 | 2.6 | 32 | 8 | 24 | 17.4 | ffp | nd |

Formulation F is a liquid formulation with the composition 120 mg/ml Trastuzumab, 20 mM L-histidine/HCl pH 5.5, 105 mM α,α-trehalose dihydrate, 65 mM sodium chloride, 10 mM methionine, 0.06% polysorbate 80, 12'000 U/ml rHuPH20.

| | | | | | | | | | | | |
|---|---|---|---|---|---|---|---|---|---|---|---|
| — | Initial | 127 | 0.4 | 98.9 | 0.7 | 59 | 15 | 10 | 16.7 | effp | 13069 |
| Skg 5° C. | 1 week | nd | 0.5 | 98.6 | 0.9 | Nd | nd | nd | 16.0 | ffp | 13188 |
| Skg 25° C. | 1 week | nd | 0.5 | 98.6 | 0.9 | 60 | 12 | 11 | 15.8 | ffp | 9764 |
| F/T | (5 cycles) | nd | 0.5 | 98.7 | 0.8 | Nd | nd | nd | 18.5 | ffp | 11769 |
| 5° C. | 8 weeks | 125 | 0.5 | 98.7 | 0.8 | 60 | 15 | 11 | 16.5 | ffp | nd |
| | 21 weeks | nd | 0.6 | 98.6 | 0.9 | Nd | nd | nd | 16.6 | ffp | nd |
| | 36 weeks | nd | 0.6 | 98.7 | 0.8 | Nd | nd | nd | 17.2 | ffp | nd |
| 25° C. | 8 weeks | 125 | 0.7 | 98.1 | 1.2 | 53 | 9 | 18 | 17.4 | ffp | 13570 |
| | 21 weeks | nd | 0.9 | 97.4 | 1.7 | Nd | nd | nd | 16.4 | ffp | nd |
| | 36 weeks | nd | 1.0 | 96.9 | 2.1 | Nd | nd | nd | 18.3 | ffp | nd |
| 30° C. | 8 weeks | 124 | 0.8 | 97.5 | 1.7 | 45 | 8 | 25 | 16.2 | ffp | 11860 |
| | 21 weeks | 123 | 1.8 | 95.6 | 2.9 | Nd | nd | nd | 16.1 | ffp | nd |

Formulation G is a liquid formulation with the composition 120 mg/ml Trastuzumab, 20 mM L-histidine/HCl pH 5.5, 210 mM α,α-trehalose dihydrate, 10 mM methionine, 0.04% polysorbate 20.

| Storage condition | Storage Time | Protein concentration (mg/ml) | Size Exclusion-HPLC | | | Ion Exchange-HPLC | | | Turbidity (FTU) | Visible particles |
|---|---|---|---|---|---|---|---|---|---|---|
| | | | HMW (%) | Monomer (%) | LMW (%) | Main Peak (%) | Peak 1 (%) | Peak 4 (%) | | |
| — | Initial | 122 | 0.3 | 99.7 | nd | 71 | 11 | 7 | 4.2 | ffp |
| 5° C. | 4 weeks | nd | 0.3 | 99.6 | nd | 60 | 11 | 11 | nd | nd |
| | 12 weeks | 118 | 0.4 | 99.6 | <0.3 | 70 | 10 | 7 | 4.8 | ffp |
| | 24 weeks | 121 | 0.4 | 99.5 | nd | 68 | 9 | 9 | 4.1 | ffp |
| | 36 weeks | nd | 0.5 | 99.5 | 0.1 | 67 | 8 | 10 | nd | nd |
| 15° C. | 4 weeks | nd | 0.4 | 99.6 | nd | 70 | 10 | 7 | nd | nd |
| | 12 weeks | 121 | 0.5 | 99.4 | <0.3 | 66 | 8 | 11 | 4.3 | ffp |
| | 24 weeks | 121 | 0.5 | 99.3 | <0.3 | 59 | 7 | 17 | 4.4 | ffp |
| | 36 weeks | nd | 0.6 | 99.2 | 0.2 | 53 | 7 | 22 | nd | nd |
| 25° C. | 4 weeks | nd | 0.5 | 99.5 | <0.3 | 66 | 7 | 11 | nd | nd |
| | 12 weeks | 121 | 0.6 | 97.2 | 2.1 | 53 | 6 | 22 | 4.2 | ffp |
| | 24 weeks | 122 | 0.7 | 98.0 | 1.4 | 39 | 6 | 32 | 4.2 | ffp |

TABLE 1-continued

Composition and stability data of liquid anti-HER2 drug product formulations according to this invention and rHuPH20 added prior injection from a bulk with the following composition:
10 mg/ml rHuPH20 in 20 mM His/Histidine/HCl, pH 6.5, 130 mM NaCl, 0.05% (w/v) polysorbate 80

| Storage condition | Storage Time | Protein concentration (mg/ml) | Size Exclusion-HPLC | | | Ion Exchange-HPLC | | | Turbidity (FTU) | Visible particles | HE activity (U/ml) |
|---|---|---|---|---|---|---|---|---|---|---|---|
| | | | HMW (%) | Monomer (%) | LMW (%) | Main Peak (%) | Peak 1 (%) | Peak 4 (%) | | | |

Formulation H is a liquid formulation with the composition 110 mg/ml Trastuzumab, 20 mM L-histidine/HCl
pH 5.0, 210 mM α,α-trehalose dihydrate, 5 mM methionine, 0.02% polysorbate 20, 2'000 U/ml rHuPH20.

| Storage condition | Storage Time | Protein conc. | HMW | Monomer | LMW | Main Peak | Peak 1 | Peak 4 | Turbidity | Visible particles | HE activity |
|---|---|---|---|---|---|---|---|---|---|---|---|
| — | Initial | 111 | 0.6 | 98.7 | 0.8 | 69 | 12 | 6 | 3.9 | ffp | 2081 |
| Skg 5° C. | 1 week | nd | 0.6 | 98.7 | 0.7 | 68 | 12 | 6 | 3.9 | ffp | 2406 |
| Skg 25° C. | 1 week | nd | 0.7 | 98.6 | 0.7 | 68 | 10 | 7 | 3.8 | ffp | nd |
| F/T | (5 cycles) | nd | 0.7 | 98.7 | 0.7 | 68 | 12 | 6 | 3.8 | ffp | 2167 |
| 5° C. | 8 weeks | nd | 0.6 | 98.8 | 0.6 | 69 | 10 | 8 | 4.0 | ffp | 2235 |
| | 12 weeks | 110 | 0.6 | 98.7 | 0.7 | 66 | 10 | 9 | 3.9 | ffp | 1970 |
| | 36 weeks | nd | Nd | nd | nd | Nd | nd | nd | nd | nd | nd |
| 25° C. | 8 weeks | nd | 0.7 | 98.3 | 1.0 | 57 | 5 | 15 | 4.1 | ffp | 1891 |
| | 12 weeks | 111 | 0.7 | 97.8 | 1.5 | 50 | 4 | 20 | 3.8 | ffp | 2079 |
| | 36 weeks | nd | nd | nd | nd | Nd | nd | nd | nd | nd | nd |
| 40° C. | 8 weeks | nd | 1.4 | 94.1 | 4.5 | 31 | 3 | 30 | 4.1 | ffp | nd |
| | 12 weeks | 111 | 1.6 | 92.5 | 5.9 | 28 | 5 | 35 | 4.7 | ffp | nd |

Formulation I is a liquid formulation with the composition 110 mg/ml Trastuzumab, 20 mM L-histidine/HCl
pH 6.0, 210 mM α,α-trehalose dihydrate, 5 mM methionine, 0.02% polysorbate 20, 2'000 U/ml rHuPH20.

| Storage condition | Storage Time | Protein conc. | HMW | Monomer | LMW | Main Peak | Peak 1 | Peak 4 | Turbidity | Visible particles | HE activity |
|---|---|---|---|---|---|---|---|---|---|---|---|
| — | Initial | 111 | 0.8 | 98.5 | 0.7 | 69 | 12 | 7 | 4.7 | effp | 1948 |
| Skg 5° C. | 1 week | Nd | 0.8 | 98.6 | 0.7 | 68 | 12 | 7 | 5.1 | ffp | 2672 |
| Skg 25° C. | 1 week | Nd | 0.8 | 98.6 | 0.7 | 67 | 11 | 8 | 4.7 | ffp | 1724 |
| F/T | (5 cycles) | Nd | 0.8 | 98.6 | 0.7 | 68 | 12 | 7 | 4.5 | ffp | 2507 |
| 5° C. | 8 weeks | Nd | 0.8 | 98.6 | 0.6 | 68 | 11 | 8 | 4.5 | ffp | 1911 |
| | 12 weeks | 112 | 0.8 | 98.5 | 0.7 | 65 | 11 | 10 | 4.7 | ffp | 2034 |
| | 36 weeks | Nd | nd | nd | nd | nd | nd | nd | nd | nd | nd |
| 25° C. | 8 weeks | Nd | 0.9 | 98.1 | 1.0 | 53 | 12 | 18 | 4.8 | effp | 1910 |
| | 12 weeks | 111 | 1.0 | 97.8 | 1.2 | 45 | 12 | 21 | 4.9 | ffp | 2157 |
| | 36 weeks | Nd | nd | nd | nd | nd | nd | nd | nd | nd | nd |
| 40° C. | 8 weeks | Nd | 1.6 | 95.3 | 3.1 | 26 | 9 | 26 | 5.0 | ffp | nd |
| | 12 weeks | 112 | 1.9 | 93.9 | 4.3 | 20 | 9 | 22 | 5.7 | ffp | nd |

Formulation J is a liquid formulation with the composition 110 mg/ml Trastuzumab, 20 mM L-histidine/HCl
pH 5.0, 210 mM α,α-trehalose dihydrate, 5 mM methionine, 0.06% polysorbate 20, 2'000 U/ml rHuPH20.

| Storage condition | Storage Time | Protein conc. | HMW | Monomer | LMW | Main Peak | Peak 1 | Peak 4 | Turbidity | Visible particles | HE activity |
|---|---|---|---|---|---|---|---|---|---|---|---|
| — | Initial | 111 | 0.6 | 98.7 | 0.7 | 69 | 12 | 6 | 3.7 | ffp | 2198 |
| Skg 5° C. | 1 week | nd | 0.6 | 98.6 | 0.7 | 68 | 12 | 6 | 4.3 | effp | 2528 |
| Skg 25° C. | 1 week | nd | 0.6 | 98.6 | 0.8 | 68 | 10 | 7 | 4.0 | effp | 1993 |
| F/T | (5 cycles) | nd | 0.7 | 98.7 | 0.7 | 68 | 12 | 6 | 3.7 | ffp | 2256 |
| 5° C. | 8 weeks | nd | 0.6 | 98.8 | 0.6 | 68 | 10 | 8 | 4.1 | ffp | 2263 |
| | 12 weeks | 111 | 0.6 | 98.6 | 0.8 | 66 | 10 | 9 | 3.9 | ffp | 2337 |
| | 36 weeks | nd | nd | nd | nd | Nd | nd | nd | nd | nd | nd |
| 25° C. | 8 weeks | nd | 0.7 | 98.3 | 1.0 | 56 | 5 | 15 | 4.0 | ffp | 1931 |
| | 12 weeks | 111 | 0.7 | 97.9 | 1.4 | 50 | 4 | 20 | 4.0 | ffp | 2291 |
| | 36 weeks | nd | nd | nd | nd | Nd | nd | nd | nd | nd | nd |
| 40° C. | 8 weeks | nd | 1.3 | 94.5 | 4.2 | 30 | 3 | 35 | 4.2 | ffp | nd |
| | 12 weeks | 111 | 1.6 | 92.4 | 6.0 | 27 | 5 | 35 | 4.2 | ffp | nd |

Formulation K is a liquid formulation with the composition 110 mg/ml Trastuzumab, 20 mM L-histidine/HCl
pH 6.0, 210 mM α,α-trehalose dihydrate, 5 mM methionine, 0.06% polysorbate 20, 2'000 U/ml rHuPH20.

| Storage condition | Storage Time | Protein conc. | HMW | Monomer | LMW | Main Peak | Peak 1 | Peak 4 | Turbidity | Visible particles | HE activity |
|---|---|---|---|---|---|---|---|---|---|---|---|
| — | Initial | 111 | 0.8 | 98.6 | 0.7 | 69 | 12 | 7 | 4.7 | ffp | 2258 |
| Skg 5° C. | 1 week | nd | 0.8 | 98.6 | 0.7 | 68 | 12 | 7 | 5.0 | ffp | 2680 |
| Skg 25° C. | 1 week | nd | 0.8 | 98.5 | 0.7 | 67 | 11 | 8 | 4.6 | effp | 2049 |
| F/T | (5 cycles) | nd | 0.8 | 98.6 | 0.7 | 69 | 12 | 7 | 4.8 | ffp | 2316 |
| 5° C. | 8 weeks | nd | 0.8 | 98.5 | 0.7 | 68 | 12 | 8 | 4.5 | ffp | 2132 |
| | 12 weeks | 112 | 0.8 | 98.5 | 0.7 | 65 | 12 | 9 | 5.2 | ffp | 2260 |
| | 36 weeks | nd | nd | nd | nd | Nd | nd | nd | nd | nd | nd |
| 25° C. | 8 weeks | nd | 0.9 | 98.3 | 0.8 | 53 | 12 | 18 | 4.5 | ffp | 1863 |
| | 12 weeks | 112 | 1.0 | 97.9 | 1.2 | 46 | 12 | 21 | 4.7 | ffp | 1917 |
| | 36 weeks | nd | nd | nd | nd | Nd | nd | nd | nd | nd | nd |
| 40° C. | 8 weeks | nd | 1.5 | 95.4 | 3.1 | 26 | 10 | 26 | 5.2 | ffp | nd |
| | 12 weeks | 112 | 1.9 | 93.9 | 4.3 | 28 | 8 | 22 | 6.2 | ffp | nd |

Formulation L is a liquid formulation with the composition 110 mg/ml Trastuzumab, 20 mM L-histidine/HCl
pH 5.0, 210 mM α,α-trehalose dihydrate, 15 mM methionine, 0.02% polysorbate 20, 2'000 U/ml rHuPH20.

| Storage condition | Storage Time | Protein conc. | HMW | Monomer | LMW | Main Peak | Peak 1 | Peak 4 | Turbidity | Visible particles | HE activity |
|---|---|---|---|---|---|---|---|---|---|---|---|
| — | Initial | 111 | 0.6 | 98.7 | 0.7 | 69 | 12 | 6 | 3.5 | effp | 2301 |
| Skg 5° C. | 1 week | nd | 0.6 | 98.7 | 0.7 | 69 | 12 | 6 | 4.1 | ffp | 2574 |
| Skg 25° C. | 1 week | nd | 0.6 | 98.7 | 0.7 | 68 | 10 | 7 | 4.1 | ffp | nd |
| F/T | (5 cycles) | nd | 0.7 | 98.5 | 0.8 | 68 | 12 | 7 | 3.6 | ffp | 2435 |
| 5° C. | 8 weeks | nd | 0.6 | 98.8 | 0.6 | 68 | 10 | 7 | 3.8 | ffp | 2263 |
| | 12 weeks | 111 | 0.6 | 98.7 | 0.7 | 67 | 10 | 8 | 3.8 | ffp | 1857 |
| | 36 weeks | nd | nd | nd | nd | Nd | nd | nd | nd | nd | nd |

TABLE 1-continued

Composition and stability data of liquid anti-HER2 drug product formulations according to this invention

| Condition | Time | | | | | | | | | | | |
|---|---|---|---|---|---|---|---|---|---|---|---|---|
| 25° C. | 8 weeks | nd | 0.7 | 98.4 | 1.0 | 56 | 5 | 15 | 3.8 | ffp | 1919 |
| | 12 weeks | 111 | 0.7 | 97.9 | 1.4 | 50 | 4 | 19 | 3.8 | ffp | 2106 |
| | 36 weeks | nd | nd | nd | nd | Nd | nd | nd | nd | nd | nd |
| 40° C. | 8 weeks | nd | 1.3 | 94.2 | 4.5 | 31 | 4 | 34 | 3.9 | ffp | nd |
| | 12 weeks | 111 | 1.5 | 92.6 | 6.0 | 28 | 4 | 35 | 4.2 | ffp | nd |

Formulation M is a liquid formulation with the composition 110 mg/ml Trastuzumab, 20 mM L-histidine/HCl pH 6.0, 210 mM α,α-trehalose dihydrate, 15 mM methionine, 0.02% polysorbate 20, 2'000 U/ml rHuPH20.

| Condition | Time | | | | | | | | | | | |
|---|---|---|---|---|---|---|---|---|---|---|---|---|
| — | Initial | 110 | 0.7 | 98.6 | 0.7 | 69 | 12 | 7 | 4.4 | effp | 2203 |
| Skg 5° C. | 1 week | nd | 0.7 | 98.6 | 0.6 | 69 | 12 | 7 | 5.2 | ffp | 2169 |
| Skg 25° C. | 1 week | nd | 0.7 | 98.6 | 0.7 | 67 | 11 | 8 | 4.9 | ffp | 1661 |
| F/T | (5 cycles) | nd | 0.7 | 98.6 | 0.6 | 68 | 12 | 7 | 4.6 | ffp | 2183 |
| 5° C. | 8 weeks | nd | 0.7 | 98.6 | 0.7 | 68 | 12 | 8 | 4.5 | ffp | 2188 |
| | 12 weeks | 111 | 0.8 | 98.6 | 0.7 | 66 | 12 | 9 | 4.9 | effp | 2028 |
| | 36 weeks | nd | nd | nd | nd | Nd | nd | nd | nd | nd | nd |
| 25° C. | 8 weeks | nd | 0.9 | 98.1 | 1.1 | 53 | 12 | 18 | 4.5 | ffp | 1900 |
| | 12 weeks | 111 | 0.9 | 98.0 | 1.2 | 46 | 12 | 21 | 4.7 | ffp | 1936 |
| | 36 weeks | nd | nd | nd | nd | Nd | nd | nd | nd | nd | nd |
| 40° C. | 8 weeks | nd | 1.5 | 95.0 | 3.5 | 26 | 10 | 26 | 5.4 | ffp | nd |
| | 12 weeks | 111 | 1.7 | 94.1 | 4.2 | 27 | 8 | 22 | 5.5 | ffp | nd |

Formulation N is a liquid formulation with the composition 110 mg/ml Trastuzumab, 20 mM L-histidine/HCl pH 5.0, 210 mM α,α-trehalose dihydrate, 15 mM methionine, 0.06% polysorbate 20, 2'000 U/ml rHuPH20.

| Condition | Time | | | | | | | | | | | |
|---|---|---|---|---|---|---|---|---|---|---|---|---|
| — | Initial | 111 | 0.6 | 98.7 | 0.7 | 69 | 12 | 7 | 3.8 | effp | 2410 |
| Skg 5° C. | 1 week | Nd | 0.6 | 98.6 | 0.7 | 69 | 12 | 6 | 4.0 | effp | 2559 |
| Skg 25° C. | 1 week | Nd | 0.6 | 98.6 | 0.8 | 68 | 10 | 7 | 3.7 | ffp | 2086 |
| F/T | (5 cycles) | Nd | 0.7 | 98.7 | 0.7 | 68 | 12 | 6 | 4.0 | ffp | 2457 |
| 5° C. | 8 weeks | Nd | 0.6 | 98.8 | 0.7 | 69 | 10 | 7 | 3.9 | ffp | 2102 |
| | 12 weeks | 111 | 0.6 | 98.8 | 0.7 | 67 | 10 | 8 | 3.6 | effp | 2037 |
| | 36 weeks | Nd | nd | nd | nd | Nd | nd | nd | nd | nd | nd |
| 25° C. | 8 weeks | Nd | 0.7 | 98.2 | 1.1 | 57 | 5 | 15 | 3.8 | ffp | 2215 |
| | 12 weeks | 111 | 0.7 | 97.9 | 1.4 | 50 | 4 | 19 | 3.7 | ffp | 2050 |
| | 36 weeks | Nd | nd | nd | nd | Nd | nd | nd | nd | nd | nd |
| 40° C. | 8 weeks | Nd | 1.3 | 94.7 | 4.1 | 30 | 4 | 34 | 4.0 | ffp | nd |
| | 12 weeks | 111 | 1.5 | 92.5 | 6.0 | 28 | 4 | 35 | 4.5 | ffp | nd |

Formulation O is a liquid formulation with the composition 110 mg/ml Trastuzumab, 20 mM L-histidine/HCl pH 6.0, 210 mM α,α-trehalose dihydrate, 15 mM methionine, 0.06% polysorbate 20, 2'000 U/ml rHuPH20.

| Condition | Time | | | | | | | | | | | |
|---|---|---|---|---|---|---|---|---|---|---|---|---|
| — | Initial | 111 | 0.8 | 98.6 | 0.7 | 69 | 12 | 7 | 4.5 | ffp | 2153 |
| Skg 5° C. | 1 week | nd | 0.7 | 98.6 | 0.7 | 69 | 12 | 7 | 4.7 | ffp | 1846 |
| Skg 25° C. | 1 week | nd | 0.7 | 98.5 | 0.7 | 67 | 11 | 8 | 4.9 | effp | 2192 |
| F/T | (5 cycles) | nd | 0.7 | 98.6 | 0.7 | 69 | 12 | 7 | 4.3 | effp | 2323 |
| 5° C. | 8 weeks | nd | 0.7 | 98.7 | 0.6 | 68 | 12 | 8 | 4.8 | ffp | 2049 |
| | 12 weeks | 112 | 0.8 | 98.5 | 0.7 | 66 | 12 | 9 | 4.6 | ffp | 1903 |
| | 36 weeks | nd | nd | nd | nd | Nd | nd | nd | nd | nd | nd |
| 25° C. | 8 weeks | nd | 0.9 | 98.2 | 0.9 | 53 | 12 | 18 | 4.8 | ffp | 2002 |
| | 12 weeks | 112 | 0.9 | 97.9 | 1.2 | 46 | 13 | 21 | 4.8 | ffp | 2216 |
| | 36 weeks | nd | nd | nd | nd | Nd | nd | nd | nd | nd | nd |
| 40° C. | 8 weeks | nd | 1.5 | 95.6 | 2.9 | 26 | 10 | 25 | 5.2 | ffp | nd |
| | 12 weeks | 112 | 1.9 | 94.0 | 4.3 | 27 | 8 | 22 | 6.1 | ffp | nd |

Formulation P is a liquid formulation with the composition 130 mg/ml Trastuzumab, 20 mM L-histidine/HCl pH 5.0, 210 mM α,α-trehalose dihydrate, 5 mM methionine, 0.02% polysorbate 20, 2'000 U/ml rHuPH20.

| Condition | Time | | | | | | | | | | | |
|---|---|---|---|---|---|---|---|---|---|---|---|---|
| — | Initial | 128 | 0.7 | 98.7 | 0.7 | 69 | 12 | 6 | 3.8 | ffp | 2035 |
| Skg 5° C. | 1 week | Nd | 0.7 | 98.7 | 0.7 | 69 | 12 | 6 | 3.4 | ffp | 2728 |
| Skg 25° C. | 1 week | Nd | 0.7 | 98.6 | 0.7 | 68 | 10 | 7 | 3.9 | ffp | nd |
| F/T | (5 cycles) | Nd | 0.7 | 98.7 | 0.7 | 69 | 12 | 6 | 3.7 | ffp | 2559 |
| 5° C. | 8 weeks | Nd | 0.6 | 98.8 | 0.6 | 69 | 10 | 7 | 3.6 | ffp | 2217 |
| | 12 weeks | 129 | 0.6 | 98.7 | 0.7 | 67 | 11 | 9 | 3.8 | ffp | 1878 |
| | 36 weeks | Nd | nd | nd | nd | Nd | nd | nd | nd | nd | nd |
| 25° C. | 8 weeks | Nd | 0.8 | 98.2 | 1.0 | 57 | 5 | 15 | 3.5 | ffp | 2091 |
| | 12 weeks | 128 | 0.8 | 97.8 | 1.4 | 51 | 4 | 19 | 4.3 | ffp | 1887 |
| | 36 weeks | Nd | nd | nd | nd | Nd | nd | nd | nd | nd | nd |
| 40° C. | 8 weeks | Nd | 1.6 | 94.2 | 4.2 | 31 | 4 | 35 | 3.9 | ffp | nd |
| | 12 weeks | 129 | 1.9 | 92.1 | 5.9 | 28 | 5 | 35 | 4.2 | ffp | nd |

Formulation Q is a liquid formulation with the composition 130 mg/ml Trastuzumab, 20 mM L-histidine/HCl pH 6.0, 210 mM α,α-trehalose dihydrate, 5 mM methionine, 0.02% polysorbate 20, 2'000 U/ml rHuPH20.

| Condition | Time | | | | | | | | | | | |
|---|---|---|---|---|---|---|---|---|---|---|---|---|
| — | Initial | 131 | 0.8 | 98.5 | 0.7 | 69 | 12 | 7 | 4.4 | effp | 2309 |
| Skg 5° C. | 1 week | Nd | 0.8 | 98.5 | 0.7 | 69 | 12 | 7 | 4.4 | ffp | 2522 |
| Skg 25° C. | 1 week | Nd | 0.9 | 98.4 | 0.7 | 67 | 11 | 8 | 4.8 | ffp | 1787 |
| F/T | (5 cycles) | Nd | 0.8 | 98.5 | 0.6 | 69 | 12 | 6 | 4.8 | ffp | 2312 |
| 5° C. | 8 weeks | Nd | 0.9 | 98.6 | 0.6 | 68 | 12 | 8 | 5.1 | ffp | 2131 |
| | 12 weeks | 132 | 0.9 | 98.4 | 0.7 | 66 | 11 | 9 | 4.9 | effp | 1931 |
| | 36 weeks | Nd | nd | nd | nd | Nd | nd | nd | nd | nd | nd |
| 25° C. | 8 weeks | Nd | 1.1 | 97.8 | 1.1 | 54 | 12 | 18 | 5.1 | ffp | 1888 |
| | 12 weeks | 132 | 1.1 | 97.8 | 1.1 | 46 | 12 | 21 | 4.7 | ffp | 1912 |
| | 36 weeks | Nd | nd | nd | nd | Nd | nd | nd | nd | nd | nd |

TABLE 1-continued

Composition and stability data of liquid anti-HER2 drug product formulations according to this invention

| | | | | | | | | | | | |
|---|---|---|---|---|---|---|---|---|---|---|---|
| 40° C. | 8 weeks | Nd | 1.8 | 95.2 | 3.0 | 27 | 10 | 27 | 5.6 | effp | nd |
| | 12 weeks | 132 | 2.2 | 93.4 | 4.4 | 28 | 8 | 22 | 6.1 | ffp | nd |

Formulation R is a liquid formulation with the composition 130 mg/ml Trastuzumab, 20 mM L-histidine/HCl pH 5.0, 210 mM α,α-trehalose dihydrate, 5 mM methionine, 0.06% polysorbate 20, 2'000 U/ml rHuPH20.

| | | | | | | | | | | | |
|---|---|---|---|---|---|---|---|---|---|---|---|
| — | Initial | 131 | 0.7 | 98.6 | 0.7 | 69 | 12 | 6 | 3.7 | effp | 2096 |
| Skg 5° C. | 1 week | Nd | 0.7 | 98.7 | 0.6 | 69 | 12 | 6 | 3.7 | effp | 1856 |
| Skg 25° C. | 1 week | Nd | 0.7 | 98.5 | 0.8 | 68 | 10 | 7 | 4.3 | effp | 1958 |
| F/T | (5 cycles) | Nd | 0.7 | 98.7 | 0.6 | 69 | 12 | 6 | 3.8 | effp | 2371 |
| 5° C. | 8 weeks | Nd | 0.7 | 98.7 | 0.6 | 69 | 10 | 7 | 3.5 | effp | 2075 |
| | 12 weeks | 131 | 0.6 | 98.6 | 0.7 | 67 | 10 | 8 | 3.6 | effp | 2350 |
| | 36 weeks | Nd | nd | nd | nd | Nd | nd | nd | nd | nd | nd |
| 25° C. | 8 weeks | Nd | 0.9 | 98.2 | 1.0 | 58 | 5 | 15 | 3.5 | effp | 1989 |
| | 12 weeks | 131 | 0.9 | 97.7 | 1.4 | 51 | 4 | 20 | 3.9 | effp | 1999 |
| | 36 weeks | Nd | nd | nd | nd | Nd | nd | nd | nd | nd | nd |
| 40° C. | 8 weeks | Nd | 1.6 | 94.3 | 4.1 | 32 | 4 | 35 | 4.2 | ffp | nd |
| | 12 weeks | 132 | 2.0 | 92.0 | 6.0 | 29 | 5 | 35 | 4.6 | effp | nd |

Formulation S is a liquid formulation with the composition 130 mg/ml Trastuzumab, 20 mM L-histidine/HCl pH 6.0, 210 mM α,α-trehalose dihydrate, 5 mM methionine, 0.06% polysorbate 20, 2'000 U/ml rHuPH20.

| | | | | | | | | | | | |
|---|---|---|---|---|---|---|---|---|---|---|---|
| — | Initial | 131 | 0.8 | 98.5 | 0.7 | 69 | 12 | 7 | 4.6 | effp | 2406 |
| Skg 5° C. | 1 week | Nd | 0.8 | 98.5 | 0.7 | 69 | 12 | 7 | 4.8 | wafp | 2808 |
| Skg 25° C. | 1 week | Nd | 0.9 | 98.4 | 0.7 | 67 | 11 | 8 | 4.9 | ffp | 2141 |
| F/T | (5 cycles) | Nd | 0.8 | 98.5 | 0.6 | 69 | 12 | 6 | 4.7 | ffp | 2487 |
| 5° C. | 8 weeks | Nd | 0.8 | 98.5 | 0.7 | 69 | 12 | 8 | 4.8 | effp | 2076 |
| | 12 weeks | 132 | 0.9 | 98.4 | 0.7 | 66 | 12 | 9 | 4.8 | effp | 1897 |
| | 36 weeks | Nd | nd | nd | nd | Nd | nd | nd | nd | nd | nd |
| 25° C. | 8 weeks | Nd | 1.1 | 97.8 | 1.1 | 55 | 12 | 18 | 5.0 | ffp | 1956 |
| | 12 weeks | 131 | 1.1 | 97.7 | 1.2 | 47 | 12 | 21 | 4.9 | ffp | 2094 |
| | 36 weeks | Nd | nd | nd | nd | Nd | nd | nd | nd | nd | nd |
| 40° C. | 8 weeks | Nd | 1.9 | 95.2 | 3.0 | 27 | 9 | 27 | 5.7 | ffp | nd |
| | 12 weeks | 133 | 2.2 | 93.5 | 4.3 | 21 | 9 | 22 | 6.1 | ffp | nd |

Formulation T is a liquid formulation with the composition 130 mg/ml Trastuzumab, 20 mM L-histidine/HCl pH 5.0, 210 mM α,α-trehalose dihydrate, 15 mM methionine, 0.02% polysorbate 20, 2'000 U/ml rHuPH20.

| | | | | | | | | | | | |
|---|---|---|---|---|---|---|---|---|---|---|---|
| — | Initial | 131 | 0.7 | 98.7 | 0.7 | 69 | 12 | 6 | 3.7 | effp | 2311 |
| Skg 5° C. | 1 week | nd | 0.7 | 98.7 | 0.7 | 69 | 12 | 6 | 3.7 | ffp | 2397 |
| Skg 25° C. | 1 week | nd | 0.7 | 98.5 | 0.8 | 68 | 10 | 7 | 4.0 | effp | nd |
| F/T | (5 cycles) | nd | 0.7 | 98.7 | 0.6 | 68 | 12 | 6 | 3.7 | ffp | 2277 |
| 5° C. | 8 weeks | nd | 0.6 | 98.8 | 0.5 | 67 | 10 | 7 | 3.5 | ffp | 2167 |
| | 12 weeks | 131 | 0.6 | 98.6 | 0.7 | 69 | 10 | 7 | 3.7 | ffp | 2070 |
| | 36 weeks | nd | nd | nd | nd | Nd | nd | nd | nd | nd | nd |
| 25° C. | 8 weeks | nd | 0.8 | 98.2 | 1.0 | 56 | 5 | 15 | 3.6 | ffp | 2122 |
| | 12 weeks | 131 | 0.8 | 97.8 | 1.4 | 52 | 4 | 19 | 3.7 | ffp | 2138 |
| | 36 weeks | nd | nd | nd | nd | Nd | nd | nd | nd | nd | nd |
| 40° C. | 8 weeks | nd | 1.5 | 94.3 | 4.2 | 31 | 4 | 34 | 4.0 | ffp | nd |
| | 12 weeks | 132 | 1.8 | 92.2 | 6.0 | 29 | 4 | 35 | 4.1 | ffp | nd |

Formulation U is a liquid formulation with the composition 130 mg/ml Trastuzumab, 20 mM L-histidine/HCl pH 6.0, 210 mM α,α-trehalose dihydrate, 15 mM methionine, 0.02% polysorbate 20, 2'000 U/ml rHuPH20.

| | | | | | | | | | | | |
|---|---|---|---|---|---|---|---|---|---|---|---|
| — | Initial | 131 | 0.8 | 98.5 | 0.7 | 69 | 12 | 7 | 4.5 | effp | 2768 |
| Skg 5° C. | 1 week | nd | 0.8 | 98.6 | 0.7 | 68 | 12 | 7 | 4.7 | effp | 2884 |
| Skg 25° C. | 1 week | nd | 0.8 | 98.5 | 0.7 | 68 | 11 | 8 | 6.0 | effp | 2044 |
| F/T | (5 cycles) | nd | 0.8 | 98.6 | 0.6 | 68 | 12 | 7 | 4.6 | ffp | 2617 |
| 5° C. | 8 weeks | nd | 0.8 | 98.5 | 0.7 | 67 | 12 | 8 | 4.3 | ffp | 2571 |
| | 12 weeks | 132 | 0.8 | 98.5 | 0.7 | 67 | 12 | 8 | 4.5 | ffp | 2164 |
| | 36 weeks | nd | nd | nd | nd | Nd | nd | nd | nd | nd | nd |
| 25° C. | 8 weeks | nd | 1.0 | 98.0 | 1.0 | 52 | 12 | 18 | 4.9 | ffp | 2116 |
| | 12 weeks | 131 | 1.0 | 97.7 | 1.3 | 47 | 13 | 21 | 5.0 | effp | 1990 |
| | 36 weeks | nd | nd | nd | nd | Nd | nd | nd | nd | nd | nd |
| 40° C. | 8 weeks | nd | 1.7 | 95.4 | 2.9 | 24 | 10 | 24 | 5.4 | ffp | nd |
| | 12 weeks | 132 | 2.0 | 93.7 | 4.3 | 19 | 9 | 20 | 5.7 | ffp | nd |

Formulation V is a liquid formulation with the composition 130 mg/ml Trastuzumab, 20 mM L-histidine/HCl pH 5.0, 210 mM α,α-trehalose dihydrate, 15 mM methionine, 0.06% polysorbate 20, 2'000 U/ml rHuPH20.

| | | | | | | | | | | | |
|---|---|---|---|---|---|---|---|---|---|---|---|
| — | Initial | 131 | 0.7 | 98.7 | 0.7 | 68 | 12 | 6 | 3.7 | effp | 2323 |
| Skg 5° C. | 1 week | nd | 0.7 | 98.6 | 0.7 | 69 | 12 | 6 | 3.7 | ffp | 2646 |
| Skg 25° C. | 1 week | nd | 0.7 | 98.5 | 0.8 | 68 | 10 | 7 | 3.8 | ffp | 2056 |
| F/T | (5 cycles) | nd | 0.7 | 98.7 | 0.7 | 68 | 12 | 6 | 3.5 | effp | 2498 |
| 5° C. | 8 weeks | nd | 0.6 | 98.9 | 0.5 | 67 | 10 | 7 | 3.5 | effp | 2179 |
| | 12 weeks | 132 | 0.6 | 98.6 | 0.8 | 69 | 10 | 7 | 3.7 | ffp | 2119 |
| | 36 weeks | nd | nd | nd | nd | Nd | nd | nd | nd | nd | nd |
| 25° C. | 8 weeks | nd | 0.8 | 98.1 | 1.1 | 56 | 5 | 15 | 3.6 | ffp | 2072 |
| | 12 weeks | 132 | 0.8 | 97.8 | 1.4 | 52 | 4 | 19 | 3.9 | effp | 2348 |
| | 36 weeks | nd | nd | nd | nd | Nd | nd | nd | nd | nd | nd |
| 40° C. | 8 weeks | nd | 1.5 | 94.2 | 4.3 | 31 | 4 | 34 | 3.9 | ffp | nd |
| | 12 weeks | 132 | 1.8 | 92.3 | 5.9 | 30 | 5 | 34 | 4.3 | ffp | nd |

TABLE 1-continued

Composition and stability data of liquid anti-HER2 drug product formulations according to this invention Formulation W is a liquid formulation with the composition 130 mg/ml Trastuzumab, 20 mM L-histidine/HCl
pH 6.0, 210 mM α,α-trehalose dihydrate, 15 mM methionine, 0.06% polysorbate 20, 2'000 U/ml rHuPH20.

| | | | | | | | | | | | |
|---|---|---|---|---|---|---|---|---|---|---|---|
| — | Initial | 131 | 0.8 | 98.5 | 0.7 | 69 | 12 | 7 | 4.7 | ffp | 2018 |
| Skg 5° C. | 1 week | nd | 0.8 | 98.5 | 0.7 | 69 | 12 | 7 | 4.6 | ffp | 1790 |
| Skg 25° C. | 1 week | nd | 0.8 | 98.5 | 0.7 | 67 | 11 | 8 | 4.9 | ffp | 1918 |
| F/T | (5 cycles) | nd | 0.8 | 98.6 | 0.7 | 69 | 12 | 7 | 4.7 | ffp | 2379 |
| 5° C. | 8 weeks | nd | 0.8 | 98.7 | 0.5 | 67 | 11 | 8 | 4.4 | ffp | 2028 |
| | 12 weeks | 131 | 0.8 | 98.4 | 0.8 | 67 | 12 | 8 | 4.7 | effp | 1964 |
| | 36 weeks | nd | nd | nd | nd | Nd | nd | Nd | nd | nd | nd |
| 25° C. | 8 weeks | nd | 1.0 | 98.0 | 1.0 | 53 | 12 | 18 | 4.3 | ffp | 2198 |
| | 12 weeks | 131 | 1.0 | 97.8 | 1.2 | 47 | 13 | 20 | 5.0 | ffp | 1894 |
| | 36 weeks | nd | nd | nd | nd | Nd | nd | Nd | nd | nd | nd |
| 40° C. | 8 weeks | nd | 1.7 | 95.4 | 3.0 | 24 | 9 | 25 | 5.0 | ffp | nd |
| | 12 weeks | 132 | 2.0 | 93.7 | 4.4 | 27 | 9 | 20 | 5.8 | effp | nd |

Formulation X is a liquid formulation with the composition 120 mg/ml Trastuzumab, 20 mM L-histidine/HCl
pH 5.5, 210 mM α,α-trehalose dihydrate, 10 mM methionine, 0.04% polysorbate 20, 2'000 U/ml rHuPH20.

| | | | | | | | | | | | |
|---|---|---|---|---|---|---|---|---|---|---|---|
| — | Initial | 121 | 0.8 | 98.5 | 0.7 | 69 | 12 | 7 | 4.2 | effp | 2277 |
| Skg 5° C. | 1 week | nd | 0.8 | 98.6 | 0.7 | 69 | 12 | 6 | 4.2 | ffp | 1855 |
| Skg 25° C. | 1 week | nd | 0.8 | 98.5 | 0.7 | 68 | 11 | 7 | 4.8 | ffp | 2070 |
| F/T | (5 cycles) | nd | 0.8 | 98.6 | 0.7 | 69 | 12 | 6 | 4.5 | ffp | 2477 |
| 5° C. | 8 weeks | nd | 0.8 | 98.6 | 0.6 | 68 | 10 | 8 | 4.3 | ffp | 2447 |
| | 12 weeks | 122 | 0.7 | 98.6 | 0.7 | 67 | 10 | 9 | 4.3 | ffp | 2189 |
| | 36 weeks | nd | nd | nd | nd | Nd | nd | Nd | nd | nd | nd |
| 25° C. | 8 weeks | nd | 0.9 | 98.2 | 1.0 | 57 | 7 | 18 | 4.5 | ffp | 2030 |
| | 12 weeks | 122 | 0.9 | 97.8 | 1.3 | 50 | 7 | 23 | 4.5 | ffp | 2030 |
| | 36 weeks | nd | nd | nd | nd | Nd | nd | Nd | nd | nd | nd |
| 40° C. | 8 weeks | nd | 1.4 | 95.3 | 3.3 | 34 | 6 | 33 | 4.8 | ffp | nd |
| | 12 weeks | 122 | 1.7 | 93.6 | 4.6 | 32 | 7 | 31 | 5.1 | ffp | nd |

Example 2: Preparation of a Lyophilized Formulation

A solution of approx. 60 mg/ml Trastuzumab was prepared as described above for liquid formulations. All excipients have been added at half of the concentration of the above mentioned liquid formulation. The formulation was sterile filtered through 0.22 μm filters and aseptically distributed in equal amounts into sterile 20 ml glass vials. The vials were partly closed with ETFE (Copolymer of ethylene and tetrafluoroethylene)-coated rubber stoppers suitable for the use in lyophilization processes and lyophilized using the freeze-drying cycle reported in Table 2.

TABLE 2

Freeze-drying Cycle

| Step | Shelf temperature (° C.) | Ramp Rate (° C./min) | Hold time (min) | Vacuum Set point (μbar) |
|---|---|---|---|---|
| Pre-cooling | 5° C. | 0.0 | 60 | — |
| Freezing | −40° C. | 1.0 | 120 | — |
| Primary Drying | −25° C. | 0.5 | 4560 | 80 |
| Secondary Drying | +25° C. | 0.2 | 300 | 80 |

The product was first cooled from room temperature to approx 5° C. (pre-cooling), followed by a freezing step at −40° C. with a plate cooling rate of approx. 1° C./min, followed by a holding step at −40° C. for about 2 hours. The first drying step was performed at a plate temperature of approx. −25° C. and a chamber pressure of approx. 80 μbar for about 76 hours. Subsequently, the second drying step started with a temperature ramp of 0.2° C./min from −25° C. to 25° C., followed by a holding step at 25° C. for at least 5 hours at a chamber pressure of approx. 80 μbar.

Lyophilization was carried out in a Usifroid SMH-90 LN2 freeze-dryer (Usifroid, Maurepas, France) or a LyoStar II Freeze-dryer (FTS Systems, Stone Ridge, NY, USA). The freeze-dried samples were stored at different climate conditions (5° C., 25° C. and 30° C.) for different intervals of time. The lyophilized vials were reconstituted to a final volume of 2.65 ml with water for injection (WFI) yielding an isotonic formulation with an antibody concentration of approx. 120 mg/ml. The reconstitution time of the freeze-dried cakes was around 10 min. Analysis of the reconstituted samples was performed after a 24 hour incubation period of the reconstituted liquid sample at ambient temperature.

The samples were again analyzed by the following analytical methods described above: 1) UV spectrophotometry;
2) Size Exclusion Chromatography (SEC);
3) Ion exchange chromatography (IEC);
4) turbidity of the solution; and
5) for visible particles.

The results of the stability testing for the Formulations is provided in the Table 3 below wherein the following abbreviations are used:

ffp: =free from particles;
effp: =essentially free from particles;
nd: =not determined

TABLE 3

Composition and stability data of a lyophilized anti-HER2 drug product formulation according to this invention
Formulation Y is a lyophilized formulation with the composition 120 mg/ml Trastuzumab, 20 mM L-histidine/HCl
pH 5.5, 210 mM α,α-trehalose dihydrate, 10 mM methionine, 0.04% polysorbate 20, 12'000 U/ml rHuPH20 after reconstitution.

| Storage condition | Storage Time | Protein concentration (mg/ml) | Size Exclusion-HPLC | | | Ion Exchange-HPLC | | | Turbidity (FTU) | Visible particles | HE activity (U/ml) |
|---|---|---|---|---|---|---|---|---|---|---|---|
| | | | HMW (%) | Monomer (%) | LMW (%) | Main Peak (%) | Peak 1 (%) | Peak 4 (%) | | | |
| — | Initial | 129 | 0.5 | 98.8 | 0.8 | 59 | 15 | 10 | 7.1 | ffp | 12451 |
| 5° C. | 8 weeks | 124 | 0.6 | 98.6 | 0.9 | 59 | 16 | 10 | 5.7 | effp | 13380 |
| | 21 weeks | nd | 0.8 | 98.6 | 0.7 | 62 | 15 | 8 | 5.9 | effp | 14927 |
| | 36 weeks | nd | 0.8 | 98.5 | 0.7 | 59 | 16 | 10 | 6.0 | ffp | 13744 |
| 25° C. | 8 weeks | 120 | 1.3 | 97.8 | 0.8 | 59 | 16 | 11 | 6.1 | effp | 13162 |
| | 21 weeks | nd | 2.1 | 96.7 | 1.2 | 61 | 15 | 8 | 5.7 | effp | 15396 |
| | 36 weeks | nd | 2.7 | 96.6 | 0.7 | 58 | 15 | 11 | 6.0 | ffp | 13673 |
| 30° C. | 8 weeks | 121 | 1.9 | 97.5 | 0.9 | 58 | 16 | 11 | 5.7 | effp | 13425 |
| | 21 weeks | 126 | 3.2 | 96.0 | 0.8 | 60 | 14 | 8 | 6.0 | effp | nd |
| | 36 weeks | nd | 3.9 | 95.4 | 0.7 | 57 | 14 | 11 | 5.9 | ffp | 15034 |

The properties of the above formulations provided are summarized in the following Table 4:

| | Tr | His | | tre | NaCl | Meth | PS | | rHu |
|---|---|---|---|---|---|---|---|---|---|
| F | mg/ml | m | pH | mM | mM | mM | 20% | 80% | U/ml |
| A | 120 | 20 | 5.5 | 210 | | 10 | 0.04 | | 12'000 |
| B | 120 | 20 | 5.5 | 210 | | 10 | | 0.06 | 12'000 |
| C | 120 | 20 | 5.5 | | 130 | 10 | 0.04 | | 12'000 |
| D | 120 | 20 | 5.5 | | 130 | 10 | | 0.06 | 12'000 |
| E | 120 | 20 | 5.5 | 105 | 65 | 10 | 0.04 | | 12'000 |
| F | 120 | 20 | 5.5 | 105 | 65 | 10 | | 0.06 | 12'000 |
| G | 120 | 20 | 5.5 | 210 | | 10 | 0.04 | | |
| H | 110 | 20 | 5.0 | 210 | | 5 | 0.02 | | 2'000 |
| I | 110 | 20 | 6.0 | 210 | | 5 | 0.02 | | 2'000 |
| J | 110 | 20 | 5.0 | 210 | | 5 | | 0.06 | 2'000 |
| K | 110 | 20 | 6.0 | 210 | | 5 | 0.06 | | 2'000 |
| L | 110 | 20 | 5.0 | 210 | | 15 | 0.02 | | 2'000 |
| M | 110 | 20 | 6.0 | 210 | | 15 | 0.02 | | 2'000 |
| N | 110 | 20 | 5.0 | 210 | | 15 | 0.06 | | 2'000 |
| O | 110 | 20 | 6.0 | 210 | | 15 | 0.06 | | 2'000 |
| P | 130 | 20 | 5.0 | 210 | | 5 | 0.02 | | 2'000 |
| Q | 130 | 20 | 6.0 | 210 | | 5 | 0.02 | | 2'000 |
| R | 130 | 20 | 5.0 | 210 | | 5 | 0.06 | | 2'000 |
| S | 130 | 20 | 6.0 | 210 | | 5 | 0.06 | | 2'000 |
| T | 130 | 20 | 5.0 | 210 | | 15 | 0.02 | | 2'000 |
| U | 130 | 20 | 6.0 | 210 | | 15 | 0.02 | | 2'000 |
| V | 130 | 20 | 5.0 | 210 | | 15 | 0.06 | | 2'000 |
| W | 130 | 20 | 6.0 | 210 | | 15 | 0.06 | | 2'000 |
| X | 120 | 20 | 5.5 | 210 | | 10 | 0.04 | | 2'000 |
| Y | 120 | 20 | 5.5 | 210 | | 10 | 0.04 | | 12'000 *) |

F = Formulation
His = L-histidine/HCl
NaCl = Sodium Chloride
PS = polysorbate in % (w/v)
*) = after reconstitution
Tr = Trastuzumab
tre = α,α-trehalose dihydrate
met = methionine
rHu = rHuPH20

What is claimed is:

1. A method of treating HER2-positive breast cancer in a patient comprising administering a highly concentrated, stable pharmaceutical formulation of Trastuzumab to the patient, wherein the Trastuzumab formulation comprises 120 mg/mL Trastuzumab, 20 mM L-histidine/HCl pH 5.5, 210 mM α,α-trehalose dihydrate, 10 mM methionine, 0.04% polysorbate 20, and 2000 U/mL hyaluronidase, and is administered subcutaneously, and wherein the method further comprises administering Pertuzumab to the patient.

2. The method of claim 1, further comprising administering chemotherapy to the patient.

3. A method of treating HER2-positive breast cancer in a patient comprising administering a highly concentrated, stable pharmaceutical formulation of Trastuzumab to the patient, wherein the Trastuzumab formulation comprises 120 mg/mL Trastuzumab, L-histidine/HCl pH 5.3 to 5.8, 210 mM α,α-trehalose dihydrate, 10 mM methionine, 0.04% polysorbate 20, and 1500 to 12000 U/mL hyaluronidase, and is administered subcutaneously, and wherein the method further comprises administering Pertuzumab to the patient.

4. The method of claim 3, further comprising administering chemotherapy to the patient.

* * * * *